(12) United States Patent
Wakefield et al.

(10) Patent No.: US 10,364,277 B2
(45) Date of Patent: Jul. 30, 2019

(54) DIAGNOSIS AND TREATMENT OF AUTOIMMUNE DISEASES

(71) Applicant: NewSouth Innovations Pty Limited, Sydney, New South Wales (AU)

(72) Inventors: Denis Wakefield, Sylvania (AU); Helder Marcal, Campsie (AU)

(73) Assignee: NEWSOUTH INNOVATIONS PTY LIMITED, New South Wales (AU)

( * ) Notice: Subject to any disclaimer, the term of this patent is extended or adjusted under 35 U.S.C. 154(b) by 0 days.

(21) Appl. No.: 14/902,381

(22) PCT Filed: Jun. 27, 2014

(86) PCT No.: PCT/AU2014/000664
§ 371 (c)(1),
(2) Date: Dec. 31, 2015

(87) PCT Pub. No.: WO2015/000014
PCT Pub. Date: Jan. 8, 2015

(65) Prior Publication Data
US 2016/0280750 A1    Sep. 29, 2016

(30) Foreign Application Priority Data

Jul. 1, 2013 (AU) .............................. 2013902435

(51) Int. Cl.
| | | |
|---|---|---|
| *G01N 33/53* | (2006.01) | |
| *C07K 14/47* | (2006.01) | |
| *A61K 39/00* | (2006.01) | |
| *G01N 33/564* | (2006.01) | |
| *A61K 38/00* | (2006.01) | |

(52) U.S. Cl.
CPC ...... *C07K 14/4725* (2013.01); *A61K 39/0005* (2013.01); *G01N 33/564* (2013.01); *A61K 38/00* (2013.01); *G01N 2800/24* (2013.01)

(58) Field of Classification Search
CPC ............ C07K 14/4725; A61K 39/0005; G01N 33/564
See application file for complete search history.

(56) References Cited

U.S. PATENT DOCUMENTS

| | | |
|---|---|---|
| 4,356,270 A | 10/1982 | Itakura |
| 4,376,110 A | 3/1983 | David et al. |
| 4,458,066 A | 7/1984 | Caruthers et al. |
| 4,582,788 A | 4/1986 | Erlich |
| 4,599,307 A | 7/1986 | Saunders et al. |
| 4,683,202 A | 7/1987 | Mullis |
| 4,704,891 A | 11/1987 | Recktenwald et al. |
| 4,727,020 A | 2/1988 | Recktenwald |
| 4,843,000 A | 6/1989 | Litman et al. |
| 4,849,338 A | 7/1989 | Litman et al. |
| 5,545,526 A | 8/1996 | Baxter-Lowe |
| 6,372,223 B1 | 4/2002 | Kistner et al. |
| 7,029,678 B2 | 4/2006 | Momin et al. |
| 2004/0005579 A1* | 1/2004 | Birse ...................... C07K 14/47 435/6.14 |
| 2011/0104062 A1 | 5/2011 | Siu |
| 2011/0183924 A1 | 7/2011 | Mintz et al. |

FOREIGN PATENT DOCUMENTS

| | | |
|---|---|---|
| EP | 0 399 843 A2 | 11/1990 |
| WO | 98/12221 A1 | 3/1998 |
| WO | 01/22992 A2 | 4/2001 |
| WO | 2007/006939 A2 | 1/2007 |
| WO | 2010/129310 A1 | 11/2010 |
| WO | 2011/119484 A1 | 9/2011 |
| WO | 2013/040142 A2 | 3/2013 |
| WO | 2013/081721 A1 | 6/2013 |

OTHER PUBLICATIONS

Schwimmbeck et al., (J Exp Med. Jul. 1, 1987; 166(1): 173-181).*
NCBI Reference Sequence Accession No. NP_008966.1, dated Jul. 1, 2018 (4 pages).
NCBI Reference Sequence Accession No. NP_055174.1, dated Jun. 23, 2018 (4 pages).
NCBI Reference Sequence Accession No. NP_220127.1, dated Aug. 3, 2016 (2 pages).
NCBI Reference Sequence Accession No. NP_478054.2, dated Nov. 17, 2018 (4 pages).
NCBI Reference Sequence Accession No. NP_001126.3, dated Nov. 17, 2018 (4 pages).
NCBI Reference Sequence Accession No. NP_149162.2, dated Nov. 18, 2018 (4 pages).
International Preliminary Report on Patentability dated Jan. 5, 2016 received in International Application No. PCT/AU2014/000664.
International Search Report dated Sep. 25, 2014 received in International Application No. PCT/AU2014/000664.
GenBank Accession No. AAC17741.1, dated Jul. 24, 2000 (2 pages).
NCBI Reference Sequence No. YR_002888714, dated Dec. 17, 2014 (2 pages).
Appel H. et al., "The Solvent-Inaccessible Cys67 Residue of HLA-B27 Contributes to T Cell Recognition of HLA-B27/Peptide Complexes", The Journal of Immunology 173:6564-6573 (2004).
Atagunduz P. et al., "HLA-B27-Restricted CD8+ T Cell Response to Cartilage-Derived Self Peptides in Ankylosing Spondylitis", Arthritis & Rheumatism 52(3):892-901 (Mar. 2005).

(Continued)

*Primary Examiner* — Christine J Saoud
(74) *Attorney, Agent, or Firm* — Scully, Scott, Murphy & Presser, P.C.

(57) ABSTRACT

The invention relates generally to the field of autoimmunity. More specifically, the invention relates to compositions and methods for the diagnosis, prevention, and treatment of human leukocyte antigen (HLA)-associated autoimmune diseases, and in particular HLA-B27-associated autoimmune diseases.

5 Claims, 6 Drawing Sheets
Specification includes a Sequence Listing.

(56) References Cited

OTHER PUBLICATIONS

Baranov V.I. et al., "Gene Expression in a Cell-Free System on the Preparative Scale", Gene 84:463-466 (1989).
Brown E.L. et al., "Chemical Synthesis and Cloning of a Tyrosine tRNA Gene", Methods in Enzymology 68:109-151 (1979).
Burrows J.M. et al., "The Impact of HLA-B Micropolymorphism Outside Primary Peptide Anchor Pockets on the CTL Response to CMV", Eur. J. Immunol. 37:946-953 (2007).
Cantagrel A. et al., "The Transsynovial Lymphocytic Ratio. Characterization of Blood and Synovial Fluid Lymphocytes from Patients With Arthritic Diseases", The Journal of Rheumatology 15(6):899-904 (1988).
Glant T.T. et al., "Mapping of Arthritogenic/Autoimmune Epitopes of Cartilage Aggrecans in Proteoglycan-Induced Arthritis", Scand J Rheumatol 24(Suppl 101):43-49 (1995).
Glimm H. et al., "Direct Evidence for Multiple Self-Renewal Divisions of Human in Vivo Repopulating Hematopoietic Cells in Short-Term Culture", The Journal of the American Society of Hematology 94(7):2161-2168 (Oct. 1, 1999).
Itakura K. et al., "Synthesis and Use of Synthetic Oligonucleotides", Annual Reviews of Biochemistry 53:323-356 (1984).
Khan M.A. et al., "Acute Anterior Uveitis and Spondyloarthritis: More Than Meets the Eye", Curr Rheumatol Rep 17:59 (2015).
Köhler G. et al, "Continuous Cultures of Fused Cells Secreting Antibody of Predefined Specificity", Nature 256:495-497 (Aug. 7, 1975).
Kozbor D. et al., "The Production of Monoclonal Antibodies from Human Lymphocytes", Immunology Today 4 (3):72-79 (1983).
Kudlicki W. et al., "High Efficiency Cell-Free Synthesis of Proteins: Refinement of the Coupled Transcription/Translation System", Analytical Biochemistry 206:389-393 (1992).
Kuon W. et al., "Identification of HLA-B27-Restricted Peptides in Reactive Arthritis and Other Spondyloarthropathies: Computer Algorithms and Fluorescent Activated Cell Sorting Analysis as Tools for Hunting of HLA-B27-Restricted Chlamydial and Autologous Crossreactive Peptides Involved in Reactive Arthritis and Ankylosing Spondylitis", Rheumatic Disease Clinics of North America 29:595-611 (2003).
Kuon W. et al., "Recognition of Chlamydial Antigen by HLA-B27-Restricted Cytotoxic T Cells in HLA-B*2705 Transgenic CBA (H-2K) Mice", Arthritis & Rheumatism 40(5):945-954 (May 1997).
Lesley S.A. et al., "Use of in Vitro Protein Synthesis from Polymerase Chain Reaction-Generated Templates to Study Interaction of *Escherichia Coli* Transcription Factors With Core RNA Polymerase and for Epitope Mapping of Monoclonal Antibodies", The Journal of Biological Chemistry 266(4):2632-2638 (1991).
Lyons A.B., "Analysing Cell Division in Vivo and in Vitro Using Flow Cytometric Measurement of CFSE Dye Dilution", Journal of Immunological Methods 243:147-154 (2000).
Lyons A.B. et al., "Determination of Lymphocyte Division by Flow Cytometry", Journal of Immunological Methods 171:131-137 (1994).
Madin K. et al., "A Highly Efficient and Robust Cell-Free Protein Synthesis System Prepared from Wheat Embryos: Plants Apparently Contain a Suicide System Directed at Ribosomes", PNAS 97(2):559-564 (Jan. 18, 2000).
Narang S.A. et al., "Improved Phosphotriester Method for the Synthesis of Gene Fragments", Methods in Enzymology 68:90-98 (1979).
Oostendorp R.A.J. et al., "High-Resolution Tracking of Cell Division Suggests Similar Cell Cycle Kinetics of Hematopoietic Stem Cells Stimulated in Vitro and in Vivo", Blood 95(3):855-862 (Feb. 1, 2000).
Parish C.R., "Fluorescent Dyes for Lymphocyte Migration and Proliferation Studies", Immunology and Cell Biology 77:499-508 (1999).
Pelham H.R.B. et al., "An Efficient mRNA-Dependent Translation System from Reticulocyte Lysates", Eur. J. Biochem. 67:247-256 (1976).
Quah B J C et al., "Monitoring Lymphocyte Proliferation in Vitro and in Vivo With the Intracellular Fluorescent Dye Carboxyfluorescein Diacetate Succinimidyl Ester", Nature Protocols 2(9):2049-2056 (2007).
Rada J.A. et al., "Regulation of Corneal Collagen Fibrillogenesis in Vitro by Corneal Proteoglycan (Lumican and Decorin) Core Proteins", Exp. Eye Res. 56:635-648 (1993).
Rammensee H-G et al., "SYFPEITHI: Database for MHC Ligands and Peptide Motifs", Immunogenetics 50:213-219 (1999).
Rammensee H-G et al., "MHC Ligands and Peptide Motifs: First Listing", Immunogenetics 41:178-228 (1995).
Roberts B.E. et al., "Efficient Translation of Tobacco Mosaic Virus RNA and Rabbit Globin 9S RNA in a Cell-Free System from Commercial Wheat Germ", Proc. Nat. Acad. Sci. USA 70(8):2330-2334 (Aug. 1973).
Thurau S.R. et al, "An HLA-Peptide Mimics Organ-Specific Antigen in Autoimmune Uveitis: Its Role in Pathogenesis and Therapeutic Induction of Oral Tolerance", Autoimmunity Reviews 2:171-176 (2003).
Traycoff C.M. et al., "Evaulation of Ex Vivo Expansion Potential of Cord Blood and Bone Marrow Hematopoetic Progenitor Cells Using Cell Tracking and Limiting Dilution Analysis", Blood 85(8):2059-2068 (Apr. 15, 1995).
Wakefield, MD D. et al., "What is New HLA-B27 Acute Anterior Uveitis?", Ocular Immunology & Inflammation 19 (2):139-144 (2011).
Young J.C. et al., "Retention of Quiescent Hematopoetic Cells With High Proliferative Potential During Ex Vivo Stem Cell Culture", Blood 87(2):545-556 (Jan. 15, 1996).
Zaunders J.J. et al., "High Levels of Human Antigen-Specific CD4+ T Cells in Peripheral Blood Revealed by Stimulated Coexpression of CD25 and CD134 (OX40)", The Journal of Immunology 183:2827-2836 (2009).
Zubay G., "In Vitro Synthesis of Protein in Microbial Systems", Ann. Rev. Genet. 7:267-287 (1973).
UniProtKB Accession No. E7 NLL7, dated Apr. 5, 2011 (3 pages).
NCBI Reference Sequence Accession No. WP_015455310.1, dated May 19, 2013 (1 page).
Ncbi Reference Sequence Accession No. WP_004891153.1, dated May 13, 2017 (1 page).
GenBank Accession No. AAC39517.1, dated Jul. 24, 2016 (2 pages).
UniProtKB Accession No. F7C663, dated Jul. 27, 2011 (4 pages).
UniProtKB/Swiss-Prot Accession No. P51884.2, dated Dec. 5, 2018 (6 pages).
GenBank Accession No. CAB53459.1, dated Oct. 7, 2008 (2 pages).
UniProtKB Accession No. A0A0H2X1R9, dated Sep. 16, 2015 (5 pages).
UniProtKB Accession No. P18584, dated Nov. 1, 1990 (7 pages).
NCBI Reference Sequence Accession No. NP_219980.1, dated Aug. 3, 2016 (2 pages).
NCBI Reference Sequence Accession No. NP_219924.1, dated Aug. 3, 2016 (2 pages).
UniProtKB/Swiss-Prot Accession No. Q3KL49, dated Oct. 31, 2006 (1 page).
UniProtKB/Swiss-Prot Accession No. Q3KMC1, dated Oct. 31, 2006 (2 pages).
UniProtKB/Swiss-Prot Accession No. P18584.2, dated Dec. 5, 2018 (3 pages).
UniProtKB/Swiss-Prot Accession No. Q5AR12, dated Oct. 31, 2006 (2 pages).
NCBI Reference Sequence Accession No. NP_002336.1, dated Nov. 22, 2018 (4 pages).
Supplementary European Search Report dated Jan. 19, 2017 received in European Application No. 14 81 9853.
Supplementary Partial European Search Report dated Jan. 19, 2017 received in European Application No. 14 81 9853.
European Search Report dated Mar. 29, 2018 received in European Application No. 14 81 9 853.4.

* cited by examiner

# DIAGNOSIS AND TREATMENT OF AUTOIMMUNE DISEASES

INCORPORATION BY CROSS REFERENCE

This application claims priority from Australian provisional patent application number 2013902435 filed on 1 Jul. 2013, the entire content of which is incorporated herein by cross-reference.

INCORPORATION BY REFERENCE OF SEQUENCE LISTING

The Sequence Listing in an ASCII text file, named as 32918_SubstituteSequenceListing.txt of 47 KB, created on Apr. 19, 2018, and submitted to the United States Patent and Trademark Office via EFS-Web, is incorporated herein by reference.

TECHNICAL FIELD

The invention relates generally to the field of autoimmunity. More specifically, the invention relates to compositions and methods for the diagnosis, prevention, and treatment of human leukocyte antigen (HLA)-associated autoimmune diseases, and in particular HLA-B27-associated autoimmune diseases.

BACKGROUND

A substantial number of autoimmune diseases in mammals are associated with the expression of specific major histocompatability complex (MHC) subtype(s). For example, spondyloarthropathies are a group of inflammatory autoimmune diseases associated with human leukocyte antigen B27 (HLA-B27) expression. Spondyloarthropathies affect the sacroiliac joints, axial skeleton, and, to a lesser degree, peripheral joints and certain extra-articular organs. Common spondyloarthropathies include ankylosing spondylitis (AS), reactive arthritis (RA) (also known as Reiter's syndrome), psoriatic arthritis, undifferentiated spondyloarthropathy, and juvenile onset spondyloarthropathy (collectively termed the B27 diseases). A significant proportion of patients affected by spondyloarthropathies develop anterior uveitis, an autoreactive inflammation localized primarily to the anterior segment of the eye. Spondyloarthropathies and anterior uveitis appear to be triggered by certain bacteria, and are particularly prevalent in HLA-B27 positive individuals. For example, ankylosing spondylitis (AS) has a greater than 90% correspondence with the expression of HLA-B27.

The diagnosis of spondyloarthropathies and anterior uveitis relies predominantly on clinical and radiological criteria which are often unreliable and misdiagnosis is common. Treatments consist primarily of symptom-relieving drugs which have minimal effect on the underlying causes of the disease. Furthermore, effective preventative treatments for spondyloarthropathies and anterior uveitis are virtually non-existent.

There is a need for improved agents and methods for the treatment and/or prevention of HLA-associated diseases such as spondyloarthropathies and anterior uveitis. A need also exists for improved agents and methods to diagnose these diseases and identify individuals predisposed to developing them.

SUMMARY OF THE INVENTION

In a first aspect, the invention provides an isolated polypeptide comprising a sequence of at least six amino acid residues, wherein said sequence shares at least 65% sequence homology with:
 (a) a mammalian small leucine-rich repeat protein/proteoglycan (SLRP) polypeptide sequence; and
 (b) a polypeptide sequence from an infectious microorganism,
wherein said SLRP is selected from lumican, opticin and keratocan.

In one embodiment of the first aspect, the sequence shares 75% with the mammalian SLRP polypeptide sequence and the polypeptide sequence from the infectious microorganism.

In one embodiment of the first aspect, the sequence shares 80% with the mammalian SLRP polypeptide sequence and the polypeptide sequence from the infectious microorganism.

In one embodiment of the first aspect, the sequence shares 85% with the mammalian SLRP polypeptide sequence and the polypeptide sequence from the infectious microorganism.

In one embodiment of the first aspect, the sequence shares 90% with the mammalian SLRP polypeptide sequence and the polypeptide sequence from the infectious microorganism.

In one embodiment of the first aspect, the sequence shares 95% with the mammalian SLRP polypeptide sequence and the polypeptide sequence from the infectious microorganism.

In one embodiment of the first aspect, the isolated polypeptide is 12 amino acid residues or less in length.

In one embodiment of the first aspect, the isolated polypeptide is nine amino acid residues in length.

In one embodiment of the first aspect, the infectious microorganism is a species from genus *Chlamydia* or *Aspergillus*.

In one embodiment of the first aspect, the infectious microorganism is *Chlamydia trachomatis*.

In one embodiment of the first aspect, the infectious microorganism is *Aspergillus nidulans*.

In one embodiment of the first aspect, the polypeptide sequence of (b) comprises SEQ ID NO: 5, SEQ ID NO: 6, SEQ ID NO: 7, SEQ ID NO: 8, SEQ ID NO: 36, SEQ ID NO: 37, or SEQ ID NO: 38.

In one embodiment of the first aspect, the polypeptide sequence of (a) comprises residues 222-275 of the amino acid sequence set forth in SEQ ID NO: 1.

In one embodiment of the first aspect, the polypeptide sequence of (a) comprises residues 222-247 of the amino acid sequence set forth in SEQ ID NO: 1.

In one embodiment of the first aspect, the polypeptide sequence of (a) comprises residues 222-241 of the amino acid sequence set forth in SEQ ID NO: 1.

In one embodiment of the first aspect, the sequence of at least six amino acid residues comprises SEQ ID NO: 2 (KRFNALQYL).

In one embodiment of the first aspect, the sequence of at least six amino acid residues consists of SEQ ID NO: 2 (KRFNALQYL).

In one embodiment of the first aspect, the sequence of at least six amino acid residues comprises a variant of SEQ ID NO: 2 (KRFNALQYL) comprising at least one amino acid substitution.

In one embodiment of the first aspect, the variant is selected from the group consisting of KRFNALQCL (SEQ ID NO: 3) or KRFNALQLL (SEQ ID NO: 4), or a fragment thereof.

In one embodiment of the first aspect, the sequence of at least six amino acid residues comprises a fragment of SEQ ID NO: 2 (KRFNALQYL).

In one embodiment of the first aspect, the fragment is selected from a sequence set forth in any one of SEQ ID NOs: 9-17.

In one embodiment of the first aspect, the polypeptide comprises a fragment of KRFNALQCL (SEQ ID NO: 3) or KRFNALQLL (SEQ ID NO: 4) selected from a sequence set forth in any one of SEQ ID NOs: 18-29.

In one embodiment of the first aspect, the sequence of at least six amino acid residues comprises SEQ ID NO: 34 (LQYLRLSHN).

In one embodiment of the first aspect, the sequence of at least six amino acid residues consists of SEQ ID NO: 34 (LQYLRLSHN).

In one embodiment of the first aspect, the polypeptide sequence of (a) comprises residues 264-315 of the amino acid sequence set forth in SEQ ID NO: 30.

In one embodiment of the first aspect, the sequence of at least six amino acid residues comprises SEQ ID NO: 31 (LQNNLIETM) or SEQ ID NO: 35 (QLEDIRLDG).

In one embodiment of the first aspect, the sequence of at least six amino acid residues consists of SEQ ID NO: 31 (LQNNLIETM) or SEQ ID NO: 35 (QLEDIRLDG).

In one embodiment of the first aspect, the polypeptide sequence of (a) comprises residues 264-315 of the amino acid sequence set forth in SEQ ID NO: 32.

In one embodiment of the first aspect, the sequence of at least six amino acid residues comprises SEQ ID NO: 33 (LQNNLIETI).

In one embodiment of the first aspect, the sequence of at least six amino acid residues consists of SEQ ID NO: 33 (LQNNLIETI).

In one embodiment of the first aspect, the binding affinity of said sequence of at least six amino acid residues to human leukocyte antigen B27 (HLA-B27) as measured by $IC_{50}$ value is less than about 500 nm.

In another embodiment of the first aspect, the binding affinity of said sequence of at least six amino acid residues to human leukocyte antigen B27 (HLA-B27) as measured by $IC_{50}$ value is less than about 100 nm.

In another embodiment of the first aspect, the binding affinity of said sequence of at least six amino acid residues to human leukocyte antigen B27 (HLA-B27) as measured by $IC_{50}$ value is less than about 50 nm.

In a second aspect, the invention provides a pharmaceutical composition comprising an isolated polypeptide of the first aspect.

In one embodiment of the second aspect, the pharmaceutical composition further comprises a pharmaceutically acceptable carrier, diluent or adjuvant.

In one embodiment of the second aspect, the pharmaceutical composition is a preventative or therapeutic vaccine.

In a third aspect, the invention provides a method for preventing or treating an HLA-associated autoimmune disease in a subject, the method comprising administering to the subject a therapeutically effective amount of an isolated polypeptide of the first aspect, or a pharmaceutical composition of the second aspect.

In a fourth aspect, the invention provides a method for determining a predisposition to developing an HLA-associated autoimmune disease in a subject, the method comprising:

contacting a biological sample from the subject with a polypeptide of the first aspect; and detecting the presence or absence of an immune cell or antibody specific for said polypeptide in the biological sample, wherein detection of said immune cell or antibody is indicative of a predisposition to developing the disease.

In a fifth aspect, the invention provides a method for diagnosing an HLA-associated autoimmune disease in a subject, the method comprising:

contacting a biological sample from the subject with an isolated polypeptide of the first aspect; and detecting the presence or absence of an immune cell or antibody specific for said polypeptide in the biological sample, wherein detection of said immune cell or antibody is indicative of a predisposition to developing the disease.

In one embodiment of the fourth or fifth aspect, the method comprises the additional step of determining the human leukocyte antigen type (HLA-type) of the subject.

In one embodiment of the fourth or fifth aspect, the detecting comprises:

(i) analysing antibody binding by enzyme-linked immunosorbent assay (ELISA), (ii) analysing cell proliferation, (iii) analysing cytokine synthesis, or (iv) analysing cell surface marker expression.

In one embodiment of the fourth or fifth aspect, the immune cell is a $CD4^+$ T lymphocyte or a $CD8^+$ T lymphocyte.

In one embodiment of the third, fourth or fifth aspect, the HLA-associated autoimmune disease is an HLA-B27-associated autoimmune disease.

In one embodiment of the third, fourth or fifth aspect, the HLA-associated autoimmune disease is a spondyloarthropathy or anterior uveitis.

In one embodiment of the third, fourth or fifth aspect, the spondyloarthropathy is selected from the group consisting of ankylosing spondylitis, psoriatic arthritis, undifferentiated spondyloarthropathy, juvenile onset spondyloarthropathy, enteropathic arthritis, arthritis mutilans, reactive arthritis (Reiter's syndrome), reactive arthritides, sacroiliitis, spondylitis of inflammatory bowel disease, Crohn's disease associated with spondyloarthropathy, whipple disease, and Behcet disease.

In one embodiment of the third, fourth or fifth aspect, the anterior uveitis is acute anterior uveitis.

In one embodiment of the third, fourth or fifth aspect, the anterior uveitis is chronic anterior uveitis.

In a sixth aspect, the invention provides an antibody specific for a polypeptide of the first aspect.

In a seventh aspect, the invention provides an isolated polypeptide of the first aspect or a pharmaceutical composition of the second aspect, for use in preventing or treating an HLA-associated autoimmune disease.

In an eighth aspect, the invention provides a use of an isolated polypeptide of the first aspect for the preparation of a medicament for preventing or treating an HLA-associated autoimmune disease.

In one embodiment of the seventh or eighth aspect, the HLA-associated autoimmune disease is an HLA-B27-associated autoimmune disease.

In one embodiment of the seventh or eighth aspect, the HLA-associated autoimmune disease is a spondyloarthropathy or anterior uveitis.

In one embodiment of the seventh or eighth aspect, the spondyloarthropathy is selected from the group consisting of ankylosing spondylitis, psoriatic arthritis, undifferentiated spondyloarthropathy, juvenile onset spondyloarthropathy, enteropathic arthritis, arthritis mutilans, reactive arthritis (Reiter's syndrome), reactive arthritides, sacroiliitis, spondylitis of inflammatory bowel disease, Crohn's disease associated with spondyloarthropathy, whipple disease, and Behcet disease.

In one embodiment of the seventh or eighth aspect, the anterior uveitis is acute anterior uveitis.

In one embodiment of the seventh or eighth aspect, the anterior uveitis is chronic anterior uveitis.

BRIEF DESCRIPTION OF THE DRAWINGS

Preferred embodiments of the invention will now be described, by way of example only, with reference to the accompanying figures wherein.

DEFINITIONS

Figure 1:
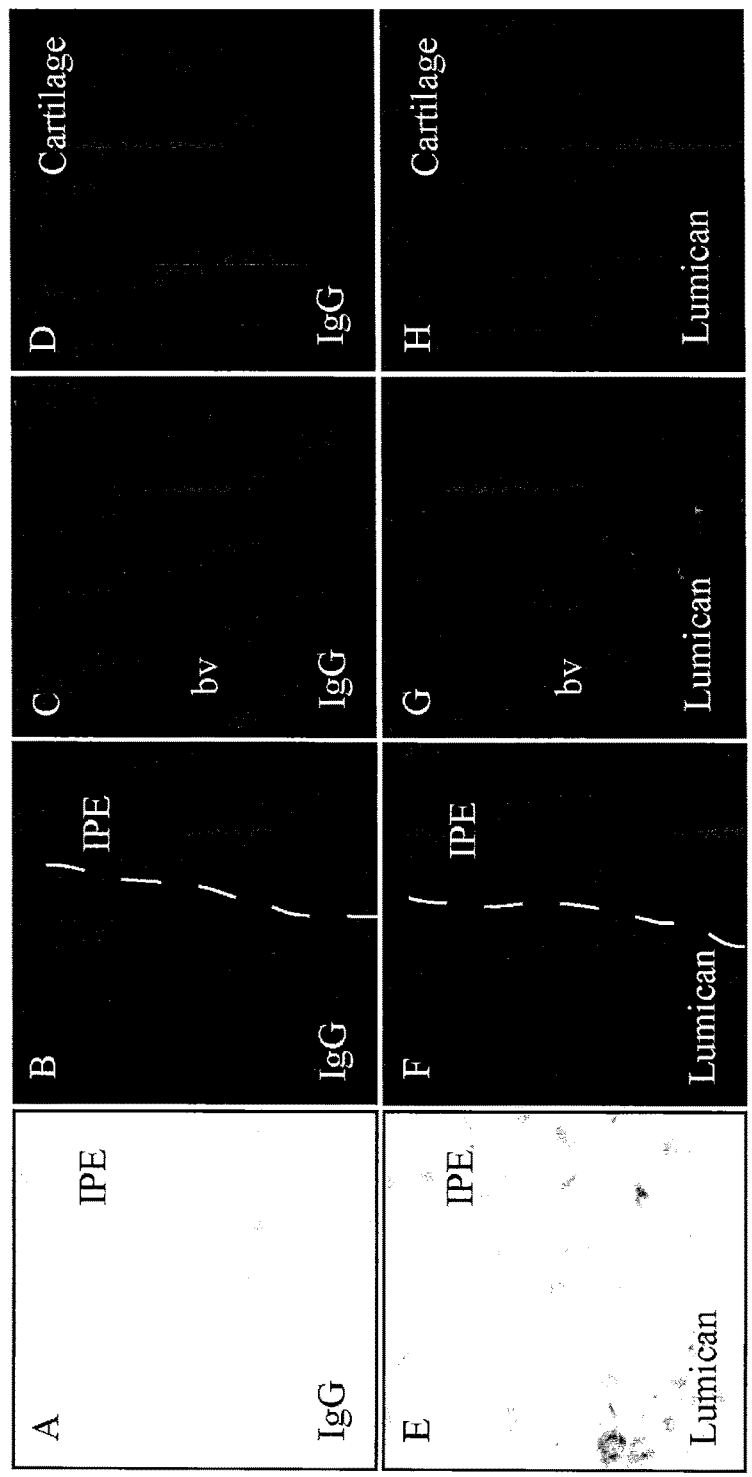
FIG. 1 provides fluorescence microscopy images showing lumican expression in human iris epithelial cells (1A and 1E), iris tissues (1B and 1F), and synovial tissues (1C-1D, 1G-1H). Original magnification ×100 (1A, 1E) and ×400 (1B-1D, 1F-1H)

As used in this application, the singular form "a", "an" and "the" include plural references unless the context clearly dictates otherwise. For example, the term "a polypeptide" also includes a plurality of polypeptides.

As used herein, the term "comprising" means "including." Variations of the word "comprising", such as "comprise" and "comprises," have correspondingly varied meanings. Thus, for example, a polypeptide "comprising" a sequence of amino acid residues may consist exclusively of that sequence of amino acid residues or may include one or more additional amino acid residues.

As used herein the term "plurality" means more than one. In certain specific aspects or embodiments, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

The term "therapeutically effective amount" as used herein, includes within its meaning a non-toxic but sufficient amount of a compound or composition for use in the invention to provide the desired therapeutic effect. The exact amount required will vary from subject to subject depending on factors such as the species being treated, the age and general condition of the subject, the severity of the condition being treated, the particular agent being administered, the mode of administration and so forth. Thus, it is not possible to specify an exact "effective amount". However, for any given case, an appropriate "effective amount" may be determined by one of ordinary skill in the art using only routine experimentation.

As used herein, the term "subject" includes any animal of economic, social or research importance including bovine, equine, ovine, primate, avian and rodent species. Hence, a "subject" may be a mammal such as, for example, a human or a non-human mammal.

As used herein, the terms "antibody" and "antibodies" include IgG (including IgG1, IgG2, IgG3, and IgG4), IgA (including IgA1 and IgA2), IgD, IgE, or IgM, and IgY, whole antibodies, including single-chain whole antibodies, and antigen-binding fragments thereof. Antigen-binding antibody fragments include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin. Antigen-binding antibody fragments, including single-chain antibodies, may comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies may be monoclonal, polyclonal, chimeric, multispecific, humanized, and human monoclonal and polyclonal antibodies which specifically bind the biological molecule.

As used herein, the terms "protein" and "polypeptide" each refer to a polymer made up of amino acids linked together by peptide bonds and are used interchangeably herein. For the purposes of the present invention a "polypeptide" may constitute a full length protein or a portion of a full length protein.

As used herein, the term "polynucleotide" refers to a single- or double-stranded polymer of deoxyribonucleotide, ribonucleotide bases or known analogues or natural nucleotides, or mixtures thereof.

As used herein, the term "kit" refers to any delivery system for delivering materials. Such delivery systems include systems that allow for the storage, transport, or delivery of reaction reagents (for example labels, reference samples, supporting material, etc. in the appropriate containers) and/or supporting materials (for example, buffers, written instructions for performing the assay etc.) from one location to another. For example, kits include one or more enclosures, such as boxes, containing the relevant reaction reagents and/or supporting materials. The term "kit" includes both fragmented and combined kits.

As used herein, the term "fragmented kit" refers to a delivery system comprising two or more separate containers that each contains a subportion of the total kit components. The containers may be delivered to the intended recipient together or separately. Indeed, any delivery system comprising two or more separate containers that each contains a subportion of the total kit components are included in the term "fragmented kit". In contrast, a "combined kit" refers to a delivery system containing all of the components of a reaction assay in a single container (e.g. in a single box housing each of the desired components).

As used herein, an "MHC-associated autoimmune disease" encompasses any autoimmune disease that, in a given population of subjects, has an increased prevalence in subjects expressing a specific MHC allele or a specific combination of MHC alleles, compared to subjects that do not express that specific MHC allele or that specific combination of MHC alleles. It will be understood that an "MHC-associated autoimmune disease" as used herein includes, but is not limited to, an "HLA-associated autoimmune disease".

As used herein, an "HLA-associated autoimmune disease" encompasses any autoimmune disease that, in a given population of human subjects, has an increased prevalence in subjects expressing a specific HLA allele or a specific combination of HLA alleles, compared to subjects that do not express that specific HLA allele or that specific combination of HLA alleles. It will be understood that an "HLA-associated autoimmune disease" as used herein includes, but is not limited to, an "HLA-B27 associated autoimmune disease".

As used herein, an "HLA-B27 associated autoimmune disease" encompasses any autoimmune disease or condition that, in a given population of human subjects, has an increased prevalence in subjects that are homozygous for an HLA-B27 allele compared to subjects that are not homozygous for an HLA allele, and/or has an increased prevalence in subjects that are heterozygous for an HLA-B27 allele compared to subjects that do not express an HLA allele.

It will be understood that use the term "about" herein in reference to a recited numerical value includes the recited numerical value and numerical values within plus or minus ten percent of the recited value. Any description of prior art documents herein, or statements herein derived from or based on those documents, is not an admission that the documents or derived statements are part of the common general knowledge of the relevant art.

It will be understood that use of the term "between" herein when referring to a range of numerical values encompasses the numerical values at each endpoint of the range. For example, a polypeptide of between 10 residues and 20 residues in length is inclusive of a polypeptide of 10 residues in length and a polypeptide of 20 residues in length.

Any description of prior art documents herein, or statements herein derived from or based on those documents, is not an admission that the documents or derived statements are part of the common general knowledge of the relevant art.

For the purposes of description all documents referred to herein are hereby incorporated by reference in their entirety unless otherwise stated.

DETAILED DESCRIPTION

The present invention relates to the finding that certain proteins of infectious microorganisms induce autoimmune responses leading to the destruction of host cells and tissues. Without being limited to a particular mode of action, it is proposed that host immune cells and antibodies directed towards specific antigenic determinants in proteins of infectious microorganisms aberrantly recognise similar or identical antigenic determinants present in a specific host proteins identified herein. The aberrant recognition of antigenic determinants in these host proteins instigates the destruction of cells and tissues in which they are expressed.

The present invention thus relates to the identification of antigenic determinants in proteins of infectious microorganisms that induce autoimmune responses against proteins of an infected host organism. The present invention also relates to the identification of antigenic determinants in host proteins targeted by cross-reactive immune responses arising upon infection/re-infection by certain microorganisms.

Some aspects of the present invention relate to polypeptides comprising region(s) of sequence homology shared by host proteins and proteins of infectious microorganisms. These region(s) of sequence homology are proposed to be responsible for the development of autoreactive immune cells and antibodies in subjects suffering from HLA-associated autoimmune diseases including spondyloarthropathies and anterior uveitis. The polypeptides may be incorporated into pharmaceutical compositions such as preventative and therapeutic vaccines.

Other aspects of the present invention relate to methods for preventing or treating HLA-associated autoimmune diseases (e.g. spondyloarthropathies and anterior uveitis) by administering polypeptides or compositions of the invention.

Additional aspects of the present invention relate to methods for diagnosing or prognosing HLA-associated autoimmune diseases (e.g. spondyloarthropathies and anterior uveitis) by detection of immune cells or antibodies specific for polypeptides of the invention in, for example, a biological sample derived from a subject of interest.

Polypeptides and Polynucleotides

Polypeptides

The invention provides polypeptides having sequence homology with at least one protein of an infectious microorganism and a small leucine-rich repeat protein/proteoglycan (SLRP) of a host organism susceptible to infection by the microorganism. The host may be any animal of economic, social or research importance including bovine, equine, ovine, primate, avian and rodent species. In certain embodiments the host may be a mammal. The mammal may be, for example, a human. The human may be positive for HLA-B27.

As contemplated herein "sequence homology" between two given sequences refers to the degree of sequence homology over the specific region defined by the sequences when optimally aligned.

Polypeptides of the invention share sequence homology with at least one protein of an infectious microorganism and at least one mammalian small leucine-rich repeat protein/proteoglycan (SLRP) expressed by a host susceptible to infection by the microorganism. Preferably, the host protein is lumican, opticin or keratocan.

It is postulated that the horseshoe-like shape of SLRPs such as lumican, opticin and keratocan may provide entry points for infectious microorganisms (e.g. bacteria). Furthermore, it is believed that differential keratin sulphate patterns in SLRPs such as lumican, opticin and keratocan occurring at different stages of development (e.g. infant vs adult) may be responsible, at least in part, for the increased susceptibility of specific age groups to spondyloarthropathies and/or anterior uveitis (e.g. the faster onset of juvenile spondyloarthropathies).

Polypeptides of the invention may share sequence homology with a mammalian lumican protein. The mammalian lumican protein may be a human lumican protein.

The human lumican protein may have the sequence set forth in SEQ ID NO: 1 (GenBank accession no. P51884), or a variant or a fragment thereof.

In certain embodiments, polypeptides of the invention may have sequence homology with a specific region of the human lumican protein. The region of the human lumican protein may be defined by residues 222-275 of the sequence set forth in SEQ ID NO: 1, or a fragment thereof. The region may be defined by residues 222-247 of the sequence set forth in SEQ ID NO: 1, or a fragment thereof. The region may be defined by residues 222-241 of the sequence set forth in SEQ ID NO: 1, or a fragment thereof. The region may be defined by the sequence set forth in SEQ ID NO: 2, SEQ ID NO: 3, SEQ ID NO: 4, SEQ ID NO: 34, or a fragment thereof.

The human opticin protein may have the sequence set forth in SEQ ID NO: 30 (GenBank accession no. CAB53459), or a variant or a fragment thereof.

In certain embodiments, polypeptides of the invention have sequence homology with a specific region of the human opticin protein. The region of the human opticin protein may be defined by residues 264-315 of the sequence set forth in SEQ ID NO: 30, or a fragment thereof. The region may be defined by the sequence set forth in SEQ ID NO: 31, SEQ ID NO: 35, or a fragment thereof.

In certain embodiments, polypeptides of the invention have sequence homology with a specific region of the human keratocan protein. The human keratocan protein may have the sequence set forth in SEQ ID NO: 32 (GenBank accession no. AAC 17741.1), or a variant or a fragment thereof. The region of the human keratocan protein may be defined by residues 71-91 of the sequence set forth in SEQ ID NO: 32, or a fragment thereof. The region may be defined by the sequence set forth in SEQ ID NO: 33, or a fragment thereof. Polypeptides of the invention share sequence homology with at least one host lumican protein. The polypeptide may share at least about 40%, 45%, 50%, 55%, 60%, 65%, 70%, 75%, 80%, 85%, 90%, 95% or greater than 95% sequence homology with the host SLRP protein such as, for example, a host lumican protein, a host opticin protein, or a host keratocan protein.

In certain embodiments of the invention, the polypeptide shares 100% sequence homology with a host SLRP protein (e.g. lumican, opticin or keratocan). Accordingly, a polypeptide of the invention may be identical to a host SLRP protein (e.g. a mammalian lumican, opticin or keratocan protein) or a fragment of a host SLRP protein (e.g. a fragment of a mammalian lumican, opticin or keratocan protein). Alternatively, the polypeptide may comprise a sequence that is identical to a host SLRP sequence (e.g. a mammalian lumican, opticin or keratocan protein sequence) or a fragment of a host SLRP sequence (e.g. a fragment of a mammalian host lumican, opticin or keratocan sequence).

Polypeptides of the invention share sequence homology with at least one protein of an infectious microorganism. It will be understood that an "infectious microorganism" as contemplated herein is a reference to a microorganism capable of establishing an infection in a host (e.g. a mammalian host). Non-limiting examples of infectious microorganisms from which the proteins may be derived include bacteria and fungi.

For example, in certain embodiments the protein is from a bacterium. Non-limiting examples include species of the genus *Chlamydia* (e.g. *C. trachomatis, C. pneumoniae*). Bacterial proteins to which polypeptides of the invention may share sequence homology include, but are not limited to, *Chlamydia* sp. fructose biphosphate aldolase protein (NCBI Reference Sequence: YP_002888714.1—SEQ ID NO: 5), OMP85 protein (Swiss-Prot: Q3KMC1—SEQ ID NO: 6), serine protease do-like protein (Swiss-Prot: P18584.2—SEQ ID NO: 7). 2-component regulatory system-sensor histidine kinase (NCBI Reference Sequence: NP_219980.1), hypothetical protein CT610 (NCBI Reference Sequence: NP_220127.1), or putative outer membrane protein C (NCBI Reference Sequence: NP_219924.1).

Non-limiting examples of bacterial peptides to which polypeptides of the invention may share sequence homology include those set forth in SEQ ID NO: 36, SEQ ID NO: 37, and SEQ ID NO: 38.

In other embodiments, the protein is from a fungus/yeast. Non-limiting examples include species of the genus *Aspergillus* (also known as *Emericella*) (e.g. *A. nidulans/E. nidulans*).

Fungal/yeast proteins to which polypeptides of the invention may share sequence homology include, but are not limited to, *Aspergillus* sp. uncharacterised protein (Swiss-Prot: Q5AR12—SEQ ID NO: 8).

Polypeptides of the invention share sequence homology with at least one protein of an infectious microorganism. The polypeptide may share at least about 40%, 45%, 50%, 55%, 60%, 65%, 70%, 75%, 80%, 85%, 90%, 95% or greater than 95% sequence homology with the protein(s).

In certain embodiments of the invention, the polypeptide shares 100% sequence homology with protein(s) of an infectious microorganism. Accordingly, a polypeptide of the invention may be identical to at least one protein of an infectious microorganism or a fragment of at least one protein of an infectious microorganism. Alternatively, the polypeptide may comprise a sequence that is identical to at least one protein of an infectious microorganism or a fragment of at least one protein of an infectious microorganism.

It will be understood that the degree of sequence homology between a polypeptide of the invention and a host SLRP protein (e.g. lumican, opticin or keratocan) need not be identical to the degree of sequence homology between that polypeptide and protein(s) of an infectious microorganism, although such a possibility is not excluded.

Accordingly, a polypeptide of the invention may exhibit any of the aforementioned percentages of sequence homology with a host SLRP protein (e.g. lumican, opticin or keratocan) in combination with any of the aforementioned percentages of sequence homology with protein(s) of an infectious microorganism.

The percentage of sequence identity between two sequences may be determined by comparing two optimally aligned sequences over a comparison window. A portion of a sequence (e.g. a polypeptide of the invention) in the comparison window may, for example, comprise deletions or additions (i.e. gaps) in comparison to a reference sequence (e.g. a host or bacterial protein) which does not comprise deletions or additions, in order to align the two sequences optimally, or vice versa. A percentage of sequence identity may then be calculated by determining the number of positions at which an identical amino acid residue occurs in both sequences to yield the number of matched positions, dividing the number of matched positions by the total number of positions in the window of comparison and multiplying the result by 100 to yield the percentage of sequence identity.

Hence, in the context of two or more polypeptide sequences the percentage of sequence identity refers to the specified percentage of amino acid residues that are the same over a specified region when compared and aligned for maximum correspondence over a comparison window, or designated region as measured, for example, using one of the following sequence comparison algorithms or by manual alignment and visual inspection.

For sequence comparison, typically one sequence acts as a reference sequence to which test sequence(s) are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percentage of sequence homology for the test sequence(s) relative to the reference sequence, based on the program parameters.

Methods of alignment of sequences and/or the determination of sequence homology are known in the art and can be achieved conventionally using known computer programs including, but not limited to, CLUSTAL in the PC/Gene program (available from Intelligenetics, Mountain View, Calif.), the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA).

A polypeptide of the invention may be of any length.

As will be recognised by the skilled addressee, a polypeptide sequence as exemplified herein may further include one, two, three, four, five or more than five additional amino acids immediately upstream (i.e. 5') and/or downstream (i.e. 3') of the exemplified polypeptide. The additional amino acid(s) may be selected from the group consisting of A, R, N, D, C, E, Q, G, H, I, L, K, M, F, P, S, T, W, Y or V.

The additional amino acid(s) may, for example, correspond to amino acids immediately upstream and/or downstream in the amino acid sequence of an SLRP protein (e.g. lumican, opticin or keratocan) of which the polypeptide is a constituent. Alternatively, the additional amino acids may not correspond to amino acids immediately upstream and/or downstream in the amino acid sequence of the protein from which the polypeptide is a constituent.

The skilled addressee will also recognise that one or more amino acids of a polypeptide of the invention as exemplified herein may be deleted or substituted without necessarily reducing the immunogenic activity of the polypeptide.

In certain embodiments, polypeptides of the invention may be used to stimulate an immune response in a host. In other embodiments, polypeptides of the invention may be used to induce tolerance to an antigen in a host. In other embodiments, polypeptides of the invention may be used to detect the presence of immune cells and/or antibodies specific for the polypeptides in biological samples. Accordingly, a polypeptide of the invention may be of a length suitable for processing by host immune cells (e.g. antigen presenting cells) and subsequent binding to major histocompatibility (MHC) proteins.

In preferred embodiments, a polypeptide of the invention may comprise at least (or at least about) 5, 6, 7, 8, 9, 10, 11, 12, 13, 14, 15, 17, 20, 25, 30, 35, 40, 45, or 50 amino acids.

In other preferred embodiments, a polypeptide of the invention may comprise less than (or less than about) 5, 6, 7, 8, 9, 10, 11, 12, 13, 14, 15, 17, 20, 25, 30, 35, 40, 45, or 50 amino acids.

Accordingly, in some preferred embodiments a polypeptide of the invention may comprise (or comprise about) 5, 6, 7, 8, 9, 10, 11, 12, 13, 14, 15, 16, 17, 18, 19, 20, 21, 22, 23, 24, 25, 26, 27, 28, 29, 30 or more than 30 amino acids.

In certain embodiments, polypeptides of the invention comprise less than 15 amino acids. In other embodiments, polypeptides of the invention comprise less than 12 amino acids. In some preferred embodiments, polypeptides of the invention comprise or consist of eight amino acids or nine amino acids. In other preferred embodiments, polypeptides of the invention comprise or consist of an amino acid sequence as set out in any of SEQ ID NOs: 2, 3, 4, 9-29, 31 or 33-40.

Polypeptides of the invention may be expressed as antigens by host immune cells. Typically, polypeptides of the invention introduced to host immune cells are processed and displayed on the cell surface bound to Major Histocompatibility Complex (MHC) proteins of the cell. The display of these antigenic determinants in association with the MHC proteins may elicit the proliferation of host immune cells including T-lymphocyte clones specific to the determinants. In humans, MHC proteins are Human Leukocyte Antigen (HLA) proteins.

A polypeptide of the invention may be of a length and/or conformation suitable for binding to an MHC class I protein (e.g. between about 6 and about 12 residues) and may comprise a hydrophobic residue at its C-terminus.

For example, a polypeptide of the invention may be of a length and/or conformation suitable for binding to a human MHC class I protein (e.g. any one or more of the HLA-A, HLA-B, HLA-C, HLA-D, HLA-E, HLA-F, or HLA-G subtypes).

In certain embodiments, the polypeptide is of a length and/or conformation suitable for binding to a human MHC class I protein associated with spondyloarthropathies and/or anterior uveitis (e.g. anterior acute uveitis). For example, a polypeptide of the invention may be of a length and/or conformation suitable for binding to an HLA-B protein (e.g. HLA-B2705, HLA-B1503), or an HLA-A protein (e.g. HLA-A0202, HLA-A2301, HLA-A2902).

In one embodiment, the polypeptide is of a length and/or conformation suitable for binding to HLA-B27. The polypeptide may be of a length and/or conformation suitable for binding to any HLA-B27 allele (e.g. HLA-B2701-HLA-B2728) including, but not limited to, HLA-B2705.

A polypeptide of the invention may be of a length and/or conformation suitable for binding to an MHC class II protein (e.g. between about 14 and about 24 residues).

For example, a polypeptide of the invention may be of a length and/or conformation suitable for binding to a human MHC class II protein (e.g. HLA-DM-Alpha, HLA-DM-Beta, HLA-DO-Alpha, HLA-DO-Beta, HLA-DP-Alpha1, HLA-DQ-Alpha1, HLA-DQ-Alpha2, HLA-DQ-Beta1, HLA-DR-Alpha, HLA-DR-Beta1, HLA-DR-Beta3, HLA-DR-Beta4 or HLA-DR-Beta5).

In certain embodiments, the polypeptide is of a length and/or conformation suitable for binding to a human MHC class II protein associated with autoimmune disease(s). For example, a polypeptide of the invention may be of a length and/or conformation suitable for binding to an HLA-DR protein (e.g. HLA-DR01, DR0404 and HLA-DR0405).

In one embodiment, the polypeptide is of a length and/or conformation suitable for binding to HLA-DR4. The polypeptide may be of a length and/or conformation suitable for binding to any HLA-DR4 allele (e.g. HLA-DR0401-HLA-DR0460) including, but not limited to, HLA-0401, HLA-DR0404 and HLA-DR0405.

Preferably, polypeptides of the invention bind to MHC proteins (e.g. HLA proteins) with high affinity. For example, the affinity of a polypeptide of the invention for a given MHC protein (as measured by $IC_{50}$) may less than about 500 nM, less than about 400 nM, less than about 300 nM, less than about 200 nM, less than about 100 nM, less than about 50 nM, less than about 40 nM, less than about 30 nM, less than about 20 nM, less than about 10 nM, or less than about 5 nM.

Polypeptides of the invention (including fusion polypeptides described in the subsection below entitled "Fusion polypeptides") may be immunogenic polypeptides. For example, a polypeptide of the invention may comprise one or more epitopes capable of being recognized and bound by the immune cells and/or antibodies of an organism to which the polypeptide is administered. Preferably, the immune cells of the host organism capable of recognising and binding the polypeptides are T lymphocytes. In some embodiments, polypeptides of the invention are capable of inducing immunological tolerance.

Fusion Polypeptides

A polypeptide of the invention may be included as a component part of a longer amino acid sequence. For example, a polypeptide of the invention may be present within a fusion protein/fusion polypeptide wherein the polypeptide is linked with one or more amino acid sequences to which it would not be linked to in nature.

In this context it will be understood that a fusion polypeptide may comprise a plurality of polypeptides of the invention, such as where two polypeptides, three polypeptides, four polypeptides, or five polypeptides or more of the invention are present in a single fusion polypeptide. Any combination of polypeptides of the invention may be contemplated. In preferred embodiments a plurality of polypeptides may be selected such that the fusion polypeptide comprises polypeptides identified as comprising advantageous immunogenic responses in a given set of circumstances, as can be determined by the skilled addressee.

A fusion polypeptide comprising one or more polypeptide(s) of the invention may additionally comprise one or more unrelated sequences. In this context it will be understood that an "unrelated sequence" is a sequence which is not present in an SLRP (e.g. lumican, opticin or ketatocan) or infectious microorganism protein sequence from which any of the polypeptide(s) in the fusion polypeptide may correspond or share sequence homology with. Such a sequence will generally be referred to herein, in the context of a fusion protein/polypeptide, as a "fusion partner". A fusion partner may, for example, be selected to assist with the production of the polypeptide(s). Examples of such fusion partners include those capable of enhancing recombinant expression of polypeptide(s) and those capable of facilitating or assisting purification of the polypeptide(s) such as an affinity tag. Alternatively, or in addition, a fusion partner may be selected to increase solubility of the polypeptide(s), to increase the immunogenicity of the polypeptide(s), and/or to enable the polypeptide(s) to be targeted to a specific or desired intracellular compartment.

Methods for the preparation of fusion polypeptides are known in the art and are described, for example, in Ausubel, et al., (eds) (2000-2010), "*Current Protocols in Molecular Biology*", John Wiley & Sons, Inc., New York (see Chapter 16: "*Protein Expression*"). Typically, a fusion polypeptide may be made by standard techniques such as chemical conjugation, peptide synthesis or recombinant means. A fusion polypeptide may include one or more linker(s), such as peptide linker(s), between component parts of the protein, such as between one or more component peptides, and/or between one or more fusion partners and/or component peptides. Such peptide linker(s) may be chosen to permit the component parts of the fusion polypeptide to maintain or attain appropriate secondary and tertiary structure.

Polypeptide Variants and Fragments

Polypeptides of the invention may be modified by, for example, the deletion, addition and/or substitution of amino acid(s) that have minimal influence on the immunogenicity, secondary structure and/or hydropathic nature of the polypeptide. In general, the modifications do not substantially compromise the ability of the polypeptide to bind to a given MHC molecule.

Suitable amino acid substitutions include, but are not necessarily limited to, amino acid substitutions known in the art as "conservative". A "conservative" substitution is one in which an amino acid is substituted for another amino acid that has similar properties, such that one skilled in the art of peptide chemistry would expect the biological activity, secondary structure and/or hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his;

and (5) phe, tyr, trp, his. A modified polypeptide of the invention may also, or alternatively, contain non-conservative amino acid changes.

In certain embodiments, a polypeptide of the invention modified by the deletion, addition and/or substitution of amino acid(s) differs from the unmodified sequence by substitution, deletion or addition of five amino acids or fewer, such as by four, or three, or two, or one amino acid(s).

Included within the scope of the invention are variants of polypeptides of the invention. As used herein a polypeptide "variant" refers to a polypeptide with a substantially similar sequence. In general, two sequences are "substantially similar" if the two sequences have a specified percentage of amino acid residues that are the same (percentage of "sequence identity"). Accordingly, a "variant" of a polypeptide sequence of the invention may share at least about 40%, 45%, 50%, 55%, 60%, 65%, 70%, 75%, 80%, 83% 85%, 88%, 90%, 93%, 95%, 96%, 97%, 98% or 99% sequence identity with the reference sequence.

In general, polypeptide sequence variants possess qualitative biological activity in common. Also included within the meaning of the term "variant" are homologues of polypeptides of the invention. A polypeptide homologue is typically from a different species but sharing substantially the same biological function or activity as the corresponding polypeptide disclosed herein. For example, homologues of polypeptides of the invention include, but are not limited to, those from different species of mammals or microorganisms.

Further, the term "variant" also includes analogues of polypeptides of the invention. A polypeptide "analogue" is a polypeptide which is a derivative of a given polypeptide, which derivative comprises addition, deletion, substitution of one or more amino acids, such that the polypeptide retains substantially the same function. As noted above, the term "conservative amino acid substitution" refers to a substitution or replacement of one amino acid for another amino acid with similar properties within a polypeptide chain (primary sequence of a protein).

In certain embodiments, a "variant" of a polypeptide of the invention differs in sequence (from the related polypeptide of the invention) by substitution, deletion or addition of five amino acids or fewer, such as by four, or three, or two, or one amino acid(s).

Also included within the scope of the invention are fragments of polypeptides of the invention. A polypeptide "fragment" is a polypeptide that encodes a constituent or is a constituent of a polypeptide of the invention or a variant thereof. Typically the fragment possesses qualitative biological activity in common with the polypeptide of which it is a constituent. Typically, the polypeptide fragment may be greater than 50 amino acids in length, between about 5 and about 50 amino acid residues in length, between about 5 and about 45 amino acid residues in length, between about 5 and about 40 amino acid residues in length, between about 5 and about 35 amino acid residues in length, between about 5 and about 30 amino acid residues in length, between about 5 and about 25 amino acid residues in length, between about 5 and about 20 amino acid residues in length, between about 5 and about 15 amino acid residues in length, or between about 5 and about 10 amino acid residues in length. In certain embodiments, a fragment of a polypeptide of the invention is 6, 7, 8, 9, 10, 11, 12, 13, 14, 15, 16, 17, 18, 19, 20, 21, 22, 23, 24, 25, or more than 25 amino acid residues in length.

Exemplary Polypeptide Sequences

In certain embodiments, polypeptides of the invention comprise a sequence of at least six amino acid residues.

The sequence may share homology with a polypeptide from an infectious microorganism and a polypeptide of a human lumican polypeptide defined by residues 222-275 of the sequence set forth in SEQ ID NO: 1, or a fragment thereof. The sequence may share at least 50%, 55%, 60%, 65%, 70%, 75%, 80%, 85%, 90%, 95% or 100% sequence homology with a polypeptide of a human lumican polypeptide defined by residues 222-275 of the sequence set forth in SEQ ID NO: 1, or a fragment thereof.

The sequence may share homology with a polypeptide from an infectious microorganism and a polypeptide of a human lumican polypeptide defined by residues 222-247 of the sequence set forth in SEQ ID NO: 1, or a fragment thereof. The sequence may share at least 50%, 55%, 60%, 65%, 70%, 75%, 80%, 85%, 90%, 95% or 100% sequence homology with a polypeptide of a human lumican polypeptide defined by residues 222-247 of the sequence set forth in SEQ ID NO: 1, or a fragment thereof.

The sequence may share homology with a polypeptide from an infectious microorganism and a polypeptide of a human lumican polypeptide defined by residues 222-241 of the sequence set forth in SEQ ID NO: 1, or a fragment thereof. The sequence may share at least 50%, 55%, 60, 65%, 70%, 75%, 80%, 85%, 90%, 95% or 100% sequence homology with a polypeptide of a human lumican polypeptide defined by residues 222-241 of the sequence set forth in SEQ ID NO: 1, or a fragment thereof.

The sequence may share homology with a polypeptide from an infectious microorganism and a polypeptide of a human opticin polypeptide defined by residues 264-315 of the sequence set forth in SEQ ID NO: 30, or a fragment thereof. The sequence may share at least 50%, 55%, 60%, 65%, 70%, 75%, 80%, 85%6, 90%, 95% or 100% sequence homology with a polypeptide of a human opticin polypeptide defined by residues 264-315 of the sequence set forth in SEQ ID NO: 30, or a fragment thereof.

The sequence may share homology with a polypeptide from an infectious microorganism and a polypeptide of a human keratocan polypeptide defined by residues 71-91 of the sequence set forth in SEQ ID NO: 32, or a fragment thereof. The sequence may share at least 50%, 55%, 60%, 65%, 70%, 75%, 80%, 85%. 90%, 95% or 100% sequence homology with a polypeptide of a human keratocan polypeptide defined by residues 71-91 of the sequence set forth in SEQ ID NO: 32, or a fragment thereof.

The polypeptide from an infectious microorganism may comprise the amino acid sequence set forth in any one of SEQ ID NOs: 5-8, SEQ ID NOs: 36-38, or a fragment thereof. The sequence may share at least 50%, 55%6, 60%, 65%, 70%, 75%6, 80%, 85%, 90%, 95% or 100% sequence homology with a polypeptide from an infectious microorganism comprising the amino acid sequence set forth in any one of SEQ ID NOs: 5-8, SEQ ID NOs: 36-38, or a fragment thereof.

The polypeptide may comprise or consist of the amino acid sequence set forth in SEQ ID NO: 2, or a fragment thereof. In certain embodiments, the eighth amino acid (tyrosine) of the sequence set forth in SEQ ID NO: 2 may be substituted with another amino acid. For example, the eighth amino acid (tyrosine) of the sequence set forth in SEQ ID NO: 2 may be substituted with cysteine (SEQ ID NO: 3) or leucine (SEQ ID NO: 4).

The polypeptide may comprise or consist of the amino acid sequence set forth in SEQ ID NO: 34, or a fragment thereof. In certain embodiments, the third amino acid (tyrosine) of the sequence set forth in SEQ ID NO: 34 may be substituted with another amino acid. For example, the third amino acid (tyrosine) of the sequence set forth in SEQ ID NO: 34 may be substituted with cysteine (SEQ ID NO: 39) or leucine (SEQ ID NO: 40).

Certain embodiments of the invention relate to polypeptides comprising one or more fragments of the sequence set forth in SEQ ID NO: 1. A fragment of SEQ ID NO: 1 may comprise, for example, a constituent of SEQ ID NO: 1 comprising residues 224-232, 224-234, 226-234, 227-234, 229-235, 231-241, 236-244, or 235-243.

Certain embodiments of the invention relate to polypeptides comprising one or more fragments or variants of the sequence set forth in SEQ ID NO: 2, SEQ ID NO: 3, SEQ ID NO: 4, or 34. The fragment or variant may comprise or consist of the sequence set forth in any one of SEQ ID NOs: 9-29 or SEQ ID NOs: 39-40.

Certain embodiments of the invention relate to polypeptides comprising or consisting of the amino acid sequence set forth in SEQ ID NO: 31, SEQ ID NO: 35, or a fragment thereof.

Certain embodiments of the invention relate to polypeptides comprising or consisting the amino acid sequence set forth in SEQ ID NO: 33, or a fragment thereof.

Polynucleotides

Also included within the scope of the invention are polynucleotides encoding polypeptides of the invention, and polynucleotides encoding variants and fragments of polypeptides of the invention.

As will be recognized by the skilled artisan, polynucleotides of the invention may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the invention, and a polynucleotide may, but need not, be linked to other molecules and/or support materials. Polynucleotides may comprise a native sequence (i.e. an endogenous sequence that encodes a protein (e.g. an SLRP such as lumican, opticin or keratocan), a protein of an infectious microorganism, or a fragment thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native HSV protein. The effect on the immunogenicity of the encoded polypeptide may generally be assessed as described herein. The term "variants" also encompasses homologous genes of xenogenic origin.

RNA may be derived from RNA polymerase-catalyzed transcription of a DNA sequence. The RNA may be a primary transcript derived from transcription of a corresponding DNA sequence. RNA may also undergo post-transcriptional processing. For example, a primary RNA transcript may undergo post-transcriptional processing to form a mature RNA. Messenger RNA (mRNA) refers to RNA derived from a corresponding open reading frame that may be translated into a protein by the cell. cDNA refers to a double-stranded DNA that is complementary to and derived from mRNA. Sense RNA refers to an RNA transcript that includes the mRNA and so can be translated into protein by the cell. Antisense RNA refers to an RNA transcript that is complementary to all or part of a target primary transcript of mRNA, and may be used to block the expression of a target gene.

The skilled addressee will recognise that RNA and cDNA sequences may be derived using the genetic code. An RNA sequence may be derived from a given DNA sequence by generating a sequence that is complementary to the particular DNA sequence. A complementary DNA (cDNA) sequence may be derived from a DNA sequence by deriving an RNA sequence from the DNA sequence as above, then converting the RNA sequence into a cDNA sequence.

In order to express a desired polypeptide or fusion polypeptide, the polynucleotide sequences encoding the polypeptide, fusion polypeptide, or functional equivalents, may be cloned into an appropriate vector (e.g. an expression a vector which contains the necessary elements for the transcription and translation of the inserted coding sequence). The vector may comprise, for example, a DNA, RNA or complementary DNA (cDNA) sequence. The vector may be a plasmid vector, a viral vector, or any other suitable vehicle adapted for the insertion of foreign sequences, their introduction into cells and the expression of the introduced sequences. Typically the vector is an expression vector and may include expression control and processing sequences such as a promoter, an enhancer, ribosome binding sites, polyadenylation signals and/or transcription termination sequences. The invention also contemplates host cells transformed by such vectors. For example, polynucleotides encoding polypeptides of the invention may be cloned into a vector which is transformed into a bacterial host cell, (e.g. *E. coli*). Methods for the construction of vectors and their transformation into host cells are generally known in the art, and described in, for example. Sambrook et al., (1989), "*Molecular Cloning: A Laboratory Manual*", 2nd ed., Cold Spring Harbor Laboratory Press, Plainview, N.Y.; and, Ausubel et al. (eds), (2000-2010), "*Current Protocols in Molecular Biology*", John Wiley and Sons, Inc., New York.

The invention thus provides vectors (e.g. expression vectors) comprising polynucleotide sequence(s) of the invention. In some embodiments the vector may be an expression vector. The invention also provides methods for the preparation of a polypeptide of the invention, such a method comprising culturing a host cell comprising a polynucleotide or expression vector of the invention under conditions conductive to expression of the encoded polypeptide. In one embodiment, the method further comprises purifying the expressed polypeptide.

Preparation of Polypeptides, Fusion Polypeptides and Polynucleotides

Polypeptides of the invention or fusion proteins/polypeptides comprising polypeptide(s) of the invention may be manufactured using methods known in the art. For example, polypeptides of the invention may be manufactured by conventional methods used in peptide chemistry synthesis such as solid phase peptide synthesis, liquid phase peptide synthesis and recombinant gene technology. It will be understood that amino acid residues of polypeptides of the invention include any and all of their isomers (e.g. D-form, L-form and DL-form).

A polypeptide of the invention or a fusion polypeptide comprising a polypeptide of the invention as a component part thereof may be synthesised by solid phase chemistry techniques (see, for example. Steward et al., (1963), in "*Solid Phase Peptide Synthesis*", H. Freeman Co., San Francisco; Meienhofer, (1973), in "*Hormonal Proteins and Peptides*", volume 2, 46) or by classical solution synthesis (see, for example, Schroder et al. (1965), in "*The Peptides*", volume 1, 72-75, Academic Press (New York). In general, such methods comprise the addition of one or more amino acids or suitably protected amino acids to a growing sequential polypeptide chain on a polymer. Typically, either the amino or carboxyl group of the first amino acid is protected by a suitable protecting group. The protected and/or derivatised amino acid is then either attached to an inert solid support or utilized in solution by adding the next amino acid in the sequence having the complimentary (amino or carboxyl) group suitably protected and under conditions suitable for forming the amide linkage. The protecting group may then be removed from the newly added amino acid residue and the next amino acid (suitably protected) is then added to form a growing polypeptide chain.

A polypeptide of the invention may be produced, for example, by digestion of a protein or larger polypeptide with one or more proteinases such as endoLys-C, endoArg-C, endoGlu-C and *Staphylococcus* V8-protease. The digested peptide fragments can be purified by, for example, high performance liquid chromatographic (HPLC) techniques.

Recombinant polypeptide production techniques will typically involve the cloning of a polynucleotide encoding a polypeptide of the invention into a plasmid for subsequent expression in a suitable microorganism. Suitable methods for the construction of expression vectors or plasmids are described in detail, for example, in standard texts such as Sambrook et al., (1989), "*Molecular Cloning: A Laboratory Manual*", (2nd ed., Cold Spring Harbor Laboratory Press, Plainview, N.Y.; and, Ausubel et al. (eds), (2000-2010), "*Current Protocols in Molecular Biology*", John Wiley and Sons, Inc., New York. Recombinant methods suitable for producing a polypeptide of the invention or a fusion polypeptide comprising a polypeptide of the invention as a component part thereof are described in detail, for example, in standard texts such as Coligan et al., (eds) (2000-2010), "*Current Protocols in Protein Science*", (Chapter 5), John Wiley and Sons, Inc.; and Pharmacia Biotech., (1994), "*The Recombinant Protein Handbook*", Pharmacia Biotech.

Commonly used expression systems that may be used for the production of a polypeptide of the invention or a fusion polypeptide comprising the same include, for example, bacterial (e.g. *E. coli*), yeast (e.g. *Saccharomyces cerevisiae, Aspergillus, Pichia pastorisis*), viral (e.g. baculovirus and vaccinia), cellular (e.g. mammalian and insect) and cell-free systems. Suitable cell-free systems that may be used include, but are not limited to, eukaryotic rabbit reticuloctye, wheat germ extract systems, and the prokaryotic *E. coli* cell-free system (see, for example, Madin et al., *Proc. Natl. Acad. Sci. U.S.A.* 97:559-564 (2000). Pelham and Jackson, *Eur. J. Biochem.,* 67; 247-256 (1976); Roberts and Paterson, *Proc. Natl. Acad Sci.,* 70: 2330-2334 (1973), Zubay, *Ann. Rev. Genet.,* 7: 267 (1973); Gold and Schweiger, *Meth. Enzymol.,* 20: 537 (1971); Lesley et al., *J. Biol. Chem.,* 266(4): 2632-2638 (1991); Baranov et al., *Gene,* 84: 463-466 (1989); and Kudlicki et al., *Analyt. Biochem.,* 206: 389-393 (1992).

Changes to the amino acid sequence of a polypeptide of the invention or a fusion polypeptide comprising a polypeptide of the invention may be affected by standard techniques in the art. For example, amino acid changes may be affected by nucleotide replacement techniques which include the addition, deletion or substitution of nucleotides (conservative and/or non-conservative), under the proviso that the proper reading frame is maintained. Exemplary techniques include random mutagenesis, site-directed mutagenesis, oligonucleotide-mediated or polynucleotide-mediated mutagenesis, deletion of selected region(s) through the use of existing or engineered restriction enzyme sites, and the polymerase chain reaction. Testing the activity of modified polypeptides for the purposes of the invention may be via any one of a number of techniques known to those of skill in the art.

Purification of polypeptides of the invention or a fusion polypeptide comprising the same may be achieved using standard techniques in the art such as those described in Coligan et al., (eds) (2000-2010), "*Current Protocols in Protein Science*". (Chapter 6), John Wiley and Sons, Inc., New York. For example, if the polypeptide is in a soluble state it may be isolated using standard methods such as column chromatography. Polypeptides of the invention may be genetically engineered to contain various affinity tags or carrier proteins that aid purification. For example, the use of histidine and protein tags engineered into an expression vector containing a polynucleotide encoding a polypeptide of the invention may facilitate purification by, for example, metal-chelate chromatography (MCAC) under either native or denaturing conditions. Purification may be scaled-up for large-scale production purposes.

A polypeptide of the invention, or a fusion polypeptide comprising a polypeptide of the invention as a component part thereof may be a soluble polypeptide or soluble fusion polypeptide.

Typically, a polypeptide of the invention is an isolated polypeptide. It will be understood that the term "isolated" in this context means that the polypeptide has been removed from or is not associated with some or all of the other components with which it would be found in its natural state. For example, an "isolated" polypeptide may be removed from other amino acid sequences within a larger polypeptide sequence, or may be removed from natural components such as unrelated proteins. For the sake of clarity, an "isolated" polypeptide also includes a polypeptide which has not been taken from nature but rather has been prepared de novo, such as for example by chemically synthesis and/or by recombinant methods. As described herein an isolated polypeptide of the invention may be included as a component part of a longer polypeptide or fusion polypeptide.

Polynucleotides encoding polypeptides of the invention can be manufactured using standard techniques known in the art such as those described, for example, in Sambrook et al. (1989) "*Molecular Cloning: A Laboratory Manual*", (2nd ed., Cold Spring Harbor Laboratory Press, Plainview, N.Y.; Itakura K. et al. (1984), "*Synthesis and use of synthetic oligonucleotides*", Annu. Rev. Biochem. 53:323; Innis et al., (eds), (1990), "*PCR Protocols: A Guide to Methods and Applications*", Academic Press, New York; Innis and Gelfand, (eds), (1995), "*PCR Strategies*", Academic Press, New York; and Innis and Gelfand, (eds), (1999), "*PCR Methods Manual*", Academic Press, New York.

Polynucleotides encoding polypeptides of the invention may be manufactured, for example, by chemical synthesis techniques including the phosphodiester and phosphotriester methods (see, for example, Narang et al., (1979), "*Improved phosphotriester method for the synthesis of gene fragments*", Meth. Enzymol. 68:90; Brown et al. (1979), "*Chemical Synthesis and Cloning of a Tyrosine tRNA Gene*", Meth. Enzymol. 68:109-151; and U.S. Pat. No. 4,356,270) or the diethylphosphoramidite method (see Beaucage and Caruthers, (1981), "*Deoxynucleotide phosphoramidite*", Tetrahedron Letters, 22:1859-1862). A method for synthesising oligonucleotides on a modified solid support is described in U.S. Pat. No. 4,458,066.

Typically, a polynucleotide of the invention is an isolated polynucleotide. It will be understood that the term "isolated" in this context means that the polynucleotide has been removed from or is not associated with some or all of the other components with which it would be found in its natural state. For example, an "isolated" polynucleotide may be removed from other nucleic acid sequences within a larger nucleic acid sequence, or may be removed from natural components such as unrelated nucleic acids. For the sake of clarity, an "isolated" polynucleotide also includes a polynucleotide which has not been taken from nature but rather has been prepared de novo, such as chemically synthesised and/or prepared by recombinant methods.

Polypeptides of the invention may be modified with lipids, carbohydrates and/or phosphate groups to improve immunogenicity, stability and/or solubility. Capping of polypeptide termini may be used to enhance stability against cellular proteases. Polypeptides of the invention may be modified to induce apoptosis upon interaction with cells using methods known by those of skill in the art.

Antibodies

The invention provides antibodies "binding specifically" to one or more polypeptides of the invention and/or one or more fusion polypeptides of the invention (i.e. antibodies "specific for" one or more polypeptides/fusion polypeptides of the invention). By "binding specifically" or "specific for" it will be understood that the antibody is capable of binding to a target polypeptide of the invention with a significantly higher affinity than it binds to an unrelated molecule (e.g. a non-target polypeptide). Accordingly, an antibody that binds specifically to a polypeptide of the invention is an antibody with the capacity to discriminate between that polypeptide and any other number of potential alternative binding partners. Accordingly, when exposed to a plurality of different but equally accessible molecules as potential binding partners, an antibody specific for a target polypeptide of the invention will selectively bind to the target polypeptide and other alternative potential binding partners will remain substantially unbound by the antibody. In general, an antibody specific for a target polypeptide of the invention will preferentially bind to the target polypeptide at least 10-fold, preferably 50-fold, more preferably 100-fold, and most preferably greater than 100-fold more frequently than other potential binding partners that are not target polypeptides. An antibody specific for a polypeptide of the invention may be capable of binding to other non-target molecules at a weak, yet detectable level. This is commonly known as background binding and is readily discernible from target polypeptide-specific binding, for example, by use of an appropriate control.

Reaction conditions (e.g. concentration of antibody, incubation time, pH, temperature etc) to facilitate binding of antibodies to polypeptides of the invention will in depend primarily on the antibody utilised and the specific target polypeptide, and may be readily determined using methods known in the art (see, for example, Ausubel et al., (eds), (2000-2010), "*Current Protocols in Molecular Biology*", Vol. 1, John Wiley & Sons, Inc., New York; Coligan et al., (eds). (2000-2010), "*Current protocols in Immunology*", John Wiley and Sons, Inc.; and Bonifacino et al., (eds) (2000-2010), "*Current protocols in Cell Biology*", John Wiley and Sons, Inc.).

Antibodies capable of binding specifically to a polypeptide of the invention can be generated using methods known in the art.

For example, a monoclonal antibody specific for a target polypeptide of interest, typically containing Fab portions, may be prepared using the hybridoma technology described in Harlow and Lane (eds), (1988), "*Antibodies—A Laboratory Manual*", Cold Spring Harbor Laboratory, N.Y.

In essence, in the preparation of monoclonal antibodies directed toward a target polypeptide, any technique that provides for the production of antibodies by continuous cell lines in culture may be used. These include the hybridoma technique originally developed by Kohler et al., (1975), "*Continuous cultures of fused cells secreting antibody of predefined specificity*". Nature, 256:495-497, as well as the trioma technique, the human B-cell hybridoma technique (see Kozbor et al., (1983), "*The Production of Monoclonal Antibodies From Human Lymphocytes*", Immunology Today, 4:72-79), and the EBV-hybridoma technique to produce human monoclonal antibodies (see Cole et al., (1985), in "*Monoclonal Antibodies and Cancer Therapy*", 77-96, Alan R. Liss, Inc.). Immortal, antibody-producing cell lines can be created by techniques other than fusion, such as direct transformation of B lymphocytes with oncogenic DNA, or transfection with Epstein-Barr virus (see, for example, Schreier et al., (1980). "*Hybridoma Techniques*", Cold Spring Harbor Laboratory; Hammerling et al., (1981), "*Monoclonal Antibodies and T-cell Hybridomas*", Elsevier/North-Holland Biochemical Press. Amsterdam; and Kennett et al., (1980) "*Monoclonal Antibodies*", Plenum Press).

In summary, a means of producing a hybridoma from which the monoclonal antibody is produced, a myeloma or other self-perpetuating cell line is fused with lymphocytes obtained from the spleen of a mammal hyperimmunised with a recognition factor-binding portion thereof, or recognition factor, or an origin-specific DNA-binding portion thereof. Hybridomas producing a monoclonal antibody specific for a polypeptide of the invention are identified by their ability to immunoreact with the antigens present in that polypeptide.

A monoclonal antibody specific for a polypeptide of the invention can be produced by initiating a monoclonal hybridoma culture comprising a nutrient medium containing a hybridoma that secretes antibodies of the appropriate antigen specificity. The culture is maintained under conditions and for a time period sufficient for the hybridoma to secrete the antibody molecules into the medium. The antibody-containing medium is then collected. The antibody molecules can then be further isolated using known techniques.

Similarly, there are various procedures known in the art which may be used for the production of polyclonal antibodies. For the production of polyclonal antibodies specific for a polypeptide of the invention, various host animals can be immunized by injection with the polypeptide including, but not limited to, rabbits, chickens, mice, rats, sheep, goats, etc. Further, the polypeptide can be conjugated to an immunogenic carrier (e.g. bovine serum albumin (BSA) or keyhole limpet hemocyanin (KLH)). Also, various adjuvants may be used to increase the immunological response including, but not limited to, Freund's (complete and incomplete), mineral gels such as aluminium hydroxide, surface active substances such as rysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

Screening for the desired antibody can also be accomplished by a variety of techniques known in the art. Suitable assays for immunospecific binding of antibodies include, but are not limited to, radioimmunoassays. ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, immunoelectrophoresis assays, and the like (for description of such techniques see, for example, Ausubel et al., (eds), (2000-2010), "*Current Protocols in Molecular Biology*", Vol. 1, John Wiley & Sons, Inc., New York). Antibody binding may be detected by virtue of a detectable label on the primary antibody. Alternatively, the antibody may be detected by virtue of its binding with a secondary antibody or reagent which is appropriately labelled. A variety of methods for detecting binding events in an immunoassay are known in the art, and are included in the scope of the invention.

In terms of obtaining a suitable amount of an antibody according to the invention, one may manufacture the antibodies using batch fermentation with serum free medium. After fermentation the antibody may be purified via a multistep procedure incorporating chromatography and viral inactivation/removal steps. For instance, the antibody may be first separated by Protein A affinity chromatography and then treated with solvent/detergent to inactivate any lipid enveloped viruses. Further purification, typically by anion and cation exchange chromatography, may be used to remove residual proteins, solvents/detergents and nucleic acids. The purified antibody may be further purified and formulated into 0.9% saline using gel filtration columns. The formulated bulk preparation may then be sterilised and viral filtered and dispensed.

Pharmaceutical Compositions

The invention provides pharmaceutical compositions comprising one or more polypeptide(s) of the invention and/or one or more fusion polypeptides/protein(s) comprising one or more polypeptide(s) of the invention. Accordingly, a pharmaceutical composition of the invention may comprise any one or more polypeptide(s) of the invention and/or any one or more polypeptide(s) of the invention as described above in the section above entitled "Polypeptides and Polynucleotides".

Additionally or alternatively, a pharmaceutical composition of the invention may comprise an antibody specific for a polypeptide of the invention and/or an antibody specific for a fusion polypeptide of the invention (see subsection above entitled "Antibodies").

Additionally or alternatively, a pharmaceutical composition of the invention may comprise a polynucleotide of the invention, a vector comprising a polynucleotide of the invention, and/or a host cell comprising a vector of the invention (see section above entitled "Polypeptides and Polynucleotides").

A pharmaceutical composition of the invention may comprise a pharmaceutically acceptable carrier, adjuvant and/or diluent. The carriers, diluents and adjuvants must be "acceptable" in terms of being compatible with the other ingredients of the composition, and are generally not deleterious to the recipient thereof. Non-limiting examples of pharmaceutically acceptable carriers or diluents are demineralised or distilled water; saline solution; vegetable based oils such as peanut oil, safflower oil, olive oil, cottonseed oil, maize oil; sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from about 10% to about 99.9% by weight of the compositions.

Additionally or alternatively, a pharmaceutical composition of the invention may comprise an immunosuppressive agent, non-limiting examples of which include anti-inflammatory compounds, bronchodilatory compounds, cyclosporines, tacrolimus, sirolimus, mycophenolate mofetil, methotrexate, chromoglycalates, theophylline, leukotriene antagonist, and antihistamine, and combinations thereof. The immunosuppressive agent may also be an immunosuppressive drug or a specific antibody directed against B or T lymphocytes, or surface receptors that mediate their activation. For example, the immunosuppressive drug may be cyclosporine, tacrolimus, sirolimus, mycophenolate mofetil, methotrexate, chromoglycalates, theophylline, leukotriene antagonist, and antihistamine, or a combination thereof.

Additionally or alternatively, a pharmaceutical composition of the invention may comprise a steroid, such as a corticosteroid.

A pharmaceutical composition of the invention may be in a form suitable for administration by injection, in a form of a formulation suitable for oral ingestion (such as capsules, tablets, caplets, elixirs, for example), in a form of an ointment, cream or lotion suitable for topical administration, in a form suitable for delivery as an eye drop, in an aerosol form suitable for administration by inhalation, such as by intranasal inhalation or oral inhalation, or in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl stearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton. Pa.

Topical formulations of the invention may comprise an active ingredient together with one or more acceptable carriers, and optionally any other therapeutic ingredients. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil, wool fat or its derivatives, or a fatty acid such as stearic or oleic acid together with an alcohol such as propylene glycol or macrogols.

A pharmaceutical composition of the invention may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

A pharmaceutical composition of the invention may be administered in the form of a liposome. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to Prescott, (Ed), (1976). "*Methods in Cell Biology*", Volume XIV, Academic Press, New York, N.Y. p. 33 et seq.

A pharmaceutical composition of the invention may be a vaccine. Polypeptide vaccines provide a number of advantages over other vaccine types including an absence of infectious materials that can compromise efficacy and/or trigger undesirable immune responses.

A vaccine of the invention may be administered to naïve recipients (i.e. individuals seronegative for particular infectious microorganism(s) associated with the onset of spondyloarthropathies), or primed recipients (i.e. individuals seropositive for particular infectious microorganism(s) associated with the onset of HLA-associated autoimmune diseases such as spondyloarthropathies and anterior uveitis).

A vaccine of the invention may be a preventative vaccine (i.e. a vaccine administered for the purpose of preventing HLA-associated autoimmune diseases) or a therapeutic vaccine (i.e. a vaccine administered for the purpose of treating HLA-associated autoimmune diseases). A vaccine of the invention may therefore be administered to a recipient for prophylactic, ameliorative, palliative, or therapeutic purposes.

Non-limiting examples of applicable HLA-associated autoimmune diseases include anterior uveitis (e.g. anterior acute uveitis) and spondyloarthropathies including ankylosing spondylitis, psoriatic arthritis, undifferentiated spondyloarthropathy, juvenile onset spondyloarthropathy, enteropathic arthritis, arthritis mutilans, reactive arthritis (Reiter's syndrome), reactive arthritides, sacroiliitis, spondylitis of inflammatory bowel disease, Crohn's disease associated with spondyloarthropathy, whipple disease, and Behcet disease.

A vaccine of the invention may be prepared according to standard methods known to those of ordinary skill in the art.

Methods for vaccine preparation are generally described in Voller et al., (1978), "*New Trends and Developments in Vaccines*", University Park Press, Baltimore, Md., USA.

A vaccine of the invention may comprise an adjuvant. The adjuvant will preferably enhance an immune response induced and/or enhance the specific vaccine, thereby improving protective efficacy. In certain embodiments the adjuvant will enable the induction of protective immunity utilising a lower dose of a polypeptide of the invention in the vaccine. A vaccine of the invention may comprise an adjuvant such as, for example, those described in the subsection above entitled "Pharmaceutical compositions". A suitable adjuvant may be included in a vaccine of the invention in any suitable form (e.g. a powder, a solution, a non-vesicular solution, or a suspension).

Non-limiting examples of adjuvants suitable for inclusion in vaccines of the invention include those described in the section above entitled "Pharmaceutical compositions". Further description regarding suitable adjuvants and methods for the preparation of vaccines are provided in "*Vaccine Adjuvants: Preparation Methods and Research Protocols (Methods in Molecular Medicine)*", (2000), Ohagan (ed), Humana Press Inc.

Any suitable adjuvant may be included in a vaccine of the invention. For example, an aluminium-based adjuvant may be utilised. Suitable aluminium-based adjuvants include, but are not limited to, aluminium hydroxide, aluminium phosphate and combinations thereof. Other specific examples of aluminium-based adjuvants that may be utilised are described in European Patent No. 1216053 and U.S. Pat. No. 6,372,223. Additional non-limiting examples include polypeptide adjuvants such as interferons, interleukins, and other cytokines; AMPHIGEN, oil-in-water and water-in-oil emulsions; and saponins such as QuilA. Oil in water emulsions are well known in the art. In general, the oil in water composition will comprise a metabolizable oil, for example, a fish oil, a vegetable oil, or a synthetic oil. Examples of suitable oil in water emulsions include those described in European Patent No. 0399843, U.S. Pat. No. 7,029,678 and PCT publication No. WO 2007/006939. The oil in water emulsion may be utilised with other adjuvants and/or immunostimulants.

Other non-limiting examples of other suitable adjuvants include immunostimulants such as granulocyte-macrophage colony-stimulating factor (GM-CSF), monophosphoryl lipid A (MPL), cholera toxin (CT) or its constituent subunit, heat labile enterotoxin (LT) or its constituent subunit, toll like receptor ligand adjuvants such as lipopolysaccharide (LPS) and derivatives thereof (e.g. monophosphoryl lipid A and 3-Deacylated monophosphoryl lipid A), muramyl dipeptide (MDP), and F protein of Respiratory Syncytial Virus (RSV).

A vaccine of the present invention may be administered to a recipient in isolation or in combination with other additional therapeutic agent(s). In embodiments where the vaccine is administered with other additional therapeutic agent(s), the administration may be simultaneous, or may be sequential (i.e. vaccine administration followed by administration of the agent(s) or vice versa).

Prevention and Treatment of HLA-Associated Autoimmune Diseases

The invention provides methods for the prevention or treatment of an HLA-associated autoimmune disease comprising administering to a subject one or more polypeptides of the invention. The HLA-associated autoimmune disease may be an HLA-B27-associated autoimmune disease. In certain embodiments, the disease is a spondyloarthropathy or anterior uveitis.

Polypeptides of the invention may be administered to a subject in the form of a pharmaceutical composition of the invention (see section above entitled "Pharmaceutical compositions"). The pharmaceutical composition may be a preventative or therapeutic vaccine.

Preferably, the subject is a human. In certain embodiments, the human subject is positive for HLA-B27. The human subject may be homozygous or heterozygous for HLA-B27.

In alternative embodiments of the invention, the subject is a non-human mammal (e.g. a bovine, equine, ovine, non-human primate, or rodent species) and the autoimmune disease is an MHC-associated autoimmune disease. In certain embodiments, the disease is an MHC-associated spondyloarthropathy or anterior uveitis.

As discussed in detail above, polypeptides of the invention comprise region(s) of sequence homology with proteins derived from infectious microorganisms and SLRPs (e.g. lumican, opticin, keratocan) of host organisms susceptible to infection by those microorganisms. Without being restricted to particular mode(s) of action, it is proposed that administration of polypeptides of the invention to a subject may affect the immune response in several ways.

For example, administration of polypeptides of the invention to a subject may prime the immune system against infection by pathogenic microorganisms (e.g. bacteria and/or fungi) having protein(s) that share sequence homology with the administered polypeptides (i.e. induction of immunological memory). Priming of the host immune response may serve to prevent significant infection/re-infection of the host by said microorganisms. Preventing the chronic exposure of host immune cells (e.g. $CD8^+$ T lymphocytes) to antigenic determinants of infectious microorganisms sharing similarities with a host SLRP (e.g. lumican, opticin, keratocan) may assist in preventing the development of autoreactive immune cells that target and destroy cells and tissues expressing the SLRP.

Additionally or alternatively, administration of polypeptides of the invention to a subject may assist in re-inducing tolerance to antigenic determinants present in host SLRPs (e.g. lumican, opticin, keratocan). For example, administration of polypeptides of the invention comprising sequence motifs homologous to antigenic determinants of a host SLRP protein (e.g. lumican, opticin, keratocan) recognised by autoreactive immune cells and antibodies may induce tolerance to those determinants such that host SLRP is no longer recognised.

The methods of the invention may be used to prevent or treat an HLA-associated autoimmune disease. The HLA-associated autoimmune disease may be an HLA-B27-associated autoimmune disease. In certain embodiments, the disease is a spondyloarthropathy or anterior uveitis.

Non-limiting examples of spondyloarthropathies that may be treated and/or prevented using the methods of the invention include ankylosing spondylitis, psoriatic arthritis, undifferentiated spondyloarthropathy, juvenile onset spondyloarthropathy, enteropathic arthritis, arthritis mutilans, reactive arthritis (Reiter's syndrome), reactive arthritides, sacroiliitis, spondylitis of inflammatory bowel disease, Crohn's disease associated with spondyloarthropathy, whipple disease, and Behcet disease.

Non-limiting examples of anterior uveitis that may be treated and/or prevented using the methods of the invention include anterior acute uveitis and anterior chronic uveitis.

Although anterior uveitis and spondyloarthropathies such as those referred to above may be associated with the expression of HLA-B27 in humans, it will be understood that application of the methods provided herein are not limited to the prevention or treatment of autoimmune disease(s) in HLA-B27 positive subjects.

Accordingly, methods of the invention may be used for the prevention or treatment of MHC-associated autoimmune disease(s) in subjects of any MHC subtype, including humans of any HLA subtype.

Administration to a subject of a polypeptide, composition or vaccine in accordance with the methods of the invention may be performed by any suitable route including, but not limited to, the parenteral (e.g. intravenous, intradermal, subcutaneous or intramuscular), mucosal (e.g. oral or intranasal) or topical route.

Accordingly, a polypeptide of the invention (or a composition/vaccine comprising the same) may be administered in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, or in a form suitable for parenteral administration, that is, subcutaneous, intramuscular or intravenous injection.

Formulations for intranasal administration may be provided in a freeze-dried powder form, in liquid form as nose drops, spray, or suitable for inhalation, as powder, as cream, or as emulsion.

In one embodiment, a polypeptide of the invention (or a composition/vaccine comprising the same) is provided in an oral form for administration to a subject in accordance with the methods of the invention. Oral administration may assist in methods of treatment designed to re-induce tolerance to antigen(s) present in self proteins sharing sequence homology with those of pathogenic bacterial protein(s).

In certain embodiments, polypeptides of the invention (or a composition/vaccine comprising the same) may be administered with a bio-scaffold.

A polypeptide of the invention (or a composition/vaccine comprising the same) used in the methods of the invention may be administered to a subject therapeutically or preventively.

In a therapeutic application, the polypeptide, composition or vaccine is administered to a subject already suffering from an HLA-associated autoimmune disease (e.g. a spondyloarthropathy or anterior uveitis) in an amount sufficient to cure or at least partially arrest the disease and its complications. Typically, in therapeutic applications, the treatment would be for the duration of the disease state or condition.

In a preventative application, the polypeptide, composition or vaccine is administered to a subject that is not suffering from an HLA-associated autoimmune disease (e.g. a spondyloarthropathy or anterior uveitis) at the time of administration. In particular, it is contemplated that administration of a vaccine of the invention to an individual previously exposed (i.e. primed) to a microorganism with antigenic determinants causative of spondyloarthropathies is beneficial in preventing the emergence of a spondyloarthropathy upon re-exposure of the subject to that microorganism.

The therapeutically effective dose level for any particular subject will depend upon a variety of factors including: the disease being treated and the severity/degree of progression of the disease; the subject's characteristics (e.g. age, body weight, general health, sex and diet of the subject); whether the compound is being used as single agent or combination therapy; the type of MHC restriction of the patient; the time of administration; the route of administration; the rate of sequestration of the polypeptide or composition (including vaccine); the duration of the treatment; the activity of the compound or agent employed; together with other related factors known in the art.

Various general considerations that may be considered when determining an appropriate dosage of a composition of the invention are described, for example, in Gennaro et al. (eds), (1990). "*Remington's Pharmaceutical Sciences*", Mack Publishing Co., Easton, Pa., USA; and Gilman et al., (eds), (1990), "*Goodman And Gilman's: The Pharmacological Bases of Therapeutics*", Pergamon Press.

Further, it will be apparent to one of ordinary skill in the art that the optimal quantity and spacing of individual dosages will be determined by the nature and extent of the spondyloarthropathy being treated, the form, route and site of administration, and the nature of the particular subject being treated.

One skilled in the art would be able, by routine experimentation, to determine an effective, non-toxic amount of a polypeptide, composition or vaccine of the invention which would be required to effectively prevent or treat an applicable spondyloarthropathy.

For example, an optimal dosage may be derived from administering serially diluted preparations comprising a polypeptide, composition or vaccine of the invention in conjunction with a suitable testing procedure. Additionally or alternatively, a matrix comprising various different dosages and dosage frequency can be designed and applied to one or more groups of experimental subjects to determine optimal dosages.

Generally, an effective dosage is expected to be in the range of about 0.0001 mg to about 1000 mg of active agent per kg body weight per 24 hours; typically, about 0.001 mg to about 750 mg of active agent of active agent per kg body weight per 24 hours; about 0.01 mg to about 500 mg of active agent per kg body weight per 24 hours; about 0.1 mg to about 500 mg of active agent per kg body weight per 24 hours; about 0.1 mg to about 250 mg of active agent per kg body weight per 24 hours; or about 1.0 mg to about 250 mg of active agent per kg body weight per 24 hours.

More typically, an effective dose range is expected to be in the range about 1.0 mg to about 200 mg of active agent per kg body weight per 24 hours; about 1.0 mg to about 100 mg of active agent per kg body weight per 24 hours; about 1.0 mg to about 50 mg of active agent per kg body weight per 24 hours; about 1.0 mg to about 25 mg of active agent per kg body weight per 24 hours; about 5.0 mg to about 50 mg of active agent per kg body weight per 24 hours; about 5.0 mg to about 20 mg of active agent per kg body weight per 24 hours; or about 5.0 mg to about 15 mg of active agent per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

In many instances, it will be desirable to have several or multiple administrations of a polypeptide of the invention (or a composition/vaccine comprising the same). For example, administration may occur 1, 2, 3, 4, 5, 6, 7, 8, 9, 10, or more times. The administrations may be from about one to about twelve week intervals, and in certain embodiments from about one to about four week intervals. Periodic re-administration may be desirable in the case of recurrent exposure to a particular infectious microorganism targeted by a composition of the invention.

It will also be apparent to one of ordinary skill in the art that the optimal course of treatment can be ascertained using conventional course of treatment determination tests.

Where two or more therapeutic entities are administered to a subject "in conjunction", they may be administered in a single composition at the same time, or in separate compositions at the same time or in separate compositions separated in time.

The efficacy of methods for preventing or treating diseases referred herein may be determined using standard techniques.

For therapeutic applications, such a determination will generally rely on establishing whether a given disease is cured or at least partially arrested in the treated subject.

For preventative applications, such a determination will generally rely on establishing whether the subject develops a given disease over a relevant time period following treatment, particularly upon re-exposure to microorganisms with antigenic determinants that are associated with spondyloarthropathies.

These factors may be established by clinical examination of the subject for symptoms and manifestations of the disease (e.g. a spondyloarthropathy or anterior uveitis) in question. Additionally or alternatively, diagnostic assays may be performed to detect the presence of absence of autoreactive immune cells and/or antibodies indicative of the disease (e.g. a spondyloarthropathy or anterior uveitis), or the likelihood of developing the disease in question. Non-limiting examples of such diagnostic assays are provided in the section below entitled "Diagnostic and prognostic assays".

Medicaments

Polypeptides, fusion polypeptides/proteins, antibodies, polynucleotides, pharmaceutical compositions and/or vaccines of the invention may be used in the preparation of medicaments for treating or preventing HLA-associated autoimmune diseases. Also provided is use of a polypeptide, fusion polypeptide, antibody, polynucleotide, pharmaceutical composition and/or vaccine of the invention for treating an HLA-associated autoimmune disease.

The HLA-associated autoimmune disease may be an HLA-B27-associated autoimmune disease. In certain embodiments, the disease is a spondyloarthropathy or anterior uveitis.

Non-limiting examples of spondyloarthropathies that may be treated and/or prevented using polypeptides/proteins, antibodies, polynucleotides, pharmaceutical compositions, vaccines, and medicaments of the invention include ankylosing spondylitis, psoriatic arthritis, undifferentiated spondyloarthropathy, juvenile onset spondyloarthropathy, enteropathic arthritis, arthritis mutilans, reactive arthritis (Reiter's syndrome), reactive arthritides, sacroiliitis, spondylitis of inflammatory bowel disease, Crohn's disease associated with spondyloarthropathy, whipple disease, and Behcet disease.

Non-limiting examples of anterior uveitis that may be treated and/or prevented using using polypeptides/proteins, antibodies, polynucleotides, pharmaceutical compositions, vaccines, and medicaments of the invention include anterior acute uveitis and anterior chronic uveitis.

Diagnostic and Prognostic Assays

Polypeptides of the invention may be used in diagnostic and prognostic assays for HLA-associated autoimmune diseases. The HLA-associated autoimmune disease may be an HLA-B27-associated autoimmune disease. In certain embodiments, the disease is a spondyloarthropathy or anterior uveitis.

It has been determined that host immune cells and antibodies directed towards specific antigenic determinants in proteins of infectious microorganisms aberrantly recognise similar or identical antigenic determinants in host SLRPs (e.g. lumican, opticin or keratocan) instigating the destruction of cells and tissues in which those host proteins are expressed. The invention provides specific polypeptide sequences present in host SLRPs (e.g. lumican, opticin or keratocan) that are recognised by these autoreactive immune cells and antibodies, and hence a means of detecting the presence or absence of autoreactive immune cells and antibodies in a given subject.

The diagnostic and prognostic methods of the invention comprise detecting the presence or absence of an immune cell and/or protein specific for one or more polypeptides of the invention in a biological sample derived from a subject. The protein may be an antibody or an antibody fragment.

An immune cell and/or protein "specific for" a polypeptide of the invention will be capable of binding to the polypeptide with a significantly higher affinity than it binds to an unrelated molecule (e.g. another different polypeptide). Accordingly, an immune cell or protein (e.g. an antibody) that binds specifically to a polypeptide of the invention has the capacity to discriminate between that polypeptide and any other number of potential alternative binding partners. Accordingly, when exposed to a plurality of different but equally accessible molecules as potential binding partners, the immune cell or protein specific for a polypeptide of the invention will selectively bind to the polypeptide and other alternative potential binding partners will remain substantially unbound. In general, so an immune cell or protein specific for a polypeptide of the invention will preferentially bind to the polypeptide at least 10-fold, preferably 50-fold, more preferably 100-fold, and most preferably greater than 100-fold more frequently than other potential binding partners. An immune cell or protein specific for a polypeptide of the invention may be capable of binding to other non-target molecules at a weak, yet detectable level. This is commonly known as background binding and is readily discernible from specific binding, for example, by use of an appropriate control.

The presence of an immune cell and/or protein specific for the polypeptide in a biological sample from the subject (i.e. "detecting the presence" of an immune cell and/or protein specific for the polypeptide) is indicative of a positive diagnosis for the HLA-associated autoimmune disease (e.g. an HLA-B27-associated autoimmune disease). In certain embodiments, the disease is a spondyloarthropathy or anterior uveitis.

Alternatively, failure to detect the presence of an immune cell and/or protein specific for the polypeptide in a biological sample from the subject (i.e. "detecting the absence" of an immune cell and/or protein specific for the polypeptide) is indicative of a negative diagnosis for the HLA-associated autoimmune disease (e.g. an HLA-B27-associated autoimmune disease). In certain embodiments, the disease is a spondyloarthropathy or anterior uveitis.

In certain embodiments, the presence of an immune cell and/or antibody specific for a polypeptide of the invention in the biological sample may be used for prognostic purposes. For example, the methods of the invention may be used to quantify the number or proportion of immune cells and/or antibodies specific for the polypeptide in a given biological sample which may be predictive of a particular disease state.

In other embodiments, the presence of an immune cell and/or antibody specific for the polypeptide in the biological sample may be indicative of a predisposition to developing an HLA-associated autoimmune disease in a subject (e.g. an HLA-B27-associated autoimmune disease). The disease may be a spondyloarthropathy or anterior uveitis. For example, the subject may be predisposed to developing the disease upon re-infection by an infectious microorganism that expresses a protein having sequence homology with the polypeptide.

Preferably, the subject is a human. In certain embodiments, the human subject is positive for HLA-B27. The human subject may be homozygous or heterozygous for HLA-B27.

In alternative embodiments of the invention, the subject is a non-human mammal (e.g. a bovine, equine, ovine, non-human primate, or rodent species) and the autoimmune disease is an MHC-associated autoimmune disease. In certain embodiments, the disease is an MHC-associated spondyloarthropathy or anterior uveitis.

The biological sample may be collected from an individual and used directly in the methods of the invention. Alternatively, the biological sample may be processed prior to use in the methods of the invention. For example, the biological sample may be purified, concentrated, separated into various components, or otherwise modified prior to use.

Non-limiting examples of biological samples include whole blood or a component thereof (e.g. plasma, serum), urine, saliva lymph, bile fluid, sputum, tears, cerebrospinal fluid, bronchioalveolar lavage fluid, synovial fluid, semen, ascitic tumour fluid, breast milk and pus.

It will be understood that a biological sample as contemplated herein includes cultured biological materials, including a sample derived from cultured cells, such as culture medium collected from cultured cells or a cell pellet. Accordingly, a biological sample may refer to a lysate, homogenate or extract prepared from a whole organism or a subset of its tissues, cells or component parts, or a fraction or portion thereof. A biological sample may also be modified prior to use, for example, by purification of one or more components, dilution, and/or centrifugation.

In certain embodiments, the diagnostic methods further comprise determining the MHC-type of the subject (e.g. the HLA-type of a human subject). Methods for HLA-typing are known in the art. Non-limiting examples of such methods include those described in U.S. Pat. Nos. 4,582,788, 4,683,202 and 5,545,526.

Diagnostic methods of the invention may be performed by contacting a biological sample from the subject with a polypeptide of the invention (e.g. one or more of those polypeptides referred to in the embodiments listed directly above) and detecting the presence or absence of an immune cell or protein of the biological sample specific for the polypeptide. A subject tested in accordance with the diagnostic methods may be a juvenile. A subject tested in accordance with the diagnostic methods may be a human juvenile positive for HLA-B27. A subject tested in accordance with the diagnostic methods may be an adult human positive for HLA-B27.

In certain embodiments, methods for determining a predisposition towards developing an HLA-associated autoimmune disease (e.g. a spondyloarthropathy or anterior uveitis) in a subject may be performed by contacting a biological sample from the subject with a polypeptide of the invention (e.g. one or more of those polypeptides referred to in the embodiments listed directly above) and detecting the presence or absence of an immune cell or protein of the biological sample specific for said polypeptide. A subject tested in accordance with the methods may be a juvenile. A subject tested in accordance with the methods may be a human juvenile positive for HLA-B27. A subject tested in accordance with the methods may be an adult human positive for HLA-B27. A subject tested in accordance with the methods will generally not be exhibiting symptoms of a spondyloarthropathy at the time of testing. However, in some circumstances the subject may be exhibiting mild symptoms of the spondyloarthropathy at the time of testing. In certain embodiments, the subject is a primed recipient (i.e. an individual seropositive for particular infectious microorganism(s) associated with the onset of spondyloarthropathies.

Non-limiting examples of immune cells of the sample specific for a polypeptide of the invention detectable by the methods include $CD4^+T$ lymphocytes, $CD8^+T$ lymphocytes and B lymphocytes.

Non-limiting examples of proteins of the sample specific for a polypeptide of the invention detectable by the methods include antibodies.

Reaction conditions (e.g. concentration of polypeptides, incubation time, pH, temperature etc) to facilitate binding of immune cells and proteins (e.g. antibodies) to polypeptides of the invention may be readily determined using methods known in the art (see, for example, Ausubel et al., (2000-2010), "*Current Protocols in Molecular Biology*", Vol. 1, John Wiley & Sons, Inc., New York; Coligan et al. (eds), (2000-2010), "*Current protocols in Immunology*", John Wiley and Sons, Inc.; and Bonifacino et al. (eds) (2000-2010), "*Current protocols in Cell Biology*", John Wiley and Sons, Inc.).

In certain embodiments, the diagnostic methods involve detecting the binding of a polypeptide of the invention to an antibody present in a sample derived from a given subject. Accordingly, antibodies detectable by the methods are specific for a polypeptide of the invention. The antibody may be a human antibody. The human antibody may be of the isotype IgG (including IgG1, IgG2, IgG3 and IgG4 subisotypes), IgA (including IgA1 and IgA2 subisotypes), IgD, IgE, or IgM.

Antibodies specific for polypeptides of the invention may be detected using any method known in the art. Suitable examples of such methods include, but are not limited to, immunoblotting, enzyme-linked immunosorbent assay (ELISA), Western blotting, immunohistochemistry, immunocytochemistry, antibody-affinity chromatography, and variations/combinations thereof (see, for example, Coligan et al. (eds), (2000-2010). "*Current protocols in Immunology*", John Wiley and Sons, Inc.).

For example, antibodies may be isolated and/or detected by immobilising a polypeptide (or a combination of polypeptides) of the invention onto a support, contacting the polypeptide immobilised on the support with a biological sample (e.g. purified peripheral blood mononuclear cells (PBMCs) or whole blood) under conditions suitable for binding to occur between antibodies within the sample and the immobilised polypeptide, then rinsing the support with a suitable reagent to remove unbound sample. The polypeptide may be immobilised on the support by direct binding or be bound indirectly to the support via one or more additional compounds. Non-limiting examples of suitable supports include assay plates (e.g. microtitre plates) or test tubes manufactured from polyethylene, polypropylene, polystyrene, sephadex, polyvinyl chloride, membranes (e.g. nitrocellulose membranes), beads/discs (including magnetic beads and discs) and particulate materials such as filter paper, nitrocellulose membrane, agarose, cross-linked dextran, and other polysaccharides.

In certain embodiments of the invention, the detection of an antibody bound to a polypeptide of the invention is performed using a detectable reagent capable of binding to the antibody. The reagent may bind to any region of the antibody including, but not limited to, the heavy chain, light chain, complementarity determining regions (CDRs), Fv, Fab or Fc regions. The reagent may be capable of binding to multiple regions of the antibody.

In one embodiment, the detectable reagent capable of binding to the antibody is a secondary antibody or an antigen-binding fragment thereof. Preferably, the secondary antibody is specific for a human antibody isotype. The human antibody isotype may be IgG (including IgG1, IgG2, IgG3 and IgG4 subisotypes), IgA (including IgA1 and IgA2 subisotypes), IgD, IgE, or IgM.

The secondary antibody may be conjugated to a detectable label, such as a fluorophore, enzyme, chromogen, catalyst, or direct visual label. Suitable enzymes for use as detectable labels on antibodies as contemplated herein include, but are not limited to, alkaline phosphatase and horseradish peroxidase, and are also described, for example, in U.S. Pat. Nos. 4,849,338 and 4,843,000. The enzyme label may be used alone or in combination with additional enzyme(s) in solution.

Methods for the generation of suitable secondary antibodies will be readily apparent to those skilled in the art and are described under the section above entitled "Antibodies".

The detection of antibodies bound to a polypeptide of the invention may be performed as an enzyme-linked immunosorbent assay (ELISA). In general, the assay involves the coating of a polypeptide of the invention (a "capture reagent") onto a solid support, such as the wells of a microtitre plate or a column, manufactured from a material such as polyethylene, polypropylene, polystyrene etc.

The polypeptide may be linked to the surface of the support, for example, by a non-covalent or covalent interaction or a physical linkage. Specific examples of methods for attachment of the capture reagents to supports are described in U.S. Pat. No. 4,376,110. If a covalent linkage is used, the cross-linking agent may be utilised to attach the capture reagent to the support (e.g. glutaraldehyde, N-hydroxy-succinimide esters, bifunctional maleimides).

The support may be treated with a blocking agent (e.g. non-fat milk, bovine serum albumin, casein, egg albumin) to prevent unwanted binding of material to excess sites on the surface of the support.

The sample may be administered to the surface of the support following coating and blocking. In general, the sample is diluted to an appropriate level using a suitable buffer. The degree of sample dilution and selection of an appropriate buffer will depend on factors such as the sample under analysis and the type of support utilised in the assay. These can be determined without inventive effort by those of ordinary skill in the art.

Once applied to the support coated with a polypeptide of the invention, the sample is generally incubated under conditions suitable to maximize sensitivity of the assay and to minimize dissociation. The incubation may be performed at a generally constant temperature, ranging from about 0° C. to about 40° C., and preferably ranging from about 20° C. to about 30° C. The pH of the incubation mixture will generally be in the range of about 4 to about 10, preferably in the range of about 6 to about 9, and more preferably in the range of about 7 to about 8. Various buffers may be employed to achieve and maintain the target pH during the incubation, non-limiting examples of which include Tris-phosphate, Tris-HCl borate, phosphate, acetate and carbonate. The incubation time is generally associated with the temperature, and will in general be less than about 12 hours to avoid non-specific binding. Preferably, the incubation time is from about 0.5 hours to about 3 hours, and more preferably from about 0.5 hours to about 1.5 hours at room temperature.

Following incubation, the sample may be removed from the immobilised polypeptide on the support, for example, by washing/rinsing the support. The pH of a suitable washing buffer will, in general, be in the range of about 6 to about 9 and preferably in the range of about 7 to about 8. The washing/rinsing may be done three or more times. The washing/rinsing may be performed using wash buffer generally at a temperatures from about 0° C. to about 40° C., and preferably from about 4° C. to about 30° C.

In a subsequent step, immobilised antibodies from the sample bound to polypeptides of the invention (on the support) are contacted with a detection reagent. Preferably, immobilised antibodies are contacted with a detection reagent at a temperature of about 20° C. to about 40° C., and preferably at a temperature of about 20° C. to about 25° C. In one embodiment, immobilised antibodies are contacted with a detection reagent at room temperature (RT) for about one hour. The detection reagent may be an antibody. In applications where the detectable reagent is an antibody, a molar excess of the antibody with respect to the maximum concentration of the molecules of the sample immobilised on the support is preferable. The antibody may be directly or indirectly detectable. The antibody may have a colorimetric label or a fluorometric label.

An additional antibody may be applied that binds to the detection reagent. The additional antibody may have a colorimetric label or a fluorometric label.

Determination of the presence and amount of an antibody bound to a polypeptide of the invention can be achieved using methods known in the art, and will depend upon the detection reagent utilised. For example, detection may include colourimetry, chemiluminescence, or fluorometry. Detection and quantitative measurements may be conducted based on the signal derived from the detection reagent(s) compared to background signal derived from control samples. A standard curve may be generated to assist in determining the concentration of a polypeptide of the invention in a given sample.

In certain embodiments, the methods involve detecting the binding of a polypeptide of the invention to an immune cell present in a sample derived from a given subject.

Accordingly, immune cells detectable by the methods are specific for a polypeptide of the invention. In general, the immune cell will be specific for one or more antigenic determinants present in the polypeptide. Non-limiting examples of immune cells that may be specific for a polypeptide of the invention include $CD4^+T$ lymphocytes, $CD8^+T$ lymphocytes and B lymphocytes.

Immune cells specific for polypeptides of the invention may be detected using methods known in the art.

In general, the detection of antigen-specific T cells will require presentation of a polypeptide of the invention on MHC molecules. This may be achieved using tetramer-based assays. Alternatively, antigen-specific T cells in a given biological sample may be detected by exposing the sample to a polypeptide of the invention and measuring indicators of antigen-specific T cell activation (e.g. cell proliferation, cytokine secretion and/or cell surface expression of activation markers).

For example, a polypeptide of the invention or a combination of polypeptides of the invention may be mixed with a biological sample (e.g. purified peripheral blood mononuclear cells (PBMCs) or whole blood). The mixture may then be incubated for a suitable time period (e.g. 4-12 hours at 37° C.) facilitating the stimulation of immune cells that are specific for the polypeptide(s).

Immune cells specific for the polypeptide(s) may then be detected and/or enumerated using techniques known in the art. For example, the detection of immune cells specific for the polypeptide(s) may be performed by enzyme-linked immunosorbent assay (ELISA), analysing immune cell proliferation, analysing cytokine synthesis of immune cells, and/or analysing immune cell surface marker expression (such as by flow cytometry, ELISPOT, or other assays).

For example, immune cells specific for the polypeptide(s) may be detected and/or enumerated by measuring the expression of cellular activation markers (e.g. IFN-γ, IL-2, HLA-DR. CD25, CD69, CD38 and the like) by immune cells of the sample. In general, the detection of an upregulation in the expression of such activation markers in a subset of immune cells within the total cell population of the sample is indicative of the presence of immune cells specific for polypeptide(s) of the invention. Suitable controls (e.g. LPS stimulation) may be used to verify the integrity of such experiments.

The expression of cellular activation markers may be assessed by flow cytometry. The general principles of flow cytometry are known in the art, and assays for the preparation of cells for flow cytometry are described, for example, in Robinson et al., (eds), (2000-2010), "*Current Protocols in Cytometry*", John Wiley and Sons, Inc.; Coligan et al., (eds) (2000-2010), "*Current protocols in Immunology*", John Wiley and Sons. Inc.; U.S. Pat. Nos. 4,727,020, 4,704,891 and 4,599,307.

Additionally or alternatively, immune cells specific for polypeptide(s) of the invention may be detected by the identification and enumeration of cytokine-producing cells in the sample following stimulation. Suitable assays for achieving this purpose include ELISA-based assays (e.g. ELISPOTs).

Additionally or alternatively, immune cells specific for polypeptide(s) of the invention may be detected by measuring cell proliferation following stimulation of immune cells in the sample.

For example, the proliferation of immune cells specific for the polypeptide(s) may be assessed using a fluorescent dye assay. Fluorescent dye assays are well known in the art, and are described, for example in Parish C R *Immunol Cell Biol.*, (1999), 77(6):499-508; Lyons A B and Parish C R, *Journal of Immunological Methods.*, (1994), 171:131-137; Horan et al., *Methods in Cell Biology*, (1990), 33:460-490; Lyons A B, *J Immunol Methods*, (2000), 21:243(1-2):147-54; Quah et al., *Nat Protoc.* (2007), 2(9):2049-56; Robinson et al. (2000-2010) (eds), "*Current Protocols in Cytometry*". John Wiley and Sons, Inc., (see for example pp 9.11.1-9.11.9); Traycoff et al., *Blood*, (1995) 85:2059-2068; Young et al., *Blood*, (1996), 87; 545-556; Gothot et al. *Experimental Hematology* (1998), 26:562-570; Glimm and Eaves, *Blood*, (1999), 94:2161-2168, and Oostendorp et al., *Blood*, (2000), 95:855-862.

The skilled addressee will recognise that the methods for detecting and/or enumerating immune cells and proteins (e.g. antibodies) specific for polypeptide(s) of the invention described herein are non-limiting examples and other suitable methods known in the field may be utilised.

Kits

The invention provides kits for the diagnosis and prognosis of an HLA-associated autoimmune disease (e.g. an HLA-B27-associated autoimmune disease). In certain embodiments, the disease is a spondyloarthropathy or anterior uveitis. Kits of the invention may be fragmented kits. The kits comprise one or more polypeptides of the invention.

In certain embodiments, kits are provided for determining a predisposition towards developing an HLA-associated autoimmune disease (e.g. an HLA-B27-associated autoimmune disease). In certain embodiments, the disease is a spondyloarthropathy or anterior uveitis.

The kits may be used for the detection of an immune cell and/or protein specific for one or more polypeptide(s) of the invention in a biological sample. The protein may be an antibody or an antibody fragment. The immune cell may be a lymphocyte (e.g. a CD4$^+$T lymphocyte, a CD8$^+$T lymphocyte or a B lymphocyte).

Detection of the presence of an immune cell and/or protein in a sample specific for a polypeptide of the invention utilising a kit provided herein is indicative of a positive diagnosis for an HLA-associated autoimmune disease (e.g. an HLA-B27-associated autoimmune disease). In certain embodiments, the disease is a spondyloarthropathy or anterior uveitis.

Alternatively, failure to detect the presence of an immune cell and/or protein specific for a polypeptide of the invention utilising a kit provided herein is indicative of a negative diagnosis for an HLA-associated autoimmune disease (e.g. an HLA-B27-associated autoimmune disease). In certain embodiments, the disease is a spondyloarthropathy or anterior uveitis.

In certain embodiments, a kit of the invention may be used for prognostic purposes. For example, the kit may be used to quantify the number or proportion of immune cells and/or antibodies specific for a polypeptide of the invention in the sample of a subject which may be predictive of a particular disease state.

In other embodiments, the presence of an immune cell and/or antibody specific for the polypeptide in the sample may be indicative of a predisposition to developing an HLA-associated autoimmune disease in a subject (e.g. a spondyloarthropathy or anterior uveitis), for example, upon re-infection by an infectious microorganism containing a protein sharing sequence homology with a polypeptide of the invention.

A subject tested using a kit of the invention may be a human. In certain embodiments, the human subject is positive for HLA-B27. The human subject may be homozygous or heterozygous for HLA-B27. A subject tested using a kit of the invention may be a juvenile.

A subject tested using a kit of the invention may be a human juvenile positive for HLA-B27.

A subject tested using a kit of the invention may be an adult human positive for HLA-B27.

In alternative embodiments, a subject tested using a kit of the invention is a non-human mammal (e.g. a bovine, equine, ovine, non-human primate, or rodent species), and the kit is used for the diagnosis and/or prognosis of an MHC-associated autoimmune disease. In certain embodiments, the disease is an MHC-associated spondyloarthropathy or anterior uveitis.

The sample will generally be a biological sample. Non-limiting examples of biological samples include whole blood or a component thereof (e.g. plasma, serum), urine, saliva lymph, bile fluid, sputum, tears, cerebrospinal fluid, bronchioalveolar lavage fluid, synovial fluid, semen, ascitic tumour fluid, breast milk and pus.

It will be understood that a biological sample as contemplated herein includes cultured biological materials, including a sample derived from cultured cells, such as culture medium collected from cultured cells or a cell pellet. Accordingly, a biological sample may refer to a lysate, homogenate or extract prepared from a whole organism or a subset of its tissues, cells or component parts, or a fraction or portion thereof. A biological sample may also be modified prior to use, for example, by purification of one or more components, dilution, and/or centrifugation.

It will be understood that different combinations of polypeptides of the invention (e.g. two or more of those polypeptides referred to in the embodiments listed directly above) may included in kits of the invention.

In certain embodiments, a kit of the invention further comprises means for determining the MHC-type (e.g. HLA-type) of the subject.

Kits of the invention may include other components required to conduct the methods of the invention, such as antibodies, enzymes, buffers and/or diluents, MHC tetramers, reagents for flow cytometry and/or ELISAs/ELISPOT assays. The kits may comprise one or more means for obtaining a sample from a subject. The kits typically include containers for housing the various components and instructions for using the kit components in the methods of the invention.

Kits of the invention may comprise a suitable support on which one or more reagents are immobilised or may be immobilised. For example, kits of the invention may comprise a support coated with a polypeptide of the invention. Non-limiting examples of suitable supports include assay plates (e.g. microtitre plates) or test tubes manufactured from polyethylene, polypropylene, polystyrene, sephadex, polyvinyl chloride, plastic beads, and, as well as particulate materials such as filter paper, nitrocellulose membrane, agarose, cross-linked dextran, and other polysaccharides.

In certain embodiments, kits of the invention may be used to perform an enzyme-linked immunosorbent assay (ELISA) or an ELISPOT assay.

Additionally or alternatively, kits of the invention may be used to perform western blotting, analyse immune cell proliferation, analyse cytokine synthesis of immune cells, and/or analyse immune cell surface marker expression.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

EXAMPLES

The invention will now be described with reference to specific examples, which should not be construed as in any way limiting.

Example 1: Identification of Autoreactive Lumican Peptide Sequences

Materials and Methods
(i) Proteomic Analyses

Aqueous humor from patients with anterior acute uveitis (AAU) was spun to dry pellet in a speedyvac and resuspended in $CH_3CN$ to adjust to pH8. Sequencing grade porcine trypsin was added at 16 ng/μl to sample and placed in 37 degree oven overnight.

Tryptic digest peptides were separated by on-line cation exchange (SCX) and C18 nano-LC using an Ultimate HPLC, Switchos and Famos autosampler system (LC-Packings, Amsterdam, Netherlands). Peptides (20 μl) were diluted in 20 μl 0.1% v/v formic acid followed by 20 μl of 100% $CH_3CN$ loaded onto a SCX microtrap (168 mm; Michrom Bioresources, Auburn, Calif., USA) at 20 μl/min. Peptides were eluted using 10 μl volumes of ammonium acetate. The unbound load fraction and each salt step were concentrated and desalted using a micro C18 precolumn (500 μm×2 mm; Michrom Bioresources) with $H_2O:CH_3CN$ (98:2, 0.1% formic acid) at 20 μl/min. After a 10 min wash the precolumn was switched (Switchos) into line with a fritless analytical C18 column (75 μm×12 cm) and peptides eluted using a linear gradient of $H_2O:CH_3CN$ (95:5, 0.1% formic acid-buffer A) to $H_2O:CH_3CN$ (40:60, 0.1% formic acid-buffer B) at 200 nl/min over 30 min.

Peptide digests were analysed using LC-MS/MS and was carried out using Thermo Finnigan's LTQ-FT/MS. Peptides were loaded on to a peptide trap cartridge (Agilent, Palo Alto, Calif.) at a flow rate of 1 μL/min. Trapped peptides were then eluted onto a reversed-phase PicoFrit column using a linear gradient of acetonitrile (0-60%) in 0.1% formic acid using a 250 nL/min flow rate. Eluted peptides from the PicoFrit column were sprayed into the LCQ Deca XP mass spectrometer equipped with a nano-spray ion source. Data-dependent acquisition mode was enabled, and each survey MS scan was followed by three MS/MS scans with dynamic exclusion option on. To reduce carry-over, each LC-MS run was followed by a blank injection of buffer and run with the same gradient. MS data were acquired in a repeating 4-s cycle. Dynamic exclusion was set to 1 min. The instrument calibration was performed using Calmix (caffeine, MRFA, and ultramark) according to manufacturer's instructions. The spray voltage was 2.1 kV for LCQ or 1.8 kV for LTQ-FT, while the temperature of ion transfer tube was set at 160*C. The normalized collision energy was set at 35%. FT-ICR survey scans were acquired at the resolution of 100 000 (m/z=400).

(ii) Database Search for Protein Identification

Processing scripts generated data suitable for submission to the database search program MASCOT using the *Homo sapiens* taxonomies. Using Mascot, the data sets were searched against NCBI and SwissProt databases to help eliminate redundancies and identify proteins that might appear in only one database. The precursor ion mass tolerance was set at ±6 ppm, and trypsin was designated as the proteolytic enzyme with up to 1 missed cleavage.

(iii) Lumican Expression in Irus and Synovial Tissues

Human irus pigment epithelial cell (IPE), iris tissues, and synovial tissues were labelled with anti-lumican or control rabbit IgG, followed by HRP or Alexa-fluor conjugated goat anti-rabbit IgG.

(iv) HLA-Binding Affinity

The binding affinity of peptides to HLA-B27 was predicted using BIMAS, T cell epitope prediction models, and SYFPEITHI prediction-programs.

The SYFPEITHI prediction is based on previous publications on T-cell epitopes and MHC ligands, a scoring system that evaluates every amino acid within a given peptide (see, for example, Rammensee et al., (1995), "*MHC ligands and peptide motifs: 1st listing. Immunogenetics*" 41, 178-228; Rammensee et al. (1997), "*MHC ligands and peptide motifs*", Landes Bioscience (International distributor—except North America: Springer Verlag GmbH & Co. KG, Tiergartenstr. 17, D-69121 Heidelberg; Brander and Walker, (1996), "*The HLA-class I CTL response in HIV*-1 *infection: Identification of optimal epitopes*", Los Alamos, N. Mex.: Los Alamos National Laboratory. Theoretical Biology and Biophysics; and Stevanovic et al. (1995), "*Oberflächenantigene im Nierenzellkarzinom—Präsentation von MHC I-gebundenen Selbstpeptiden*", Akt. Urol. Sonderheft (26): 45-46.

The prediction is based on published motifs (pool sequencing, natural ligands) and takes into consideration the amino acids in the anchor and auxiliary anchor positions, as well as other frequent amino acids. The score is calculated according to the following rules: The amino acids of a certain peptide are given a specific value depending on whether they are anchor, auxiliary anchor or preferred residue. Ideal anchors will be given 10 points, unusual anchors 6-8 points, auxiliary anchors 4-6 and preferred residues 1-4 points. Amino acids that are regarded as having a negative effect on the binding ability are given values between −1 and −3.

antigen(s) of host protein and those of a pathogen protein (e.g. similar structure either in amino acid sequence or conformational-fit) despite the proteins originating from dissimilar genes. Exposure to the foreign antigen of the pathogen can elicit a cross-reactive immune response against both the foreign antigen and the similar self-molecule. Subsequently, an infection by the pathogen can trigger a chronic autoimmune reaction and further chronic exposure will eventually initiate the destruction of tissues.

Given that some individuals not previously exposed to *Chlamydia* still develop spondyloarthropathies, it was also postulated that spondyloarthropathies may not be linked exclusively with *Chlamydia* infection. In such cases, spondyloarthropathies may arise by a similar mechanism upon exposure other bacteria and their proteins and it was subsequently identified that a protein of *Aspergillus nidulans* comprises a peptide sequence with strong sequence homology to lumican. This is proposed to account (at least in part) for the observation that individuals not previously exposed to *Chlamydia* can still develop spondyloarthropathies.

The degree of sequence homology shared between a region of the human lumican protein and bacterial and fungal protein sequences and is shown in Table 1 below.

TABLE 1 homology of bacterial and fungal protein sequences with human lumican sequences

| Bacterial Protein | Human lumican Sequence | Sequence Homology |
|---|---|---|
| *Chlamydia trachomatis* fructose biphosphate aldolase protein (GenBank # Q3KL49) | DEYFKRFNALQYLRLSHNELADSGIP (SEQ ID NO: 41) (GenBank # P51884: residues 222-247) | 77% |
| *Chlamydia trachomatis* OMP85 protein (GenBank # Q3KMCI) | DEYFKRFNALQYLRLSHNEL (SEQ ID NO: 42) (GenBank # P51884: residues 222-241) | 44% |
| *Chlamydia trachomatis* serine protease do-like (Swiss-Prot # P18584.2) | DEYFKRFNALQYLRLSHNEL (SEQ ID NO: 42) (GenBank # P51884: residues 222-241) | 71% |
| *Aspergillus nidulans* uncharacterised protein (GenBank # Q5AR12) | YFKRFNALQYL (SEQ ID NO: 43) (GenBank # P51884: residues 224-234) | 81% |

Results

The proteomics investigation to generate an expression profile of the aqueous humor (AH) of anterior acute uveitis (AAU) subjects using mass spectrometry identified similar expression sequences between lumican and the outer membrane glycoprotein (OMP) of *Chlamydia*. It was determined that regions of the human lumican sequence share strong sequence homology with the *Chlamydia* OMP.

As shown in FIG. 1, lumican is expressed in tissues associated with both spondyloarthropies and uveitis. For example, lumican was found to be expressed in human iris epithelial cell (IPE) cultures (FIGS. 1A and 1E), iris tissues (FIGS. 1B and 1F), and synovial tissues (FIGS. 1C, 1D, 1G and 1H). Lumican staining is present in IPE in vitro (FIG. 1E) and in vivo (FIG. 1F), in blood vessels (bv) (FIG. 1G) and in articular cartilage (FIG. 1H).

On that basis it was proposed that the immune system mal-recognises specific sequences in lumican as foreign in *Chlamydia*-exposed individuals leading to spondyloarthropathies. It is postulated that this effect may arise from molecular mimicry whereby a similarity exists between Using BIMAS the peptide sequence the lumican peptide sequence identified was predicted to possess strong binding affinity to HLA-B27.

The lumican peptide sequence identified was also analysed using SYFPEITHI. Strong binding affinity is claimed as a score higher than 15, and the peptide obtained a score of 28 as indicated in Table 2.

TABLE 2

HLA-B27 binding prediction scores for human ocular lumican peptide using SYFPEITHI and BIMAS

| Human sequence | Score (SYFPEITH) | Score (BIMAS) |
|---|---|---|
| DEYF*KRFNALQYLRL*SHNELADSGIP (SEQ ID NO: 41) (GenBank # P51884: residues 222-247) | 28 | 30000 |

The SYFPEITHI scoring system evaluates every amino acid within a given peptide. Individual amino acids may be given the arbitrary value 1 for amino acids that are only slightly preferred in the respective position, optimal anchor residues are given the value 15: any value between these two is possible. The allocation of values is based on the frequency of the respective amino acid in natural ligands, T-cell epitopes, or binding peptides. To ensure that the results were not biased, the entire human lumican sequence as displayed in Table 3 (GenBank # P51884) was blasted against microbial sequences using the swissprot database.

Furthermore, the entire sequence was processed using T cell epitope prediction models. These tools predict the IC50 values for peptides binding to specific MHC molecules, as shown in Table 4 where the lowest amount of concentration represents the lowest amount of molecule required to elicit a T-cell response. The highest and lowest scores obtained using this software were an exact match to the sequence homology of lumican to the *Aspergillus nidulans* protein displayed in Table 1. This ensures that the sequence is bound by HLA-B27 with high affinity (Table 4, IC50 of 93 nm) and thus induces an immune response when subjected to HLA-B27 T cells. Moreover, it suggests that an HLA-B27 positive individual exposed to *Chlamydia* or *Aspergillus* produces an immune response that stimulates a T-cell selection and clonal expansion. Subsequent and chronic exposure will ensure an attack on the lumican protein since T-cells malrecognized it as foreign. Accordingly, the *Chlamydia*-lumican and *Aspergillus*-lumican mimicry leads to the leading missing link and formation spondyloarthropathies such as ankylosing spondylitis, juvenile arthritis, psoriasis and uveitis.

TABLE 3 the full sequence of human lumican (GenBank # P51884) (SEQ ID NO: 1)

| | | | | | |
|---|---|---|---|---|---|
| 1   MSLSAFTLFL | ALIGGTSGQY | YDYDFPLSIY | GQSSPNCAPE | CNCPESYPSA | MYCDELKLKS |
| 61  VPMVPPGIKY | LYLRNNQIDH | IDEKAFENVT | DLQWLILDHN | LLENSKIKGR | VFSKLKQLKK |
| 121 LHINHNNLTE | SVGPLPKSLE | DLQLTHNKIT | KLGSFEGLVN | LTFIHLQHNR | LKEDAVSAAF |
| 181 KGLKSLEYLD | LSFNQIARLP | SGLPVSLLTL | YLDNNKISNI | PDEYFKRFNA | LQYLRLSHNE |
| 241 <u>LADSGIPGNS</u> | FNVSSLVELD | LSYNKLKNIP | TVNENLENYY | LEVNQLEKFD | IKSFCKILGP |
| 301 LSYSKIKHLR | LDGNRISETS | LPPDMYECLR | VANEVTLN | | |

TABLE 4 the combined predictors of proteasomal processing, TAP transport, MHC 1 binding to produce an overall score for each peptide's intrinsic potential of being a T cell epitope

| Allele | Position | Pep Length | Sequence | Proteosome Score | TAP Score | MHC Score | Processing Score | Total Score | MHC IC50 nM |
|---|---|---|---|---|---|---|---|---|---|
| HLA B*27051 | :2-10 | 9.0000 | SLSAFTLFL (SEQ ID: NO 44) | 1.3800 | 0.4600 | -4.4000 | 1.8400 | -2.5600 | 24862.1000 |
| HLA B*27051 | :131-139 | 9.0000 | SVGPLPKSL (SEQ ID: NO 45) | 1.3700 | 0.3600 | -5.2200 | 1.7200 | -3.4900 | 164157.9000 |
| HLA B*27051 | :301-309 | 9.0000 | LSYSKIKHL (SEQ ID: NO 46) | 1.3500 | 0.4500 | -4.4100 | 1.8000 | -2.6000 | 25420.8000 |
| HLA B*27051 | :202-210 | 9.0000 | GLPVSLLTL (SEQ ID: NO 47) | 1.3400 | 0.3600 | -4.6800 | 1.7000 | -2.9800 | 47471.1000 |
| HLA B*27051 | :63-71 | 9.0000 | MVPPGIKYL (SEQ ID: NO 48) | 1.3000 | 0.4300 | -5.4200 | 1.7300 | -3.6900 | 265554.3000 |
| HLA B*27051 | :14-22 | 9.0000 | GGTSGQYYD (SEQ ID: NO 49) | 1.3000 | -0.9900 | -5.3700 | 0.3100 | -5.0600 | 235429.6000 |
| HLA B*27051 | :233-241 | 9.0000 | YLRLSHNEL (SEQ ID: NO 50) | 1.3000 | 0.4200 | -4.7900 | 1.7100 | -3.0800 | 62221.3000 |
| HLA B*27051 | :46-54 | 9.0000 | SYPSAMYCD (SEQ ID: NO 51) | 1.2700 | -0.7300 | -5.8900 | 0.5400 | -5.3500 | 774085.2000 |
| HLA B*27051 | :166-174 | 9.0000 | LQHNRLKED (SEQ ID: NO 52) | 1.2400 | -0.7500 | -4.4600 | 0.4900 | -3.9800 | 29123.6000 |
| HLA B*27051 | :251-259 | 9.0000 | FNVSSLVEL (SEQ ID: NO 53) | 1.2300 | 0.3700 | -4.5600 | 1.6000 | -2.9600 | 36427.8000 |
| HLA B*27051 | :250-258 | 9.0000 | SFNVSSLVE (SEQ ID: NO 54) | 1.2200 | -0.5600 | -5.9700 | 0.6600 | -5.3100 | 929644.7000 |
| HLA B*27051 | :329-337 | 9.0000 | LRVANEVTL (SEQ ID: NO 55) | 1.2200 | 0.5400 | -2.8300 | 1.7600 | -1.0700 | 682.7000 |

TABLE 4-continued the combined predictors of proteasomal processing, TAP transport, MHC 1 binding to produce an overall score for each peptide's intrinsic potential of being a T cell epitope

| Allele | Position | Pep Length | Sequence | Proteosome Score | TAP Score | MHC Score | Processing Score | Total Score | MHC IC50 nM |
|---|---|---|---|---|---|---|---|---|---|
| HLA B*27051 | 321-329 | 9.0000 | LPPDMYECL (SEQ ID: NO 56) | 1.2200 | 0.3000 | -5.8100 | 1.5200 | -4.2900 | 646609.2000 |
| HLA B*27051 | 228-236 | 9.0000 | FNALQYLRL (SEQ ID: NO 57) | 1.2100 | 0.3700 | -4.0200 | 1.5900 | -2.4300 | 10510.6000 |
| HLA B*27051 | 170-178 | 9.0000 | RLKEDAVSA (SEQ ID: NO 58) | 1.2100 | -0.0600 | -4.1800 | 1.1500 | -3.0300 | 15078.1000 |
| HLA B*27051 | 226-234 | 9.0000 | KRFNALQYL (SEQ ID: NO 59) | 1.2000 | 0.5600 | -1.9700 | 1.7600 | -0.2100 | 93.1000 |
| HLA B*27051 | 65-73 | 9.0000 | PFGIKYLYL (SEQ ID: NO 60) | 1.2000 | 0.0300 | -6.0400 | 1.2200 | -4.8200 | 1102999.8000 |

IC50 values were also predicted for binding of lumican nonamers commencing at positions 235 and 236 to various HLA-A and HLA-B alleles (Table 5).

TABLE 5 predicted IC50 values for binding of lumican nonamers to various HLA-A and HLA-B alleles

| HLA Allele | Position of nonamer in Lumican polypeptide | PepLength | Sequence | IC50 [nM] |
|---|---|---|---|---|
| HLA B*1503 | 225-233 | 9 | FKRFNALQY (SEQ ID NO: 60) | 1.2 |
| HLA B*2705 | 226-234 | 9 | KRFNALQYL (SEQ ID NO: 2) | 93.1 |
| HLA B*1503 | 226-234 | 9 | KRFNALQYL (SEQ ID NO: 2) | 143.4 |
| HLA A*0202 | 226-234 | 9 | KRFNALQYL (SEQ ID NO: 2) | 163.7 |
| HLA A*8001 | 225-233 | 9 | FKRFNALQY (SEQ ID NO: 60) | 265.4 |
| HLA A*3001 | 226-234 | 9 | KRFNALQYL (SEQ ID NO: 2) | 404.1 |
| HLA A*2902 | 225-233 | 9 | FKRFNALQY (SEQ ID NO: 60) | 508.5 |
| HLA A*3201 | 226-234 | 9 | KRFNALQYL (SEQ ID NO: 2) | 1047.6 |
| HLA A*3001 | 225-233 | 9 | FKRFNALQY (SEQ ID NO: 60) | 1415.3 |
| HLA B*4002 | 226-234 | 9 | KRFNALQYL (SEQ ID NO: 2) | 1624.5 |
| HLA A*3002 | 225-233 | 9 | FKRFNALQY (SEQ ID NO: 60) | 1818.9 |
| HLA A*0203 | 226-234 | 9 | KRFNALQYL (SEQ ID NO: 2) | 2156.9 |
| HLA A*0201 | 226-234 | 9 | KRFNALQYL (SEQ ID NO: 2) | 2158.6 |
| HLA B*3501 | 225-233 | 9 | FKRFNALQY (SEQ ID NO: 60) | 2699.8 |
| HLA B*4801 | 226-234 | 9 | KRFNALQYL (SEQ ID NO: 2) | 3903.0 |
| HLA A*2301 | 236-244 | 9 | KRFNALQYL (SEQ ID NO: 2) | 4492.9 |
| HLA A*2403 | 236-244 | 9 | KRFNALQYL (SEQ ID NO: 2) | 4652.1 |
| HLA B*1501 | 235-243 | 9 | FKRFNALQY (SEQ ID NO: 60) | 5413.4 |
| HLA B*0801 | 236-244 | 9 | KRFNALQYL (SEQ ID NO: 2) | 6168.3 |

SYFPEITHI results (Tables 6-20) indicated that HLA-A and HLA-B alleles have a strong affinity for at least the following lumican nonamers and octamers (strong binding affinity is claimed as a score higher than 15).

TABLE 6

HLA-A*03
HLA-A*03 nonamers

| Position in lumican polypeptide | 1 2 3 4 5 6 7 8 9 | Predicted binding score |
|---|---|---|
| 230 | A L Q Y L R L S H (SEQ ID NO: 61) | 23 |
| 225 | F K R F N A L Q Y (SEQ ID NO: 60) | 18 |

TABLE 7

HLA-A*2402
HLA-A*2402 nonamers

| Position in lumican polypeptide | 1 2 3 4 5 6 7 8 9 | Predicted binding score |
|---|---|---|
| 213 | E Y F K R F N A L (SEQ ID NO: 62) | 32 |

TABLE 8

HLA-B*08
HLA-B*08 nonamers

| Position in lumican polypeptide | 1 2 3 4 5 6 7 8 9 | Predicted binding score |
|---|---|---|
| 233 | Y L R L S H N E L (SEQ ID NO: 50) | 24 |

TABLE 9

HLA-B*1402
HLA-B*1402 nonamers

| Position in lumican polypeptide | 1 2 3 4 5 6 7 8 9 | Predicted binding score |
|---|---|---|
| 226 | K R F N A L Q Y L (SEQ ID NO: 2) | 25 |

TABLE 10

HLA-B*2705
HLA-B*2705 nonamers

| Position in lumican polypeptide | 1 2 3 4 5 6 7 8 9 | Predicted binding score |
|---|---|---|
| 226 | K R F N A L Q Y L (SEQ ID NO: 2) | 26 |

TABLE 11

HLA-B*2709
HLA-B*2709 nonamers

| Position in lumican polypeptide | 1 2 3 4 5 6 7 8 9 | Predicted binding score |
|---|---|---|
| 226 | K R F N A L Q Y L (SEQ ID NO: 2) | 24 |

TABLE 12

HLA-B*3901
HLA-B*3901 nonamers

| Position in lumican polypeptide | 1 2 3 4 5 6 7 8 9 | Predicted binding score |
|---|---|---|
| 226 | K R F N A L Q Y L (SEQ ID NO: 2) | 21 |

TABLE 13

HLA-B*3902
HLA-B*3902 nonamers

| Position in lumican polypeptide | 1 2 3 4 5 6 7 8 9 | Predicted binding score |
|---|---|---|
| 226 | K R F N A L Q Y L (SEQ ID NO: 2) | 16 |

TABLE 14

HLA-B*1402 (octamer)
HLA-B*1402 octamers

| Position in lumican polypeptide | 1 2 3 4 5 6 7 8 | Predicted binding score |
|---|---|---|
| 234 | L R L S H N E L (SEQ ID NO: 63) | 25 |

TABLE 15

HLA-B*1402 (nonamer)
HLA-B*1402 nonamers

| Position in lumican polypeptide | 1 2 3 4 5 6 7 8 9 | Predicted binding score |
|---|---|---|
| 226 | K R F N A L Q Y L (SEQ ID NO: 2) | 25 |

TABLE 16

HLA-B*3801
HLA-B*3801 nonamers

| Position in lumican polypeptide | 1 2 3 4 5 6 7 8 9 | Predicted binding score |
|---|---|---|
| 226 | K R F N A L Q Y L (SEQ ID NO: 2) | 17 |
| 225 | F K R F N A L Q Y (SEQ ID NO: 60) | 0 |

TABLE 17

| HLA-B*2709 |
|---|
| HLA-B*2709 nonamers |

| Position in lumican polypeptide | 1 2 3 4 5 6 7 8 9 | Predicted binding score |
|---|---|---|
| 226 | K R F N A L Q Y L (SEQ ID NO: 2) | 24 |

TABLE 18

| HLA-A*26 |
|---|
| HLA-A*26 nonamers |

| Position in lumican polypeptide | 1 2 3 4 5 6 7 8 9 | Predicted binding score |
|---|---|---|
| 226 | K R F N A L Q Y L (SEQ ID NO: 2) | 16 |

TABLE 19

| HLA-A*01 |
|---|
| HLA-A*01 nonamers |

| Position in lumican polypeptide | 1 2 3 4 5 6 7 8 9 | Predicted binding score |
|---|---|---|
| 225 | F K R F N A L Q Y (SEQ ID NO: 60) | 18 |

TABLE 20

| H2-Kd |
|---|
| H2-Kd nonamers |

| Position in lumican polypeptide | 1 2 3 4 5 6 7 8 9 | Predicted binding score |
|---|---|---|
| 226 | K R F N A L Q Y L (SEQ ID NO: 2) | 15 |

Example 2: HLA B27 Peptide Binding Assay

Materials and Methods

HLA B27 epitope analyses were conducted using The REVEAL & ProVE® Rapid Epitope Discovery System.

(i) Peptide Synthesis:

37×9-mer peptides from Lumican and *Chlamydia trachomatis* were synthesized (see Table 21). The peptides were synthesized as a Prospector PEPscreen®: Custom Peptide Library. Peptides were synthesized in 0.5-2 mg quantities with high average purity. Quality control by MALDI-TOF Mass Spectrometry was carried out all of samples.

TABLE 21

Custom peptides were generated using Prospector PEPscreen ® custom peptide library synthesis.

| I.D. | Peptide |
|---|---|
| 1 | KRFNALQYL (SEQ ID NO: 2) |
| 2 | RRQLEDIRL (SEQ ID NO: 64) |
| 3 | LRLSHNELA (SEQ ID NO: 65) |
| 4 | LQYLRLSHN (SEQ ID NO: 34) |
| 5 | EHKHTRRQL (SEQ ID NO: 66) |
| 6 | HKHTRRQLE (SEQ ID NO: 67) |
| 7 | KHTRRQLED (SEQ ID NO: 68) |
| 8 | HTRRQLEDI (SEQ ID NO: 69) |
| 9 | TRRQLEDIR (SEQ ID NO: 70) |
| 10 | RRQLEDIRL (SEQ ID NO: 64) |
| 11 | RQLEDIRLD (SEQ ID NO: 71) |
| 12 | QLEDIRLDG (SEQ ID NO: 35) |
| 13 | LEDIRLDGN (SEQ ID NO: 72) |
| 14 | DEYFKRFNA (SEQ ID NO: 73) |
| 15 | EYFKRFNAL (SEQ ID NO: 62) |
| 16 | YFKRFNALQ (SEQ ID NO: 74) |
| 17 | FKRFNALQY (SEQ ID NO: 60) |
| 18 | KRFNALQYL (SEQ ID NO: 2) |
| 19 | RFNALQYLR (SEQ ID NO: 75) |
| 20 | FNALQYLRL (SEQ ID NO: 57) |
| 21 | NALQYLRLS (SEQ ID NO: 76) |
| 22 | ALQYLRLSH (SEQ ID NO: 77) |
| 23 | LQYLRLSHN (SEQ ID NO: 34) |
| 24 | QYLRLSHNE (SEQ ID NO: 78) |
| 25 | LSHNEL (SEQ ID NO: 79) |
| 26 | PLNLRSIDL (SEQ ID NO: 36) |

TABLE 21-continued

Custom peptides were generated using Prospector PEPscreen ® custom peptide library synthesis.

| I.D. | Peptide |
|---|---|
| 27 | LNLRSIDLQ (SEQ ID NO: 80) |
| 28 | NLRSIDLQD (SEQ ID NO: 81) |
| 29 | LRSIDLQDF (SEQ ID NO: 82) |
| 30 | RSIDLQDFF (SEQ ID NO: 83) |
| 31 | SIDLQDFFS (SEQ ID NO: 84) |
| 32 | IDLQDFFSS (SEQ ID NO: 85) |
| 33 | DLQDFFSSL (SEQ ID NO: 86) |
| 34 | LQDFFSSLI (SEQ ID NO: 87) |
| 35 | DPCTTWCDA (SEQ ID NO: 88) |
| 36 | RRRWRRLTV (SEQ ID NO: 89) |
| 37 | ARGQPGVMG (SEQ ID NO: 90) |

(ii) MHC-Peptide Binding Assay:

Each peptide was screened for binding to HLAB*2705. Candidate peptides were assembled with B*2705 and analysed using the REVEAL™ MHC-peptide binding assay to determine their level of incorporation into MHC molecules. Binding to MHC molecules was compared to that of two known T-cell epitopes: a positive control peptide and an intermediate control peptide with very strong and weaker binding properties, respectively.

Figure 6:
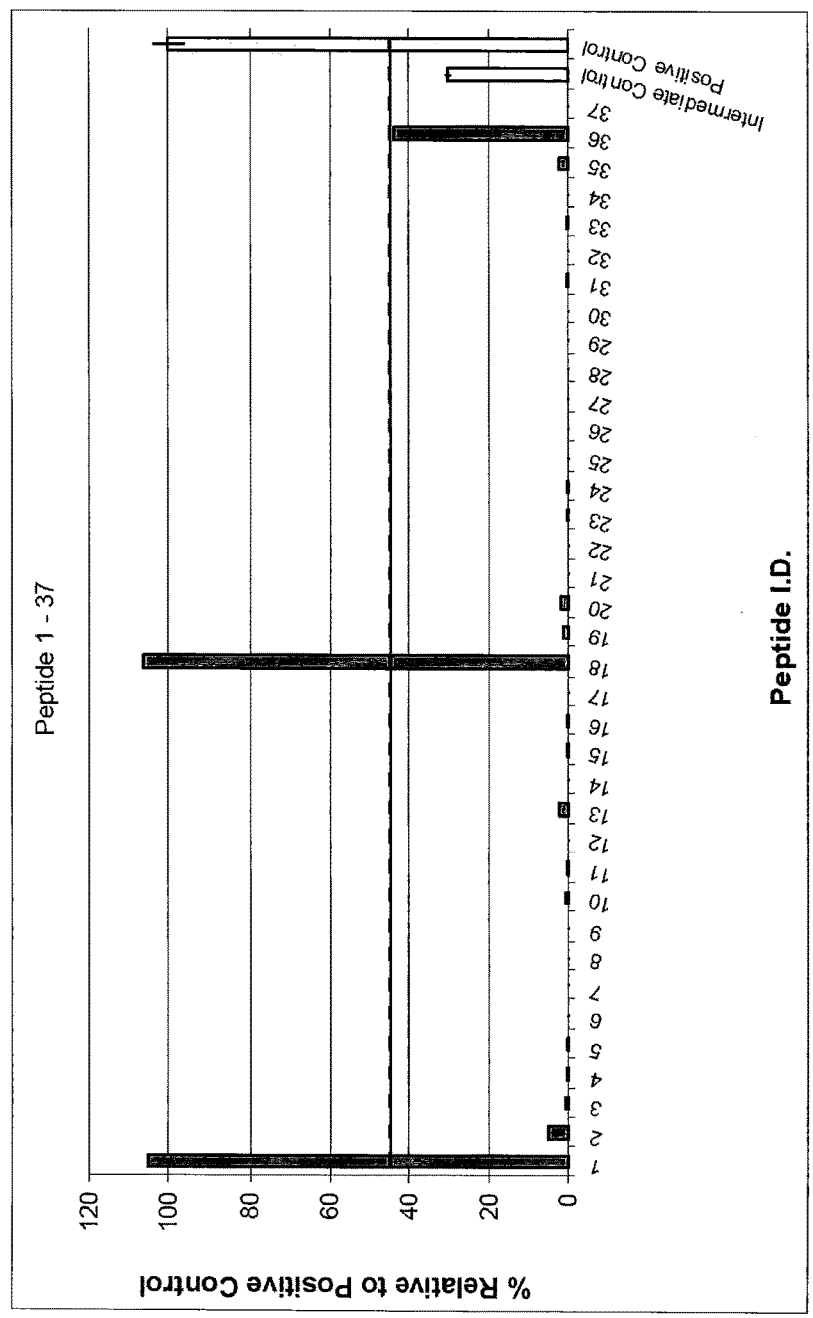
FIG. 6 is a graph showing the results of an HLAB*2705 peptide binding assay using peptides derived from the human lumican protein. The binding score for each peptide is shown as a percentage relative to the binding of the positive control (X-axis). Peptide numbers are shown on the Y-axis and correspond to those listed in Table 22. The pass/fail threshold is indicated by the horizontal line at 45%.
Figure 7:
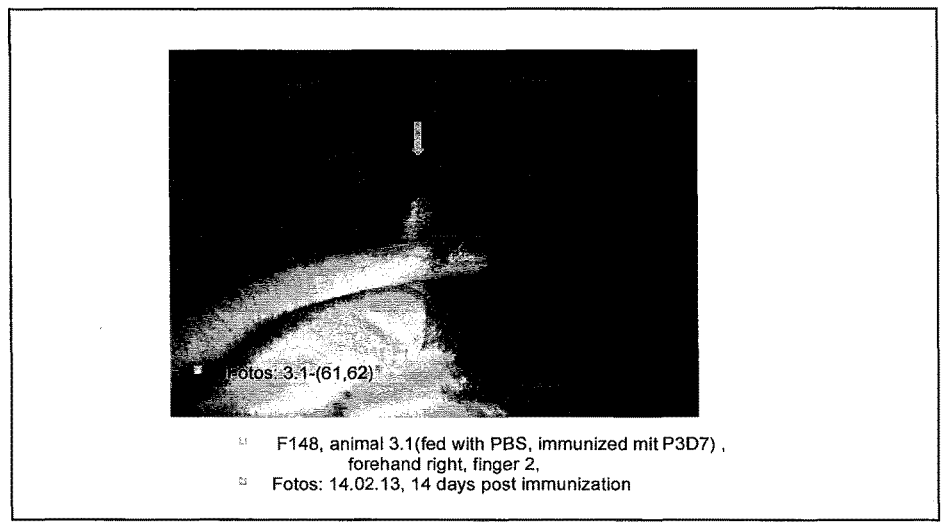
FIG. 7 is a photographic image of a mouse administered peptides in accordance with the methods of the present invention.

The binding score for each peptide is shown as a percentage relative to the binding of the positive control (see FIG. 6). Only peptides with scores ≥45% of this positive control are referred to as passed epitopes. This pass/fail threshold is shown graphically as the red line of FIG. 6. Passed peptide determinations are relative measures and thus served as a general guideline to binding affinity. In general, strong T-cell epitopes tend to be identified as clear positive responses in this assay. Binding of the intermediate control (yellow bar) is shown to allow comparison of sample peptides with another T-cell epitope with weaker binding characteristics in the assay.

Table 22 shows peptide binding results ordered by peptide I.D. number, while Table 23 shows peptide binding results ordered by highest score. Experimental standard error was obtained by triplicate positive and intermediate control binding experiments. The standard error for these controls is shown in Table 22 below and was assumed to be representative of the degree of error that would be present for all samples.

TABLE 22

Peptide binding results ordered by peptide I.D. number. Peptides with REVEAL™ binding assay scores >45% are highlighted

| Peptide I.D. | % Positive Control |
|---|---|
| 1 | 105.51 |
| 2 | 5.26 |
| 3 | 0.72 |
| 4 | 0.24 |
| 5 | 0.43 |
| 6 | 0.00 |
| 7 | 0.04 |
| 8 | 0.04 |
| 9 | 0.02 |
| 10 | 1.06 |
| 11 | 0.50 |
| 12 | 0.00 |
| 13 | 2.17 |
| 14 | 0.06 |
| 15 | 0.48 |
| 16 | 0.47 |
| 17 | 0.15 |
| 18 | 106.17 |
| 19 | 1.20 |
| 20 | 1.81 |
| 21 | 0.11 |
| 22 | 0.13 |
| 23 | 0.55 |
| 24 | 0.50 |
| 25 | 0.03 |
| 26 | 0.00 |
| 27 | 0.11 |
| 28 | 0.17 |
| 29 | 0.08 |
| 30 | 0.08 |
| 31 | 0.26 |
| 32 | 0.13 |
| 33 | 0.35 |
| 34 | 0.11 |
| 35 | 2.18 |
| 36 | 43.98 |
| 37 | 0.00 |
| Intermediate Control | 30.33 +/− 0.3 |
| Positive Control | 100.00 +/− 3.8 |

TABLE 23

Peptide binding results ordered by highest binding score. Peptides with REVEAL™ binding assay scores >45% are highlighted.

| Peptide I.D. | % Positive Control | Peptide I.D. | % Positive Control |
|---|---|---|---|
| 18 | 106.17 | 21 | 0.11 |
| 1 | 105.51 | 27 | 0.11 |
| Positive Control | 100.00 +/− 3.8 | 34 | 0.11 |
| 36 | 43.98 | 30 | 0.08 |
| Intermediate Control | 30.33 +/− 0.3 | 29 | 0.08 |
| 2 | 5.26 | 14 | 0.06 |
| 35 | 7.18 | 7 | 0.04 |
| 13 | 2.17 | 8 | 0.04 |
| 20 | 1.81 | 25 | 0.03 |
| 19 | 1.20 | 9 | 0.02 |
| 10 | 1.06 | 12 | 0.00 |
| 3 | 0.72 | 26 | 0.00 |
| 23 | 0.55 | 37 | 0.00 |
| 24 | 0.50 | 6 | 0.00 |
| 11 | 0.50 | | |
| 15 | 0.48 | | |
| 16 | 0.47 | | |
| 5 | 0.43 | | |
| 33 | 0.35 | | |
| 31 | 0.26 | | |
| 4 | 0.24 | | |
| 28 | 0.17 | | |

TABLE 23-continued

Peptide binding results ordered by highest binding score. Peptides with REVEAL ™ binding assay scores >45% are highlighted.

| Peptide I.D. | % Positive Control | Peptide I.D. | % Positive Control |
|---|---|---|---|
| 17 | 0.15 | | |
| 22 | 0.13 | | |
| 32 | 0.13 | | |

Example 2: Role of Optican and Lumican Proteins in the Pathogenesis of Anterior Uveitis Materials and Methods (i) MHC Binding Assays In a series of studies, the complete protein sequences of lumican, opticin and *C. trachomatis* were extracted from the Swiss-Prot database in a fasta format. Protein-sequences were analysed using the computational HLA-binding prediction software tools: SYFPEITHI (see Rada et al. (1993), "Regulation of corneal collagen fibrillogenesis in vitro by corneal proteoglycan (lumican and decorin) core proteins", Exp Eye Res. 56(6): p. 635-48), and BIMAS (see Rammensee, et al., (1999), "SYFPEITHI: database for MHC ligands and peptide motifs", Immunogenetics, 50(3-4): p. 213-9). Using computational methods, 9-mer peptides that bound with variable affinities to HLA-B2705 (Table 24) were identified. This algorithm based method of detecting peptide binding can be inaccurate, may lead to both false positive and false negative results and cannot reveal which peptides are the most naturally immunogenic. Therefore we examined their binding affinity to HLA-B2705 with an in vitro MHC-peptide binding assay (REVEAL Epitope discovery system. ProImmune, Oxford. UK) (see Rammensee, et al., (1999), supra). A total of 37 peptides derived from peptide sequences of interest from lumican, opticin and *Chlamydia* were tested. This strategy revealed that one of the original peptides (lumican peptide 1—Table 24) showed significant binding relative to the positive control peptides. It was subsequently ascertained if these peptides are recognised in vivo by T cells of patients with anterior uveitis (AU).

(ii) Patients

All subjects were recruited from the uveitis clinic at St Vincent's Hospital, Sydney. All patients had a detailed history and examination and were investigated as per our previously published protocol (see Burrows, et al., (2007), "The impact of HLA-B micropolymorphism outside primary peptide anchor pockets on the CTL response to CMV", Eur J Immunol, 37(4): p. 946-53) and had serology performed for *C. Trachomatis* by Elisa. All patients with associated SpA were assessed by a rheumatologist or immunologist and fulfilled international diagnostic criteria for these diseases and fulfilled international diagnostic criteria for these diseases. Patients had HLA-B27 typing for stratification into study groups and their peripheral blood was collected for analysis. Patients on immunosuppressive therapy and biological agents (such as anti-TNF therapy) were excluded.

(iii) Immunohistochemistry

Human iris pigment epithelial (IPE) cell cultures, iris tissues and synovial tissues were stained with anti-lumican or control rabbit IgG, followed by HRP or Alexa-fluor conjugated goat anti-rabbit IgG as previously described.

(iv) Peptide Synthesis

Peptides were synthesized on an MK-IV peptide synthesizer, purified by HPLC and verified by liquid chromatography-mass spectrometry on an HPLC Shimadzu QP8000 system. All peptides were over 95% pure and stored at −20° C. until used. Peptides were dissolved in DMSO and stored at −80° C. until used.

(v) HLA Typing

HLA B27 typing was performed by flow cytometry and confirmed by PCR. DNA was extracted from PBMCs with the QIAamp kit (Qiagen); multiplex PCR analysis of this DNA (Dynal Biotech) was used for HLA-B2705 typing.

(vi) EliSpot Assay

PBMC from HLA-B27 patients with active disease and controls were tested with the selected peptides (Table 24) in ex vivo IFN-γ EliSpot assays as previously described (see Kuon and J Sieper, (2003), "Identification of HLA-B27-restricted peptides in reactive arthritis and other spondyloarthropathies: computer algorithms and fluorescent activated cell sorting analysis as tools for hunting of HLA-B27-restricted chlamydial and autologous crossreactive peptides involved in reactive arthritis and ankylosing spondylitis". Rheum Dis Clin North Am. 29(3): p. 595-611; Glant, et al., (1988), "Mapping of arthritogenic/autoimmune epitopes of cartilage aggrecans in proteoglycan-induced arthritis". Scand J Rheumatol Suppl, 101: p. 43-9; and Cantagrel, et al., (1988), "The transsynovial lymphocytic ratio. Characterization of blood and synovial fluid lymphocytes from patients with arthritic diseases". J Rheumatol, 15(6): p. 899-904.)

Approximately $1 \times 10^5$ PBMCs were used per well, with phytohemagglutinin or medium alone as the positive or negative control, respectively. Groups of three peptides were initially tested to ascertain which peptides stimulated a significant IFN-γ production. Each peptide or peptide combination was tested in triplicate at a concentration of 5 mM per peptide. This concentration of peptide was ascertained in preliminary studies to give optimal responses (data not shown). All positive responses were tested at lower peptide concentrations with cultured EliSpot assays of a subset of samples, where additional cells were available. Peptides found to bind to HLA-B2705 with high affinity (peptides 1, 6 and 7—Table 24) and low affinity binding peptides (peptides 2, 3, 4, 5, 8-10—Table 24), were included, as well as peptides know to stimulate T cells of patients with AS (peptide 8 and 9, Table 24) (see Kuon, W., et al., (1997), "Recognition of chlamydial antigen by HLA-B27-restricted cytotoxic T cells in HLA-B*2705 transgenic CBA (H-2k) mice" Arthritis Rheum. 40(5): p. 945-54).

Results (i) Patients

Twenty-five patients with HLA B27 related disease were examined. There were 17 males with a median aged 45.5 years and 8 females with a median age of 37.2 years. All patients were HLA B27 positive by flow cytometry.

(ii) Lumican Immunohistochemistry

Human IPE cultures (A and E), iris tissues (B and F), synovial tissues (C-D, G-H) were labelled with anti-lumican or control rabbit IgG, followed by HRP or Alexa-fluor conjugated goat anti-rabbit IgG. Lumican staining (red) is present in IPE in vitro (E) and in vivo (F), in blood vessels (bv) (G) and in articular cartilage (H) (FIG. 1).

(iii) Peptide Binding to HLA B2705

Predicted peptide binding to HLA-B2705 (ANN method) using tools from the Immune Epitope Database and Analysis Resource (see Appel, et al., (2004), "The solvent-inaccessible Cys67 residue of HLA-B27 contributes to T cell recognition of HLA-B27/peptide complexes". J Immunol, 2004. 173(11): p. 6564-73) are shown in Table 24. $IC_{50}$ value <50 nM is considered to be high affinity, >5000 nM is considered to be low affinity. Reactivity to peptides derived from matrix components of the eye and joints (peptides 1-4 and 8-10—Table 24) and peptides derived from *Chlamydia trachomatis* (peptides 5-7—Table 24) were examined in patients with AU and relevant control subjects (Table 25). High and low affinity peptide sequences were included to serve as positive and negative controls.

normalised such that the number of counts in the negative control was defined as 1.0 and all other counts relative to this. Ten patients with HLA B27 AU were compared with healthy controls. These patients showed a significant difference between their response to lumican vs the average of the

TABLE 24

Nine-mer peptides and their predicted binding to HLA-B2705

| Peptide Number | Sequence | Protein Origin | $IC_{50}$ (nM)[#] | Accession number |
|---|---|---|---|---|
| 1 | KRFNALQYL (SEQ ID NO: 2) | Lumican | 30.3 | NP_002336.1 |
| 2 | LQNNLIETI (SEQ ID NO: 33) | Keratocan/Opticin | 2392.6 | NP_008966.1 NP_055174.1 |
| 3 | LQYLRLSHN (SEQ ID NO: 34) | Lumican | 8955.5 | NP_002336.1 |
| 4 | QLEDIRLDG (SEQ ID NO: 35) | Opticin | 28246.6 | NP_055174.1 |
| 5 | PLNLRSIDL (SEQ ID NO: 36) | *Chlamydia trachomatis* | 26278.7 | NP_219980.1 |
| 6 | ARKLLLDNL (SEQ ID NO: 37) | *Chlamydia trachomatis* | 267.8 | NP_220127.1 |
| 7 | NRFSVAYML (SEQ ID NO: 38) | I *Chlamydia trachomatis* | 30.7 | NP_219924.1 |
| 8 | DRASFIKNL (SEQ ID NO: 91) | Collagen type VI alpha 2 (C34) | 614.8 | NP_478054.2 |
| 9 | SRHHAFCFR (SEQ ID NO: 92) | Aggrecan | 331.4 | NP_001126.3 |
| 10 | ARGQPGVMG (SEQ ID NO: 90) | Collagen type II alpha 1 | 13735.6 | NP_149162.2 |

[#]Predicted peptide binding to HLA-B2705 (ANN method) using tools from the Immune Epitope Database and Analysis Resource. $IC_{50}$ value <50 nM is considered to be high affinity, >5000 nM is considered to be low affinity.

(iv) *Chlamydia* Serology

Thirteen of the 25 patients who participated in this study and one of the 6 control subjects had positive serology for *C. Trachomatis* as detected in an ELISA assay.

(v) EliSpot Assays

Figure 3:
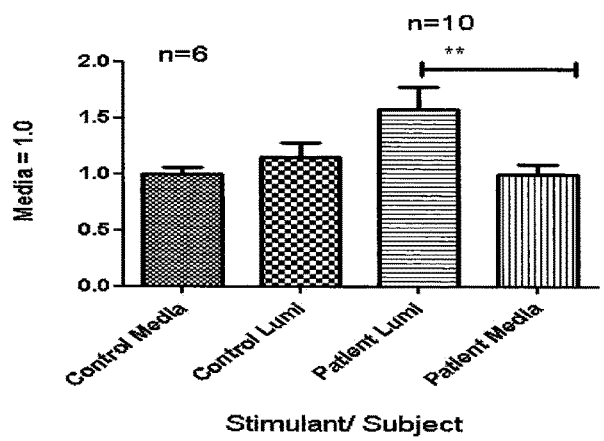
FIG. 3 is a graph showing averaged results of an Elispot assay measuring IFN-γ responses after administration of lumican protein (2.5 μg/mL) to PBMC of HLA B27 positive patients and PBMC of controls. IFN-γ responses were compared to control and patient PBMC administered only media. X-axis: sample. Y-axis—ratio of spot-forming units (SFU's) (sample vs negative control media). Negative control is by definition 1.0 on the Y-axis.

Mixtures were made into four groups of three peptides each, as shown in Table 25. An EBV-derived peptide was used as a standardisation control and whole recombinant human lumican was also used. The culture media (complete RPMI) was the negative control and PHA the positive control. $1 \times 10^5$ cells were added per well, cells left to incubate for 24 hours and counted after the incubation of detection antibody and colour assay. Cells were then counted. For the purposes of data analysis values were healthy controls (n=6) (one way ANOVA, Bonferroni multiple comparison test) (FIG. 3).

Figure 2:
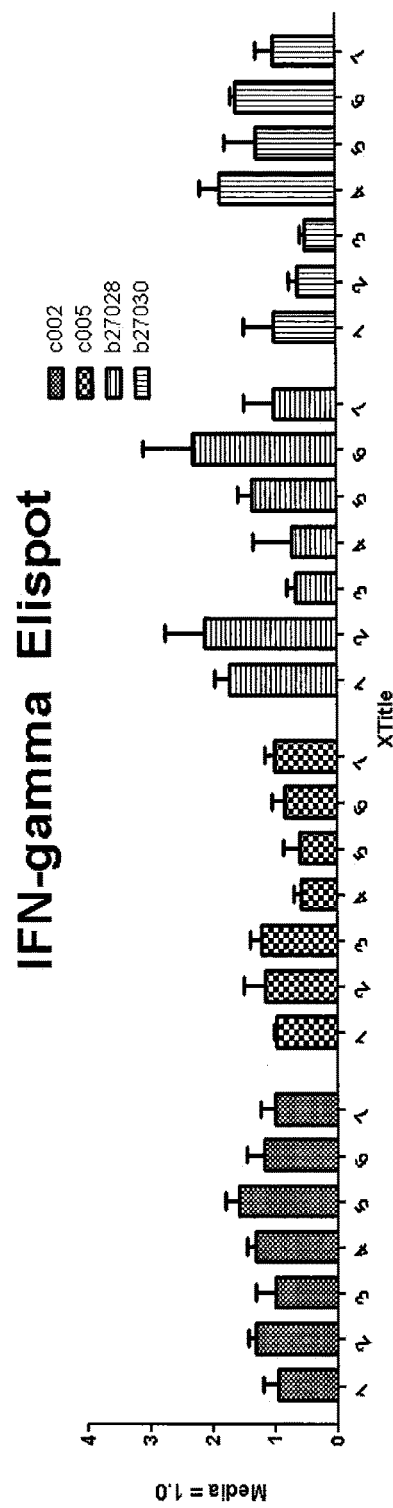
FIG. 2 is a graph showing the results of an Elispot assay measuring IFN-γ responses to HLA B27-binding peptides in peripheral blood mononuclear cells (PBMC) of two patients with acute uveitis (b27028 and b27030) and two control subjects (c002 and c005). X-axis—Nos. 1-4: peptide mixtures corresponding to sets 1-4 of Table 25; No. 5: EBV peptide from Table 25; No. 6: recombinant human lumican; No. 7: negative control (complete RPMI); Y-axis—ratio of spot-forming units (SFU's) (sample vs negative control media). Negative control is by definition 1.0 on the Y-axis. PHA is not shown though all cells displayed a strong response to it. All peptides were made to final concentrations of 5 μg/mL each and recombinant human lumican was used at a final concentration of 2.5 μg/mL.

The response to individual peptide mixtures in two HLA B27 positive patients (b27028 and b27030) and two controls is shown in FIG. 2.

Table 25 outline IFN-γ EliSpot assay results from stimulation of PBMC with peptide mixtures and lumican protein. Patients with HLA B27 AU responded to peptides and lumican more frequently than controls (p<0.05) with 8 of 10 patients demonstrating increased IFN-γ production to lumican and (set 4) peptides derived from aggrecan, collagen and *C. Trachomatis*, and 6 of 10 patients responding to peptides derived from opticin and *C. Trachomatis* (set 2) peptides and interestingly to EBV peptides (Table 25).

TABLE 25

Interferon gamma response to HLA B27 binding peptides

| Set | Peptide/protein | Source | Patients (N = 10) | Controls (N-6) |
|---|---|---|---|---|
| 1 | KRFNALQYL (SEQ ID NO: 2) | Lumican | 4 | 0 |
|  | LQNNLIETI (SEQ ID NO: 33) | Keratocan/Opticin |  |  |
|  | LQYLRLSHN (SEQ ID NO: 34) | Lumican |  |  |

TABLE 25-continued

Interferon gamma response to HLA B27 binding peptides

| Set | Peptide/protein | Source | Patients (N = 10) | Controls (N-6) |
|---|---|---|---|---|
| 2 | QLEDIRLDG (SEQ ID NO: 35) | Opticin | 6 | 2 |
|   | PLNLRSIDL (SEQ ID NO: 36) | Chlamydia trachomatis | | |
|   | ARKLLLDNL (SEQ ID NO: 37) | Chlamydia trachomatis | | |
| 3 | NRFSVAYML (SEQ ID NO: 38) | Chlamydia trachomatis | 1 | 1 |
|   | KRLAETLAL (SEQ ID NO: 93) | Chlamydia trachomatis | | |
|   | DRASFIKNL (SEQ ID NO: 91) | (Kuon) Collagen type VI alpha 2 (C34) | | |
| 4 | SRHHAFCFR (SEQ ID NO: 92) | Aggrecan | 8 | 3 |
|   | ARGQPGVMG (SEQ ID NO: 90) | Collagen type II alpha I | | |
|   | IRSSVQNKL (SEQ ID NO: 94) | Chlamydia trachomatis | | |
| EBV | RRR... | EBV restricted | 6 | 1 |
| Lumican | Lumican | Lumican | 8 | 2 |

Figure 4:
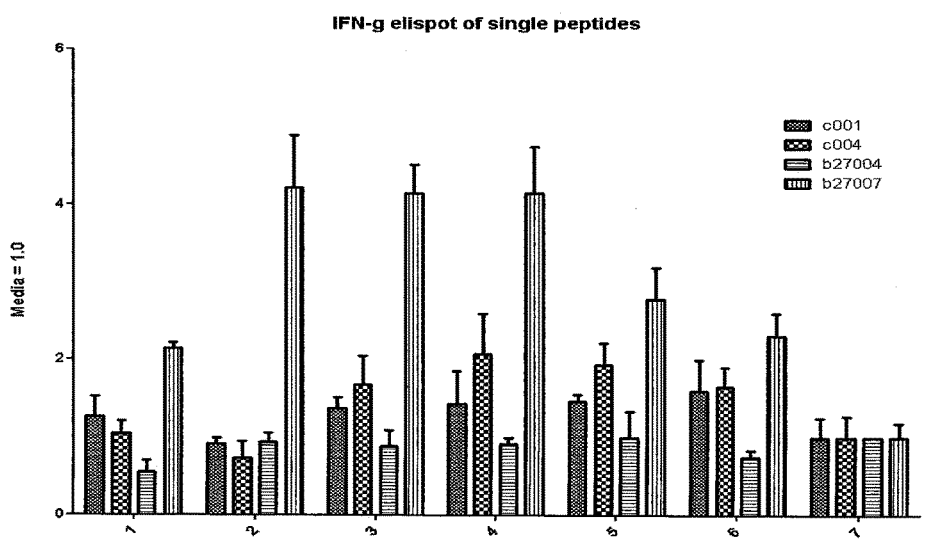
FIG. 4 is a graph showing the results of an Elispot assay measuring IFN-γ responses to six different HLA B27-binding peptides in two patients with acute uveitis (b27004; b27007) and two control subjects (c001 and c004). X-axis: sample/peptide administered. Peptide 1: KRFNALQYL (SEQ ID NO: 2) (Lumican) Peptide 2: LQNNLIETI (SEQ ID NO: 33) (Keratocan/Opticin); Peptide 3: LQYLRLSHN (SEQ ID NO: 34) (Lumican); Peptide 4: QLEDIRLDG (SEQ ID NO: 35) (Opticin); Peptide 5: PLNLRSIDL (SEQ ID NO: 36) (*Chlamydia trachomatis*); Peptide 6: ARKLLLDNL (SEQ ID NO: 37) (*Chlamydia trachomatis*). Y-axis— ratio of spot-forming units (SFU's) (sample vs negative control media). Negative control is by definition 1.0 on the Y-axis.

For 2 patients (B27004 and B27007) six different peptides were tested individually and one HLA B27 subject showed a significant increase in response compared to the controls ($p<0.001$, one way ANOVA, Bonferroni) for three of the peptides (LQNNLIETI (SEQ ID NO: 33) (keratocan/opticin), LQYLRLSHN (SEQ ID NO: 34) (lumican) and QLEDIRLDG (SEQ ID NO: 35) (opticin)) (FIG. 4).

Peptides were divided into four groups based on source (aggrecan, lumican, opticin and *Chlamydia trachomatis*) as follows:
  Lumican peptide mix: KRFNALQYL (SEQ ID NO: 2), LQYLRLSHN (SEQ ID NO: 34)
  Optican peptide mix: LQNNLIETI (SEQ ID NO: 33), QLEDIRLDG (SEQ ID NO: 35)
  *Chlamydia* peptide mix: PLNLRSIDL (SEQ ID NO: 36), ARKLLLDNL (SEQ ID NO: 37), NRFSVAYML (SEQ ID NO: 38)
  Collagen peptide: DRASFIKNL (SEQ ID NO: 91)

Figure 5:
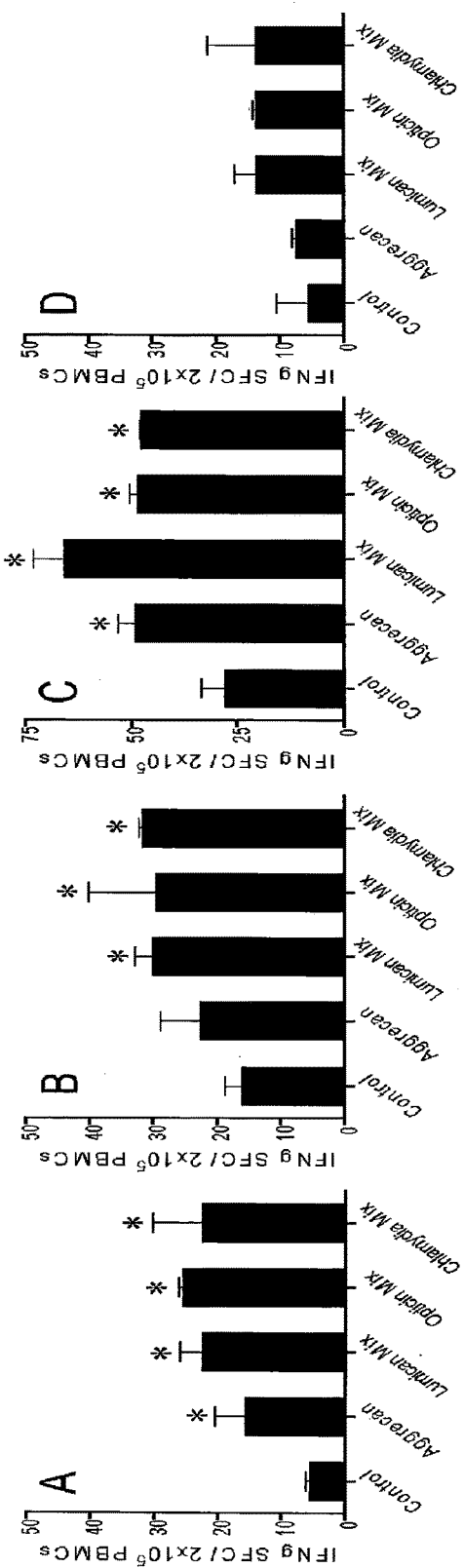
FIG. 5 provides a series of graphs showing PBMC responses to stimulation with peptide mixtures or aggrecan peptide in an EliSpot assay. Interferon-gamma spot forming cells (IFNg SFC) per $2 \times 10^5$ PBMCs are represented as mean+/−SD in duplicates. A positive response (*) to a peptide (or mixture) is defined by the mean SFCs>background+3SD. IFNg secretion was observed from PBMCs of 3 HLA-B27+ AAU patients (A-C) but not from a HLA-B27-normal subject (D). X-axis—sample/peptide mix administered. Y axis—interferon-gamma spot forming cells (IFNγ SFC) per $2 \times 10^5$ PBMCs are represented as mean+/−SD in duplicates.

Three HLA-B27 positive AAU patients and one HLA-B27 negative healthy control showed increased responses to the peptides from the patient compared to the control (FIG. 5).

Discussion

The data provided herein indicates that peptides derived from lumican, opticin and *Chlamydia* are able to bind HLA B2705 with high affinity and may have a role in the pathogenesis of HLA B27 related diseases.

This is the first study to implicate lumican and opticin in the pathogenesis of this group of HLA B27 related diseases. Lumican is an important SLRP, which is widely distributed in mammals. Immunohistochemical results provided herein show that lumican is expressed by iris pigment epithelial cells as well as iris tissue and cartilage. Lumican is also distributed in blood vessels and synovial joints. Thus the distribution of lumican is consistent with the distribution of inflammatory responses associated with HLA B27 diseases, such as the spondyloarthropathies (ankylosing spondylitis and reactive arthritis) and anterior uveitis.

Interestingly, HLA B27 patients showed positive interferon gamma responses to several of the peptides tested in these studies. In addition, they also showed response to lumican indicating that this protein and its peptides play a role in the pathogenesis of HLA B27 related diseases. As previously indicated, the distribution of this peptidoglycan is consistent with the localisation in HLA B27 diseases, which tend to involve synovial joints, cartilage and ocular tissue. Similarly opticin has not previously been implicated in the pathogenesis of these diseases—its distribution, particularly its ocular distribution, may explain disease localisation in patients with HLA B27 diseases. Previous studies have implicated *Chlamydia trachomatis* in the pathogenesis of HLA B27 diseases. This study provides evidence that molecular mimicry between *C. trachomatis* and specific peptide sequences in lumican and opticin may trigger an immune response leading to tissue damage in the characteristic pattern.

This study also shows that patients with HLA B27 acute anterior uveitis mount a T cell mediated immune response to lumican and that lumican has peptide sequences similar to those found in the outer membrane proteins of *C. Trachomatis*. It is postulated that molecular mimicry between lumican and *C. Trachomatis* outer membrane proteins may lead to an immune response generated by a preceding infection by *C. trachomatis*. It is hypothesised that inciting genital infection with *C. trachomatis* leads to a T cell mediated immune response that cross reacts with lumican and localises the inflammatory response in ocular and joint tissues, which is the characteristic pattern of disease observed in patients with SpAs and AU.

Example 3: Administration of Peptides to Lewis Rats

Animals: Lewis rats, age 6 weeks,
day of immunization: 25 Aug. 2011
Peptides were emulsified (sonification) in CFA (50:50, CFA: Peptid) supplemented with M Tuberculosis H37RA (BD, Heidelberg, Germany) to a final concentration of 2.5 mg/ml Peptide is injected s.c. in both hindlegs, 50 µg peptide/200 µl emulsion, 100 µl/leg,
Group size: 6 animals, 3 groups
Group 1 Peptide 1: KRFNALQYL (SEQ ID NO: 2)
Group 2 Peptide 2: ARKLLLDNL (SEQ ID NO: 37)
Group 3 Peptide 3: NRFSVAYML (SEQ ID NO: 38)
7 days post immunization animals were examined daily (eyes and feet)
In all groups, no clinical signs of inflammation were observed until day 25.
On day 15 arthritis was first observed in Group 2
Gr. 1: very mild Arthritis in 2 rats, only observed on day 19/21 in animal 1 (hindleg, right), day 22 (hindleg r/l)
Gr. 2: severe arthritis starting on day 15, animal 2-3,
Animal 1: day 19 H-left, day 22 H-left/right
Animal 2: no arthritis
Animal 3: day 15 H-left/right
Animal 4: very mild day 18 h-left, day 22 h-right, day 24 no arthritis
Animal 5: very mild day 19, h-left
Animal 6: severe day 15 h-left/right, day 18 forefoot-right, day 19 f-left
Gr. 3:
Animal 3: day 15 H-left, day 19 h-right.
Animal 4: mild only on day 21 H-left/right
Animals were sacrificed on day 15.
Eyes were embedded in tissue tec and frozen at −80 degree.
8 µm cryo section were stained with hematoxilin and graded.
Gr. 1: 1-1 l: ret fold (scoring 0.5)
    1-2 r: ret fold,-1-2 l: papillitis? (scoring 0.5/0.5)
Gr. 2 2-3 r: papillitis (scoring 0.5)
    2-5 r: papillitis-2-5 l: vasculitis? (Scoring (0.5/0.5)
    2-6 r: ganglien cells (scoring 0.5)
Gr. 3 3-2 l: papillitis? (scoring 0.5)
    3-3 r: gangl cells (scoring 0.5)
Summary T106 developed arthritis. Preliminary results indicate that peptide 2 generates an arthritis that one would expect in a seronegative type reactive arthritis.

Example 4: Induction of Oral Tolerance with the Peptides P2 (ARKLLLDNL) (SEQ ID NO: 37) and P3 (NRFSVAYML) (SEQ ID NO: 38)

Materials and Methods

Rats were fed 3 times every other day with 200 µg peptide, the control groups received PBS. Three days after the last feeding rats were immunized with the respective peptides. One group was only immunized with CFA-emulsion as a control group for adjuvant arthritis. (see Table 27). Rats were observed daily for clinical evidence of uveitis or arthritis. Animals were euthenased after 3 weeks and histology performed on the eyes and joints of all animals.

Results

Peptide 3-P3 (NRFSVAYML) (SEQ ID NO: 38) induces oral tolerance more effectively than P2 (Table 27).

None of the rats fed with P3 and immunized with P3 developed arthritis or uveitis. The results are summarized in Table 27.

Results show that rats immunized with peptide 3 (P3D7 ie Peptide 3 day 7) more often develop uveitis. With F148_4-3L (P3D7-fed, imm. P3D7) showed cells in the inner plexiform layer, some were apoptotic, F148_4-4R (P3D7-fed, imm. P3D7) has cellular infiltrates in the inner plexiform layer and F148_4-4L (P3D7-fed, imm. P3D7): perivascular infiltrate around a retinal vessel in the gaglion cell/inner plexiform layer. Only the left eye of rat 1-3 (F148_1-3L, PBS-fed, imm. P2D6) showed a big lesion of the posterior retina, reaching the inner nuclear layer, thus resulting in a

TABLE 26

| group | animals | peptide | peptide/animal | clin uveitis | histol Average | incidence | Arthritis Total | Arthritis day 25 |
|---|---|---|---|---|---|---|---|---|
| 1 | 6 Lew | P1 | 50 µg | 0 | 0.125 | 3/12 | 3 | 0 |
| 2 | 6 Lew | P2 | 50 µg | 0 | 0.181 | 5/11* | 8 | 8 |
| 3 | 6 Lew | P3 | 50 µg | 0 | 0.083 | 2/12 | 4 | 2 |

*2-3 left eye, bad staining, no scoring

The three peptides above were generated and administered to mice. The mice were not HLA-B27 transgenics. Peptide 2 generated arthritis in 5/6 animals immunised. Two of these animals had quite severe arthritis in a pattern seen in this model with seronegative arthritis. In addition a group of 6 Lewis rats were immunised with Lumican and all histological score of 2-3 for affecting a large region of the retina.

All effected joints showed evidence of acute inflammation and synovitis. None of the animals who received P3 had evidence of arthritis or uveitis.

TABLE 27

Summary of oral tolerance experiments

| Group/animals | oral tolerogen | | Immunized with | | incidence | affected joints | average score/animal |
|---|---|---|---|---|---|---|---|
| 1/ 4 rats | PBS | 0.5 ml | 3 x 100 µg P2 | 100 µl/ hindleg | 2/4 | 3 | 1.875 |
| 2/ 4 rats | P2 (ARKLLLDNL) (SEQ ID NO: 37) | 200 µg/0.5 ml PBS | 3 x 100 µg P2 | 100 µl/ hindleg | 1/4 (2.?) | 4 + tail (2x) | 3.25 |
| 3/ 4 rats | PBS | 0.5 ml | 3 x 100 µg P3 | 100 µl/ hindleg | 3/4 | 10 | 2.75-3.00 |
| 4/ 4 rats | P3 (NRFSVAYML) (SEQ ID NO: 38) | 200 µg/0.5 ml PBS | 3 x 100 µg P3 | 100 µl/ hindleg | 0/4 | 0 | 0 |
| 5/ 4 rats | | | CFA | 100 µl/ hindleg | 1/4 | 2 | 1 |

Example 5: Serology of *Chlamydia trachomatis*

Materials and Methods

Serology studies were undertaken using a recombinant enzyme-linked immunosorbant assay (ELISA) for the quantitative detection of specific IgG to genus-wide chlamydial LPS in human serum. This is based on an exclusively *Chlamydia*-specific fragment from the LPS which has not been found in any other bacterial LPS.

Sera were diluted 1:100 with sample diluent. 50 µL of the negative control, positive control and the diluted patient samples were pipetted in duplicate into the wells of the 96 well microplate as well as sample diluent as blank. The microplate wells were incubated for 60 minutes (37 C.°, 5% $CO_2$). After incubation the microplate wells were washed three times with 200 µL wash buffer per well. After washing the microplate was tapped on filter paper. 50 µL conjugated antibody was pipetted into each well and allowed to incubated for 60 minutes (37 C.°, 5% $CO_2$). After incubation the wells were washed three times with 200 µL wash buffer per well and the microplated tapped on filter paper. 50 µL TMB-substrate was added per well and the microplate was allowed to incubate in the dark for 30 minutes (37 C.°, 5% $CO_2$). Positive samples turn blue. The reaction was subsequently stopped with the addition of 100 µL stop solution per well.

Results 165 patients with anterior uveitis (AU) were examined of whom 31% had positive serology (25% HLAB27 +ve and 41% HLAB27 –ve), this is significantly higher than the community control population.

Example 6: Peptide-Specific CD4+ T Cells (*Chlamydia* and Lumican) in HLAB2+ Patients Materials and Methods A protocol involving whole blood was used to examine the activated CD4+ and CD8+ T cell responses to antigens (peptides 1-7: see Table 28). With respect to examining the activation of CD4+ T cell responses, the protocol was developed based on the method developed by Zaunders et al. (Zaunders et al., 2009, "High levels of human antigen-specific CD4+ T cells in peripheral blood revealed by stimulated coexpression of CD25 and CD134 (OX40)", J. Immunol. 183(4): 2827-36). This involves stimulating whole blood with antigen (peptide) or mitogen and then measuring cell surface expression of CD25 and CD134 (OX40). In order to determine the activity of CD8+ T cells the expression of cell surface markers CD25, CD38, CD137 and HLA-DR were measured.

Whole blood was collected in lithium-heparin vacutainer tubes. 250 µL of blood was transferred to a well in a 24-well plate and mixed with an equal amount of culture media. Antigens were added and the plate was allowed to incubate for 40-48 hours (37° C., 5% $CO_2$). After incubation, 200 µL blood/media mixture was transferred from each well into two separate 12×75 mm FACS tubes. One tube would be used to stain with antibodies examining CD4 activation, while the other would be stained with antibodies examining CD8 activation. Antibodies for each panel were mixed together. The antibody mixture was added to each tube. Once antibody was added the tube was gently vortexed and allowed to incubate for 15 minutes at room temperature in the dark. 2 mL FACS lysing solution was then added, gently vortexed and incubated for ten minutes at room temperature in the dark. After centrifugation (300 g, 5 minutes), supernatant was decanted followed by a wash with 2 mL wash buffer. After supernatant was decanted 350 µL BD PBS was added and stored at 2°-8° C. in the dark until analysed on FACS Flow Cytometer. The negative control was whole blood in media without any antigen. Staphylococcal enterotoxin B (SEB), a superantigen, was used as a positive control.

Results

Figure 8:
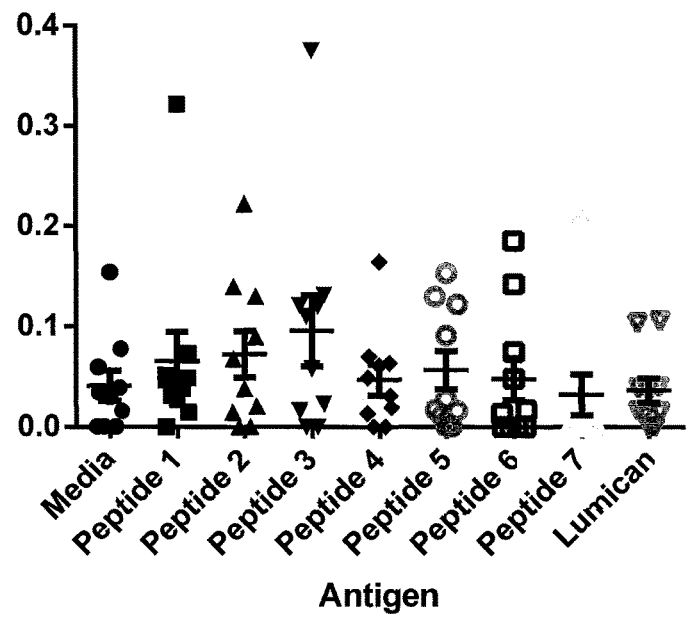
FIG. 8 is a graph showing the percentage of CD4+ T cells in peripheral blood of HLAB27 patients specific for *Chlamydia* and Lumican peptides.

The data shows that patients have peptide-specific CD4+ T cells in their peripheral blood to the *Chlamydia* peptides. These results show that 50% of the HLAB27 patients with AU have CD4+ T cells that recognise the respective *Chlamydia* and Lumican peptides (FIG. 8). These correspond to the patients with positive serology. The responding CD4+ T cells are in low concentration in peripheral blood and would be expected to be in higher concentrations in the inflamed ocular tissue.

TABLE 28

Sequences of peptide antigens administered to blood of HLAB27+ patients

| Peptide No. | Sequence | Peptide Source |
|---|---|---|
| 1 | KRLAETLAL (SEQ ID NO: 93) | *Chlamydia trachomatis* |
| 2 | ARKLLLDNL (SEQ ID NO: 37) | *Chlamydia trachomatis* |
| 3 | IRSSVQNKL (SEQ ID NO: 94) | *Chlamydia trachomatis* |
| 4 | KRFNALQYL (SEQ ID NO: 2) | Human Lumican |
| 5 | LQYLRLSHN (SEQ ID NO: 34) | Human Lumican |
| 6 | NRFSVAYML (SEQ ID NO: 38) | *Chlamydia trachomatis* |
| 7 | PLNLRSIDL (SEQ ID NO: 36) | *Chlamydia trachomatis* |

Lumican Human Lumican Protein Human Lumican Protein

The invention claimed is:

1. A method for detecting the presence or absence of an immune cell or antibody in a subject comprising:
   contacting a biological sample obtained from the subject with a polypeptide, wherein the polypeptide consists of SEQ ID NO: 2 (KRFNALQYL) or SEQ ID NO: 3 (KRFNALQCL); and
   detecting the presence or absence of a binding interaction between the polypeptide and an immune cell or antibody in said sample.

2. The method of claim 1, further comprising determining the human leukocyte antigen type (HLA-type) of the subject.

3. The method of claim 1, wherein said detecting comprises:
   (i) analysing antibody binding by enzyme-linked immunosorbent assay (ELISA),
   (ii) analysing cell proliferation,
   (iii) analysing cytokine synthesis, or
   (iv) analysing cell surface marker expression.

4. The method of claim 1, wherein the polypeptide sequence is KRFNALQYL, as set forth in SEQ ID NO: 2.

5. The method of claim 1, wherein said polypeptide is KRFNALQCL, as set forth in SEQ ID NO: 3.

* * * * *

SEQUENCE LISTING

<160> NUMBER OF SEQ ID NOS: 94

<210> SEQ ID NO 1
<211> LENGTH: 338
<212> TYPE: PRT
<213> ORGANISM: Homo sapiens

<400> SEQUENCE: 1

```
Met Ser Leu Ser Ala Phe Thr Leu Phe Leu Ala Leu Ile Gly Gly Thr
1               5                   10                  15

Ser Gly Gln Tyr Tyr Asp Tyr Asp Phe Pro Leu Ser Ile Tyr Gly Gln
                20                  25                  30

Ser Ser Pro Asn Cys Ala Pro Glu Cys Asn Cys Pro Glu Ser Tyr Pro
            35                  40                  45

Ser Ala Met Tyr Cys Asp Glu Leu Lys Leu Lys Ser Val Pro Met Val
    50                  55                  60

Pro Pro Gly Ile Lys Tyr Leu Tyr Leu Arg Asn Asn Gln Ile Asp His
65                  70                  75                  80

Ile Asp Glu Lys Ala Phe Glu Asn Val Thr Asp Leu Gln Trp Leu Ile
                85                  90                  95

Leu Asp His Asn Leu Leu Glu Asn Ser Lys Ile Lys Gly Arg Val Phe
                100                 105                 110

Ser Lys Leu Lys Gln Leu Lys Lys Leu His Ile Asn His Asn Asn Leu
            115                 120                 125

Thr Glu Ser Val Gly Pro Leu Pro Lys Ser Leu Glu Asp Leu Gln Leu
    130                 135                 140

Thr His Asn Lys Ile Thr Lys Leu Gly Ser Phe Glu Gly Leu Val Asn
145                 150                 155                 160

Leu Thr Phe Ile His Leu Gln His Asn Arg Leu Lys Glu Asp Ala Val
                165                 170                 175

Ser Ala Ala Phe Lys Gly Leu Lys Ser Leu Glu Tyr Leu Asp Leu Ser
            180                 185                 190

Phe Asn Gln Ile Ala Arg Leu Pro Ser Gly Leu Pro Val Ser Leu Leu
    195                 200                 205

Thr Leu Tyr Leu Asp Asn Asn Lys Ile Ser Asn Ile Pro Asp Glu Tyr
210                 215                 220

Phe Lys Arg Phe Asn Ala Leu Gln Tyr Leu Arg Leu Ser His Asn Glu
225                 230                 235                 240

Leu Ala Asp Ser Gly Ile Pro Gly Asn Ser Phe Asn Val Ser Ser Leu
                245                 250                 255

Val Glu Leu Asp Leu Ser Tyr Asn Lys Leu Lys Asn Ile Pro Thr Val
            260                 265                 270

Asn Glu Asn Leu Glu Asn Tyr Tyr Leu Glu Val Asn Gln Leu Glu Lys
    275                 280                 285

Phe Asp Ile Lys Ser Phe Cys Lys Ile Leu Gly Pro Leu Ser Tyr Ser
290                 295                 300

Lys Ile Lys His Leu Arg Leu Asp Gly Asn Arg Ile Ser Glu Thr Ser
305                 310                 315                 320

Leu Pro Pro Asp Met Tyr Glu Cys Leu Arg Val Ala Asn Glu Val Thr
                325                 330                 335

Leu Asn
```

<210> SEQ ID NO 2
<211> LENGTH: 9
<212> TYPE: PRT
<213> ORGANISM: Artificial Sequence
<220> FEATURE:
<223> OTHER INFORMATION: Lumican protein fragment

<400> SEQUENCE: 2

```
Lys Arg Phe Asn Ala Leu Gln Tyr Leu
1               5
```

```
<210> SEQ ID NO 3
<211> LENGTH: 9
<212> TYPE: PRT
<213> ORGANISM: Artificial Sequence
<220> FEATURE:
<223> OTHER INFORMATION: Lumican protein fragment with cystine
<220> FEATURE:
<221> NAME/KEY: MOD_RES
<222> LOCATION: (8)..(8)
<223> OTHER INFORMATION: Cys at position 8

<400> SEQUENCE: 3

Lys Arg Phe Asn Ala Leu Gln Cys Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Lumican protein fragment with leucine
<220> FEATURE:
<221> NAME/KEY: MISC_FEATURE
<222> LOCATION: (8)..(8)
<223> OTHER INFORMATION: Leu at position 8

<400> SEQUENCE: 4

Lys Arg Phe Asn Ala Leu Gln Leu Leu
1               5

<210> SEQ ID NO 5
<211> LENGTH: 348
<212> TYPE: PRT
<213> ORGANISM: Chlamydia trachomatis

<400> SEQUENCE: 5

Met Thr Thr Ile Phe Asp Leu Leu Gly Lys Asp Ala Asp Tyr Leu Leu
1               5                   10                  15

Asn His Lys Cys Val Ile Lys Lys Glu Ala Leu Thr Leu Pro Ser Gly
            20                  25                  30

Asp Leu Val Ser Arg Val Phe Ala Glu Ser Asp Arg Asn Asn Arg Val
        35                  40                  45

Leu Arg Ser Leu Gln Gln Met Phe Ser Cys Gly Arg Leu Gly Gly Thr
    50                  55                  60

Gly Tyr Leu Ser Ile Leu Pro Val Asp Gln Gly Val Glu His Thr Ala
65                  70                  75                  80

Gly Ala Ser Phe Ala Lys Asn Pro Met Tyr Phe Asp Pro Glu Asn Ile
                85                  90                  95

Val Arg Leu Ala Met Glu Ala Gly Cys Ser Ala Val Ala Ser Ser Tyr
            100                 105                 110

Gly Val Leu Ser Ile Leu Ala Arg Arg Tyr Ala His Lys Ile Pro Phe
        115                 120                 125

Leu Leu Lys Leu Asn His Asn Glu Leu Leu Ser Tyr Pro Thr Thr Tyr
    130                 135                 140

His Gln Ile Phe Phe Ser Gln Val Glu Asp Ala Tyr Asn Met Gly Ala
145                 150                 155                 160

Val Ala Val Gly Ala Thr Ile Tyr Phe Gly Ser Glu Ser Ser Ser Glu
                165                 170                 175

Glu Ile Val Ala Val Ala Glu Ala Phe Ala Arg Ala Arg Glu Leu Gly
            180                 185                 190

Leu Ala Thr Val Leu Trp Cys Tyr Leu Arg Asn Pro His Phe Val Val
```

```
            195                 200                 205
Asn Asn Val Asp Tyr His Thr Ala Ala Asp Leu Thr Gly Gln Ala Asp
    210                 215                 220
His Leu Gly Ala Thr Leu Gly Ala Asp Ile Val Lys Gln Lys Leu Pro
225                 230                 235                 240
Thr Leu Gln Gly Gly Phe Lys Thr Ile Asn Phe Ser Lys Thr Asp Asp
                245                 250                 255
Leu Val Tyr Ser Glu Leu Ser Ser Asn His Pro Ile Asp Leu Cys Arg
            260                 265                 270
Tyr Gln Val Leu Asn Ser Tyr Cys Gly Lys Val Gly Leu Ile Asn Ser
        275                 280                 285
Gly Gly Pro Ser Gly Gln Asp Asp Phe Ala Glu Ala Val Lys Thr Ala
    290                 295                 300
Val Ile Asn Lys Arg Ala Gly Gly Met Gly Leu Ile Leu Gly Arg Lys
305                 310                 315                 320
Ala Phe Gln Arg Pro Phe Ser Glu Gly Val Arg Leu Leu Asn Leu Ile
                325                 330                 335
Gln Asp Ile Tyr Leu Asp Pro Thr Ile Ser Ile Ser
            340                 345

<210> SEQ ID NO 6
<211> LENGTH: 792
<212> TYPE: PRT
<213> ORGANISM: Chlamydia trachomatis

<400> SEQUENCE: 6

Met Leu Gly Ile Arg Lys Lys Thr Ile Leu Gln Leu Ala Val Leu Leu
1               5                   10                  15
Leu Leu Thr Phe Ser Arg Ser Ser Phe Cys Ser Thr Ser Glu Gly Arg
            20                  25                  30
Met Val Val Glu Ser Ile Thr Ile Thr Thr Gln Gly Glu Asn Thr Gln
        35                  40                  45
Asn Lys Arg Ala Ile Pro Lys Ile Lys Thr Lys Gln Gly Thr Leu Phe
    50                  55                  60
Ser Gln Ala Asp Phe Asp Glu Asp Leu Arg Thr Leu Ser Lys Asp Phe
65                  70                  75                  80
Asp Arg Val Glu Pro Ile Val Glu Phe Arg Asn Gly Gln Ala Val Ile
                85                  90                  95
Ser Leu Ile Leu Thr Ala Lys Pro Val Ile Arg Glu Ile Asn Ile Ser
            100                 105                 110
Gly Asn Glu Ala Ile Pro Thr His Lys Ile Leu Lys Thr Leu Glu Leu
        115                 120                 125
Tyr Lys Asn Asp Leu Phe Asp Arg Glu Leu Phe Phe Lys Asn Phe Asp
    130                 135                 140
Ala Leu Arg Thr Leu Tyr Leu Lys Arg Gly Tyr Tyr Asp Ser Gln Leu
145                 150                 155                 160
Ser Tyr Ser His Asn His Asn Glu Lys Glu Gly Phe Ile Asp Ile Ser
                165                 170                 175
Ile Glu Ile Lys Glu Gly Arg His Gly Arg Ile Lys Lys Leu Thr Ile
            180                 185                 190
Ser Gly Ile Thr Arg Thr Glu Ala Ser Asp Leu Gly Asp Ile Val Leu
        195                 200                 205
Thr Lys Gln Tyr Ser Thr Thr Ser Trp Phe Thr Gly Ala Gly Val
    210                 215                 220
```

```
Tyr His Pro Asp Met Val Glu Gln Asp Leu Phe Ala Ile Thr Asn Tyr
225                 230                 235                 240

Phe Gln Asn Lys Gly Tyr Ala Asp Ala Lys Val Ser Lys Glu Val Ser
            245                 250                 255

Thr Asp Ala Lys Gly Asn Ile Thr Leu Leu Ile Val Asp Lys Gly
        260                 265                 270

Pro Leu Tyr Thr Leu Gly His Val His Ile Glu Gly Phe Thr Ala Leu
        275                 280                 285

Ser Lys Arg Leu Leu Asp Lys Gln Leu Leu Val Gly Pro Asn Ser Leu
    290                 295                 300

Tyr Cys Pro Asp Lys Ile Trp Thr Gly Ala Gln Lys Ile Arg Ser Ala
305                 310                 315                 320

Tyr Ala Arg Tyr Gly Tyr Val Asn Thr Asn Val Asp Val Ser Phe Ser
            325                 330                 335

Ala His Pro Thr Leu Pro Val Tyr Asp Val Thr Tyr Arg Val Ser Glu
        340                 345                 350

Gly Ser Ser Tyr Lys Ile Gly Leu Ile Lys Ile Lys Gly Asn Thr His
        355                 360                 365

Thr Lys His Asp Val Ile Leu His Glu Thr Ser Leu Phe Pro Gly Asp
    370                 375                 380

Thr Phe Asp Arg Leu Lys Leu Glu Gly Thr Glu Thr Arg Leu Arg Asn
385                 390                 395                 400

Thr Gly Tyr Phe Lys Ser Val Ser Val Tyr Thr Val His Ser Gln Leu
            405                 410                 415

Asp Pro Leu Asp Ser Asn Asp Leu Tyr Arg Asp Val Phe Ile Glu Val
        420                 425                 430

Lys Glu Thr Glu Thr Gly Asn Leu Gly Leu Phe Leu Gly Phe Ser Ser
        435                 440                 445

Ile Asp His Leu Phe Gly Gly Ala Glu Ile Ala Glu Ser Asn Phe Asp
    450                 455                 460

Leu Phe Gly Ala Arg Asn Phe Leu Lys Lys Gly Phe Lys Ser Leu Arg
465                 470                 475                 480

Gly Gly Gly Glu Tyr Leu Phe Leu Lys Ala Asn Leu Gly Asp Lys Val
            485                 490                 495

Thr Asp Tyr Thr Val Lys Trp Thr Lys Pro His Phe Leu Asn Thr Pro
        500                 505                 510

Trp Ile Leu Gly Val Glu Leu Asp Lys Ser Ile Asn Lys Ala Leu Ser
    515                 520                 525

Lys Asp Tyr Ser Val Asp Thr Tyr Gly Gly Asn Ile Ser Thr Thr Tyr
530                 535                 540

Ile Leu Asn Asp Lys Leu Lys Tyr Gly Met Tyr Tyr Arg Gly Ser Gln
545                 550                 555                 560

Thr Ser Leu Ser Leu Arg Lys Lys Thr Ser Ser Ser Asn Arg Pro Gly
            565                 570                 575

Pro Asp Leu Asp Ser Asn Lys Gly Phe Val Ser Ala Ala Gly Leu Asn
        580                 585                 590

Val Leu Tyr Asp Ser Ile Asp Asn Pro Arg Lys Pro Thr Met Gly Ile
        595                 600                 605

Arg Ser Ser Leu Asn Phe Glu Leu Ser Gly Leu Gly Thr Tyr Gln
    610                 615                 620

Phe Thr Lys Leu Thr Ala Ser Gly Ser Ile Tyr Arg Leu Leu Thr Lys
625                 630                 635                 640

Lys Gly Val Leu Lys Val Arg Ala Glu Ala Lys Phe Ile Lys Pro Phe
```

```
                    645                 650                 655
Gly Thr Thr Thr Ala Gln Gly Ile Pro Val Ser Glu Arg Phe Phe Leu
                660                 665                 670

Gly Gly Glu Thr Thr Val Arg Gly Tyr Lys Pro Phe Ile Ile Gly Pro
                675                 680                 685

Lys Phe Ser Pro Thr Glu Pro Gln Gly Gly Leu Ser Ser Leu Leu Leu
                690                 695                 700

Thr Glu Glu Phe Gln Tyr Pro Leu Ile Ser Gln Pro Cys Ile Asn Ala
705                 710                 715                 720

Phe Val Phe Leu Asp Ser Gly Phe Ile Gly Ile Glu Glu Tyr Thr Ile
                725                 730                 735

Arg Leu Lys Asp Leu Cys Ser Ser Ala Gly Phe Gly Leu Arg Phe Asp
                740                 745                 750

Met Met Asn Asn Val Pro Ile Met Leu Gly Trp Gly Trp Pro Phe Arg
                755                 760                 765

Pro Thr Glu Ile Leu Asn Asn Glu Lys Ile Asp Val Ser Gln Arg Phe
                770                 775                 780

Phe Phe Ala Leu Gly Gly Val Phe
785                 790

<210> SEQ ID NO 7
<211> LENGTH: 497
<212> TYPE: PRT
<213> ORGANISM: Chlamydia trachomatis

<400> SEQUENCE: 7

Met Met Lys Arg Leu Leu Cys Val Leu Leu Ser Thr Ser Val Phe Ser
1                   5                   10                  15

Ser Pro Met Leu Gly Tyr Ser Ala Ser Lys Lys Asp Ser Lys Ala Asp
                20                  25                  30

Ile Cys Leu Ala Val Ser Ser Gly Asp Gln Glu Val Ser Gln Glu Asp
                35                  40                  45

Leu Leu Lys Glu Val Ser Arg Gly Phe Ser Arg Val Ala Ala Lys Ala
        50                  55                  60

Thr Pro Gly Val Val Tyr Ile Glu Asn Phe Pro Lys Thr Gly Asn Gln
65                  70                  75                  80

Ala Ile Ala Ser Pro Gly Asn Lys Arg Gly Phe Gln Glu Asn Pro Phe
                85                  90                  95

Asp Tyr Phe Asn Asp Glu Phe Phe Asn Arg Phe Phe Gly Leu Pro Ser
                100                 105                 110

His Arg Glu Gln Gln Arg Pro Gln Gln Arg Asp Ala Val Arg Gly Thr
                115                 120                 125

Gly Phe Ile Val Ser Glu Asp Gly Tyr Val Val Thr Asn His His Val
        130                 135                 140

Val Glu Asp Ala Gly Lys Ile His Val Thr Leu His Asp Gly Gln Lys
145                 150                 155                 160

Tyr Thr Ala Lys Ile Val Gly Leu Asp Pro Lys Thr Asp Leu Ala Val
                165                 170                 175

Ile Lys Ile Gln Ala Glu Lys Leu Pro Phe Leu Thr Phe Gly Asn Ser
                180                 185                 190

Asp Gln Leu Gln Ile Gly Asp Trp Ala Ile Ala Ile Gly Asn Pro Phe
                195                 200                 205

Gly Leu Gln Ala Thr Val Thr Val Gly Val Ile Ser Ala Lys Gly Arg
        210                 215                 220
```

-continued

Asn Gln Leu His Ile Val Asp Phe Glu Asp Phe Ile Gln Thr Asp Ala
225                 230                 235                 240

Ala Ile Asn Pro Gly Asn Ser Gly Gly Pro Leu Leu Asn Ile Asn Gly
            245                 250                 255

Gln Val Ile Gly Val Asn Thr Ala Ile Val Ser Gly Ser Gly Gly Tyr
        260                 265                 270

Ile Gly Ile Gly Phe Ala Ile Pro Ser Leu Met Ala Lys Arg Val Ile
    275                 280                 285

Asp Gln Leu Ile Ser Asp Gly Gln Val Thr Arg Gly Phe Leu Gly Val
290                 295                 300

Thr Leu Gln Pro Ile Asp Ser Glu Leu Ala Thr Cys Tyr Lys Leu Glu
305                 310                 315                 320

Lys Val Tyr Gly Ala Leu Val Thr Asp Val Val Lys Gly Ser Pro Ala
                325                 330                 335

Glu Lys Ala Gly Leu Arg Gln Glu Asp Val Ile Val Ala Tyr Asn Gly
            340                 345                 350

Lys Glu Val Glu Ser Leu Ser Ala Leu Arg Asn Ala Ile Ser Leu Met
        355                 360                 365

Met Pro Gly Thr Arg Val Val Leu Lys Ile Val Arg Glu Gly Lys Thr
    370                 375                 380

Ile Glu Ile Pro Val Thr Val Thr Gln Ile Pro Thr Glu Asp Gly Val
385                 390                 395                 400

Ser Ala Leu Gln Lys Met Gly Val Arg Val Gln Asn Ile Thr Pro Glu
                405                 410                 415

Ile Cys Lys Lys Leu Gly Leu Ala Ala Asp Thr Arg Gly Ile Leu Val
            420                 425                 430

Val Ala Val Glu Ala Gly Ser Pro Ala Ala Ser Ala Gly Val Ala Pro
        435                 440                 445

Gly Gln Leu Ile Leu Ala Val Asn Arg Gln Arg Val Ala Ser Val Glu
    450                 455                 460

Glu Leu Asn Gln Val Leu Lys Asn Ser Lys Gly Glu Asn Val Leu Leu
465                 470                 475                 480

Met Val Ser Gln Gly Asp Val Val Arg Phe Ile Val Leu Lys Ser Asp
                485                 490                 495

Glu

<210> SEQ ID NO 8
<211> LENGTH: 674
<212> TYPE: PRT
<213> ORGANISM: Emericella nidulans

<400> SEQUENCE: 8

Met Gly Asp Arg Leu Pro Phe Glu Val Leu Leu His Ile Ala Glu Cys
1               5                   10                  15

Leu Glu Glu Asp Arg Asp Ser Leu Val Gln Cys Thr Arg Val Cys Thr
            20                  25                  30

Arg Trp Lys Ala Val Phe Glu Arg Leu Leu Tyr Arg Arg Leu His Val
        35                  40                  45

Leu Ser Asn Asp Leu Gly Val Ser Val Gly Asp Leu Ser Leu Thr Arg
    50                  55                  60

Phe Gln Ala Leu Thr Ser Ala Ala Gly Thr Ala Arg Arg Ser Tyr Ile
65                  70                  75                  80

Lys His Leu Ile Tyr His Ile Val Leu Pro Tyr Asp Val Gly Ala Trp
                85                  90                  95

```
Pro Gly Asp Thr Pro Asp Gly Glu Ala Asn Pro Phe Gln Lys Ala Asn
            100                 105                 110

Asp Ala Val Phe Gly Val Ala Val Ile Ser Leu Phe Thr Ala Leu Leu
        115                 120                 125

Ser Trp Glu Asn Thr Arg Phe Lys Leu Thr Phe Gln Leu Val Gly Cys
    130                 135                 140

Leu Asp Ser Tyr Glu Leu Gly Met Glu Glu Thr Ser Val Asp Gly Leu
145                 150                 155                 160

Glu Glu Glu Ser Ile Pro Pro Tyr Gln Ala Arg Leu Pro Ser Ile
                165                 170                 175

Glu Leu Phe Glu Leu Pro Glu Ile Glu Ser Ile Asp Lys Phe Phe Val
            180                 185                 190

Ser Asp Tyr Leu Leu Gly Ser Val Gly Ile Gly Asn Arg Thr Ala Ile
        195                 200                 205

Glu Ile Ala His Cys Phe Pro Lys Leu Gln Ser Leu Glu Leu Ser Leu
    210                 215                 220

Ile Thr His Asp Asp Pro Asp Phe Gln Ile Asn Ser Arg Lys Glu Leu
225                 230                 235                 240

Ile Gln Gly Ile Lys Lys Leu Pro Pro Thr Leu Lys Thr Phe Arg Tyr
                245                 250                 255

Ser Glu His Tyr Ser Glu Phe Ile Asp Arg Glu Leu Gln Ser Val Asp
            260                 265                 270

Phe Leu Leu Gly Glu Ser Asp Met Leu Thr Pro Thr Leu Arg Glu Phe
        275                 280                 285

Ser Leu Gln Leu Arg Glu Leu Lys Leu Ile Gly Val Ala Ile Ala Pro
    290                 295                 300

Asp Leu Leu Trp Pro Leu Asp Gln Met Gly Glu Pro Ser Ser Ser Thr
305                 310                 315                 320

Thr Glu Val Phe Trp Pro His Leu Glu Thr Ile Glu Leu Cys Pro Ala
                325                 330                 335

Gln Tyr Leu Pro Thr Ala Met Gly Tyr Ala Ala Arg His Met Pro Arg
            340                 345                 350

Leu Thr Ser Ile Val Tyr Cys Ala Leu Phe Glu Glu Ala Tyr Phe Thr
        355                 360                 365

Arg Phe Asn Phe Leu Gln Tyr Leu Ser Lys Arg Thr Gly Ile Arg Lys
    370                 375                 380

Gly Met Leu Arg Asn Ser Gly Ala Pro Leu His Gly Gln Leu Arg Gly
385                 390                 395                 400

Gly His Glu Glu Lys Leu Ala Thr Arg Glu Leu Leu Ser Ser Lys Ala
                405                 410                 415

His Leu Leu Arg Gly Leu Gly Asn Cys Ala Arg Ser Phe Glu Glu Ser
            420                 425                 430

Gly Leu Thr Ala Arg Ser Ile Arg Ser Arg Ala Gln Leu Ala Lys Gln
        435                 440                 445

Tyr Arg Ala Arg His Leu Leu Cys Thr Arg Asp Thr Asp Val Ser
    450                 455                 460

Lys Thr Asp His Lys Cys Ser Glu Asp Tyr Thr Leu Ser Thr Ser Glu
465                 470                 475                 480

Ser Gly Asp Leu Arg Tyr His Gln Arg Ala Val Ser Arg Arg Ala Ser
                485                 490                 495

Ser Cys Leu Lys Ser Thr Ile Gly Glu Met Lys Ile Ile Val Cys Val
            500                 505                 510

Leu Asn Pro Gln Gly Glu Thr Asp Gln Ala Gly Val Pro Val Val Leu
```

```
                515                 520                 525

Asp Leu Gln Phe Val Asp Val Ser Thr Cys Gln Pro Ile Glu Gly Ile
    530                 535                 540

Tyr Ala Glu Thr Trp Asn Cys Asn Ala Thr Gly Val Tyr Ser Gly Ala
545                 550                 555                 560

Gln Gly Asn Gly Asn Gly Asn Ser Glu Asp Ser Ile Leu Gln Glu
                565                 570                 575

Thr Phe Leu Arg Arg Val Ser Lys Thr Gly Glu Glu Gly Val Val Thr
    580                 585                 590

Phe Asn Thr Leu Phe Pro Gly His Tyr Ala Gly Arg Ala Thr His Tyr
            595                 600                 605

His Val Leu Ala His Leu Asp Ala Ala Leu Leu Glu Asn Asn Thr Leu
    610                 615                 620

Thr Gly Gly Ser Val Pro His Ile Gly Gln Leu Phe Phe Asp Gln Asp
625                 630                 635                 640

Leu Ile Thr Ala Val Glu Val Thr Ser Pro Tyr Ser Ser Asn Thr Val
                645                 650                 655

Glu Ile Thr Lys Asn Thr Glu Asp Ser Pro Val Gly Thr Cys Ser Leu
            660                 665                 670

Ser Ser

<210> SEQ ID NO 9
<211> LENGTH: 8
<212> TYPE: PRT
<213> ORGANISM: Artificial Sequence
<220> FEATURE:
<223> OTHER INFORMATION: An 8 amino acid lumican binding protein

<400> SEQUENCE: 9

Arg Phe Asn Ala Leu Gln Tyr Leu
1               5

<210> SEQ ID NO 10
<211> LENGTH: 7
<212> TYPE: PRT
<213> ORGANISM: Artificial Sequence
<220> FEATURE:
<223> OTHER INFORMATION: Short lumican binding protein

<400> SEQUENCE: 10

Phe Asn Ala Leu Gln Tyr Leu
1               5

<210> SEQ ID NO 11
<211> LENGTH: 6
<212> TYPE: PRT
<213> ORGANISM: Artificial Sequence
<220> FEATURE:
<223> OTHER INFORMATION: Second short lumican binding protein

<400> SEQUENCE: 11

Asn Ala Leu Gln Tyr Leu
1               5

<210> SEQ ID NO 12
<211> LENGTH: 8
<212> TYPE: PRT
<213> ORGANISM: Artificial Sequence
<220> FEATURE:
<223> OTHER INFORMATION: Second 8 amino acid lumican binding protein

<400> SEQUENCE: 12
```

Lys Arg Phe Asn Ala Leu Gln Tyr
1               5

<210> SEQ ID NO 13
<211> LENGTH: 7
<212> TYPE: PRT
<213> ORGANISM: Artificial Sequence
<220> FEATURE:
<223> OTHER INFORMATION: Third short lumican binding protein

<400> SEQUENCE: 13

Lys Arg Phe Asn Ala Leu Gln
1               5

<210> SEQ ID NO 14
<211> LENGTH: 6
<212> TYPE: PRT
<213> ORGANISM: Artificial Sequence
<220> FEATURE:
<223> OTHER INFORMATION: Fourth short lumican binding protein

<400> SEQUENCE: 14

Lys Arg Phe Asn Ala Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Fifth short lumican binding protein

<400> SEQUENCE: 15

Arg Phe Asn Ala Leu Gln Tyr
1               5

<210> SEQ ID NO 16
<211> LENGTH: 6
<212> TYPE: PRT
<213> ORGANISM: Artificial Sequence
<220> FEATURE:
<223> OTHER INFORMATION: Sixth short lumican binding protein

<400> SEQUENCE: 16

Arg Phe Asn Ala Leu Gln
1               5

<210> SEQ ID NO 17
<211> LENGTH: 6
<212> TYPE: PRT
<213> ORGANISM: Artificial Sequence
<220> FEATURE:
<223> OTHER INFORMATION: Seventh short lumican binding protein

<400> SEQUENCE: 17

Phe Asn Ala Leu Gln Tyr
1               5

<210> SEQ ID NO 18
<211> LENGTH: 8
<212> TYPE: PRT
<213> ORGANISM: Artificial Sequence
<220> FEATURE:
<223> OTHER INFORMATION: An 8 amino acid lumican polypeptide fragment
<220> FEATURE:
<221> NAME/KEY: MISC_FEATURE
<222> LOCATION: (7)..(7)

```
<223> OTHER INFORMATION: Cys at position 7

<400> SEQUENCE: 18

Arg Phe Asn Ala Leu Gln Cys Leu
1               5

<210> SEQ ID NO 19
<211> LENGTH: 7
<212> TYPE: PRT
<213> ORGANISM: Artificial Sequence
<220> FEATURE:
<223> OTHER INFORMATION: A 7 amino acid lumican polypeptide fragment
<220> FEATURE:
<221> NAME/KEY: MISC_FEATURE
<222> LOCATION: (6)..(6)
<223> OTHER INFORMATION: Cys at position 6

<400> SEQUENCE: 19

Phe Asn Ala Leu Gln Cys Leu
1               5

<210> SEQ ID NO 20
<211> LENGTH: 6
<212> TYPE: PRT
<213> ORGANISM: Artificial Sequence
<220> FEATURE:
<223> OTHER INFORMATION: A 6 amino acid lumican protein fragment
<220> FEATURE:
<221> NAME/KEY: MISC_FEATURE
<222> LOCATION: (5)..(5)
<223> OTHER INFORMATION: Cys at position 5

<400> SEQUENCE: 20

Asn Ala Leu Gln Cys Leu
1               5

<210> SEQ ID NO 21
<211> LENGTH: 8
<212> TYPE: PRT
<213> ORGANISM: Artificial Sequence
<220> FEATURE:
<223> OTHER INFORMATION: An 8 amino acid lumican protein fragment
<220> FEATURE:
<221> NAME/KEY: MISC_FEATURE
<222> LOCATION: (8)..(8)
<223> OTHER INFORMATION: Cys at position 8

<400> SEQUENCE: 21

Lys Arg Phe Asn Ala Leu Gln Cys
1               5

<210> SEQ ID NO 22
<211> LENGTH: 7
<212> TYPE: PRT
<213> ORGANISM: Artificial Sequence
<220> FEATURE:
<223> OTHER INFORMATION: A 7 amino acid lumican protein fragment
<220> FEATURE:
<221> NAME/KEY: MISC_FEATURE
<222> LOCATION: (7)..(7)
<223> OTHER INFORMATION: Cys at position 7

<400> SEQUENCE: 22

Arg Phe Asn Ala Leu Gln Cys
1               5

<210> SEQ ID NO 23
<211> LENGTH: 6
<212> TYPE: PRT
```

```
<213> ORGANISM: Artificial Sequence
<220> FEATURE:
<223> OTHER INFORMATION: A 6 amino acid modified lumican protein
      fragment
<220> FEATURE:
<221> NAME/KEY: MISC_FEATURE
<222> LOCATION: (6)..(6)
<223> OTHER INFORMATION: Cys at position 6

<400> SEQUENCE: 23

Phe Asn Ala Leu Gln Cys
1               5

<210> SEQ ID NO 24
<211> LENGTH: 8
<212> TYPE: PRT
<213> ORGANISM: Artificial Sequence
<220> FEATURE:
<223> OTHER INFORMATION: An 8 amino acid modified lumican protein
      fragment
<220> FEATURE:
<221> NAME/KEY: MISC_FEATURE
<222> LOCATION: (7)..(7)
<223> OTHER INFORMATION: Leu at position 7

<400> SEQUENCE: 24

Arg Phe Asn Ala Leu Gln Leu Leu
1               5

<210> SEQ ID NO 25
<211> LENGTH: 7
<212> TYPE: PRT
<213> ORGANISM: Artificial Sequence
<220> FEATURE:
<223> OTHER INFORMATION: A 7 amino acid modified lumican protein
      fragment
<220> FEATURE:
<221> NAME/KEY: MISC_FEATURE
<222> LOCATION: (6)..(6)
<223> OTHER INFORMATION: Leu at position 6

<400> SEQUENCE: 25

Phe Asn Ala Leu Gln Leu Leu
1               5

<210> SEQ ID NO 26
<211> LENGTH: 6
<212> TYPE: PRT
<213> ORGANISM: Artificial Sequence
<220> FEATURE:
<223> OTHER INFORMATION: A 6 amino acid modified lumican protein
<220> FEATURE:
<221> NAME/KEY: MISC_FEATURE
<222> LOCATION: (5)..(5)
<223> OTHER INFORMATION: Leu at position 5

<400> SEQUENCE: 26

Asn Ala Leu Gln Leu Leu
1               5

<210> SEQ ID NO 27
<211> LENGTH: 8
<212> TYPE: PRT
<213> ORGANISM: Artificial Sequence
<220> FEATURE:
<223> OTHER INFORMATION: An 8 amino acid modified lumican protein
<220> FEATURE:
<221> NAME/KEY: MISC_FEATURE
<222> LOCATION: (8)..(8)
<223> OTHER INFORMATION: Leu at position 8
```

```
<400> SEQUENCE: 27

Lys Arg Phe Asn Ala Leu Gln Leu
1               5

<210> SEQ ID NO 28
<211> LENGTH: 7
<212> TYPE: PRT
<213> ORGANISM: Artificial Sequence
<220> FEATURE:
<223> OTHER INFORMATION: A 7 amino acid modified lumican protein
<220> FEATURE:
<221> NAME/KEY: MISC_FEATURE
<222> LOCATION: (7)..(7)
<223> OTHER INFORMATION: Leu at position 7

<400> SEQUENCE: 28

Arg Phe Asn Ala Leu Gln Leu
1               5

<210> SEQ ID NO 29
<211> LENGTH: 6
<212> TYPE: PRT
<213> ORGANISM: Artificial Sequence
<220> FEATURE:
<223> OTHER INFORMATION: A second 6 amino acid modified lumican protein
<220> FEATURE:
<221> NAME/KEY: MISC_FEATURE
<222> LOCATION: (6)..(6)
<223> OTHER INFORMATION: Leu at position 6

<400> SEQUENCE: 29

Phe Asn Ala Leu Gln Leu
1               5

<210> SEQ ID NO 30
<211> LENGTH: 332
<212> TYPE: PRT
<213> ORGANISM: Homo sapiens

<400> SEQUENCE: 30

Met Arg Leu Leu Ala Phe Leu Ser Leu Leu Ala Leu Val Leu Gln Glu
1               5                   10                  15

Thr Gly Thr Ala Ser Leu Pro Arg Lys Glu Arg Lys Arg Arg Glu Glu
            20                  25                  30

Gln Met Pro Arg Glu Gly Asp Ser Phe Glu Val Leu Pro Leu Arg Asn
        35                  40                  45

Asp Val Leu Asn Pro Asp Asn Tyr Gly Glu Val Ile Asp Leu Ser Asn
    50                  55                  60

Tyr Glu Glu Leu Thr Asp Tyr Gly Asp Gln Leu Pro Glu Val Lys Val
65                  70                  75                  80

Thr Ser Leu Ala Pro Ala Thr Ser Ile Ser Pro Ala Lys Ser Thr Thr
                85                  90                  95

Ala Pro Gly Thr Pro Ser Ser Asn Pro Thr Met Thr Arg Pro Thr Thr
            100                 105                 110

Ala Gly Leu Leu Leu Ser Ser Gln Pro Asn His Gly Leu Pro Thr Cys
        115                 120                 125

Leu Val Cys Val Cys Leu Gly Ser Ser Val Tyr Cys Asp Asp Ile Asp
    130                 135                 140

Leu Glu Asp Ile Pro Pro Leu Pro Arg Arg Thr Ala Tyr Leu Tyr Ala
145                 150                 155                 160

Arg Phe Asn Arg Ile Ser Arg Ile Arg Ala Glu Asp Phe Lys Gly Leu
                165                 170                 175
```

```
Thr Lys Leu Lys Arg Ile Asp Leu Ser Asn Asn Leu Ile Ser Ser Ile
            180                 185                 190

Asp Asn Asp Ala Phe Arg Leu Leu His Ala Leu Gln Asp Leu Ile Leu
            195                 200                 205

Pro Glu Asn Gln Leu Glu Ala Leu Pro Val Leu Pro Ser Gly Ile Glu
210                 215                 220

Phe Leu Asp Val Arg Leu Asn Arg Leu Gln Ser Ser Gly Ile Gln Pro
225                 230                 235                 240

Ala Ala Phe Arg Ala Met Glu Lys Leu Gln Phe Leu Tyr Leu Ser Asp
            245                 250                 255

Asn Leu Leu Asp Ser Ile Pro Gly Pro Leu Pro Leu Ser Leu Arg Ser
            260                 265                 270

Val His Leu Gln Asn Asn Leu Ile Glu Thr Met Gln Arg Asp Val Phe
            275                 280                 285

Cys Asp Pro Glu Glu His Lys His Thr Arg Arg Gln Leu Glu Asp Ile
            290                 295                 300

Arg Leu Asp Gly Asn Pro Ile Asn Leu Ser Leu Phe Pro Ser Ala Tyr
305                 310                 315                 320

Phe Cys Leu Pro Arg Leu Pro Ile Gly Arg Phe Thr
            325                 330

<210> SEQ ID NO 31
<211> LENGTH: 9
<212> TYPE: PRT
<213> ORGANISM: Artificial Sequence
<220> FEATURE:
<223> OTHER INFORMATION: A first opticin protein fragment

<400> SEQUENCE: 31

Leu Gln Asn Asn Leu Ile Glu Thr Met
1               5

<210> SEQ ID NO 32
<211> LENGTH: 352
<212> TYPE: PRT
<213> ORGANISM: Homo sapiens

<400> SEQUENCE: 32

Met Ala Gly Thr Ile Cys Phe Ile Met Trp Val Leu Phe Ile Thr Asp
1               5                   10                  15

Thr Val Trp Ser Arg Ser Val Arg Gln Val Tyr Glu Val His Asp Ser
            20                  25                  30

Asp Asp Trp Thr Ile His Asp Phe Glu Cys Pro Met Glu Cys Phe Cys
            35                  40                  45

Pro Pro Ser Phe Pro Thr Ala Leu Tyr Cys Glu Asn Arg Gly Leu Lys
    50                  55                  60

Glu Ile Pro Ala Ile Pro Ser Arg Ile Trp Tyr Leu Tyr Leu Gln Asn
65                  70                  75                  80

Asn Leu Ile Glu Thr Ile Pro Glu Lys Pro Phe Glu Asn Ala Thr Gln
            85                  90                  95

Leu Arg Trp Ile Asn Leu Asn Lys Asn Lys Ile Thr Asn Tyr Gly Ile
            100                 105                 110

Glu Lys Gly Ala Leu Ser Gln Leu Lys Lys Leu Leu Phe Leu Phe Leu
            115                 120                 125

Glu Asp Asn Glu Leu Glu Glu Val Pro Ser Pro Leu Pro Arg Ser Leu
130                 135                 140
```

```
Glu Gln Leu Gln Leu Ala Arg Asn Lys Val Ser Arg Ile Pro Gln Gly
145                 150                 155                 160

Thr Phe Ser Asn Leu Glu Asn Leu Thr Leu Leu Asp Leu Gln Asn Asn
            165                 170                 175

Lys Leu Val Asp Asn Ala Phe Gln Arg Asp Thr Phe Lys Gly Leu Lys
            180                 185                 190

Asn Leu Met Gln Leu Asn Met Ala Lys Asn Ala Leu Arg Asn Met Pro
        195                 200                 205

Pro Arg Leu Pro Ala Asn Thr Met Gln Leu Phe Leu Asp Asn Asn Ser
        210                 215                 220

Ile Glu Gly Ile Pro Glu Asn Tyr Phe Asn Val Ile Pro Lys Val Ala
225                 230                 235                 240

Phe Leu Arg Leu Asn His Asn Lys Leu Ser Asp Glu Gly Leu Pro Ser
            245                 250                 255

Arg Gly Phe Asp Val Ser Ser Ile Leu Asp Leu Gln Leu Ser His Asn
            260                 265                 270

Gln Leu Thr Lys Val Pro Arg Ile Ser Ala His Leu His Leu His
        275                 280                 285

Leu Asp His Asn Lys Ile Lys Ser Val Asn Val Ser Val Ile Cys Pro
        290                 295                 300

Ser Pro Ser Met Leu Pro Ala Glu Arg Asp Ser Phe Ser Tyr Gly Pro
305                 310                 315                 320

His Leu Arg Tyr Leu Arg Leu Asp Gly Asn Glu Ile Lys Pro Pro Ile
            325                 330                 335

Pro Met Ala Leu Met Thr Cys Phe Arg Leu Leu Gln Ala Val Ile Ile
            340                 345                 350

<210> SEQ ID NO 33
<211> LENGTH: 9
<212> TYPE: PRT
<213> ORGANISM: Artificial Sequence
<220> FEATURE:
<223> OTHER INFORMATION: Fragment of keratocan protein

<400> SEQUENCE: 33

Leu Gln Asn Asn Leu Ile Glu Thr Ile
1               5

<210> SEQ ID NO 34
<211> LENGTH: 9
<212> TYPE: PRT
<213> ORGANISM: Artificial Sequence
<220> FEATURE:
<223> OTHER INFORMATION: Lumican protein fragment

<400> SEQUENCE: 34

Leu Gln Tyr Leu Arg Leu Ser His Asn
1               5

<210> SEQ ID NO 35
<211> LENGTH: 9
<212> TYPE: PRT
<213> ORGANISM: Artificial Sequence
<220> FEATURE:
<223> OTHER INFORMATION: A second opticin protein fragment

<400> SEQUENCE: 35

Gln Leu Glu Asp Ile Arg Leu Asp Gly
1               5
```

```
<210> SEQ ID NO 36
<211> LENGTH: 9
<212> TYPE: PRT
<213> ORGANISM: Artificial Sequence
<220> FEATURE:
<223> OTHER INFORMATION: Chlamydia histidine kinase fragment

<400> SEQUENCE: 36

Pro Leu Asn Leu Arg Ser Ile Asp Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Artificial chlamydia protein

<400> SEQUENCE: 37

Ala Arg Lys Leu Leu Leu Asp Asn Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Fragment of chlamydia outermembrane protein C

<400> SEQUENCE: 38

Asn Arg Phe Ser Val Ala Tyr Met Leu
1               5

<210> SEQ ID NO 39
<211> LENGTH: 9
<212> TYPE: PRT
<213> ORGANISM: Artificial Sequence
<220> FEATURE:
<223> OTHER INFORMATION: A 9 amino acid modified lumican protein
      fragment
<220> FEATURE:
<221> NAME/KEY: MISC_FEATURE
<222> LOCATION: (3)..(3)
<223> OTHER INFORMATION: Cys at position 3

<400> SEQUENCE: 39

Leu Gln Cys Leu Arg Leu Ser His Asn
1               5

<210> SEQ ID NO 40
<211> LENGTH: 9
<212> TYPE: PRT
<213> ORGANISM: Artificial Sequence
<220> FEATURE:
<223> OTHER INFORMATION: A 9 amino acid modified lumican protein
      fragment with leucine
<220> FEATURE:
<221> NAME/KEY: MISC_FEATURE
<222> LOCATION: (3)..(3)
<223> OTHER INFORMATION: Leu at position 3

<400> SEQUENCE: 40

Leu Gln Leu Leu Arg Leu Ser His Asn
1               5

<210> SEQ ID NO 41
<211> LENGTH: 26
<212> TYPE: PRT
<213> ORGANISM: Artificial Sequence
```

```
<220> FEATURE:
<223> OTHER INFORMATION: Lumican fragment

<400> SEQUENCE: 41

Asp Glu Tyr Phe Lys Arg Phe Asn Ala Leu Gln Tyr Leu Arg Leu Ser
1               5                   10                  15

His Asn Glu Leu Ala Asp Ser Gly Ile Pro
            20                  25

<210> SEQ ID NO 42
<211> LENGTH: 20
<212> TYPE: PRT
<213> ORGANISM: Artificial Sequence
<220> FEATURE:
<223> OTHER INFORMATION: Lumican fragment

<400> SEQUENCE: 42

Asp Glu Tyr Phe Lys Arg Phe Asn Ala Leu Gln Tyr Leu Arg Leu Ser
1               5                   10                  15

His Asn Glu Leu
            20

<210> SEQ ID NO 43
<211> LENGTH: 11
<212> TYPE: PRT
<213> ORGANISM: Artificial Sequence
<220> FEATURE:
<223> OTHER INFORMATION: Lumican fragment

<400> SEQUENCE: 43

Tyr Phe Lys Arg Phe Asn Ala Leu Gln Tyr Leu
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Lumican fragment

<400> SEQUENCE: 44

Ser Leu Ser Ala Phe Thr Leu Phe Leu
1               5

<210> SEQ ID NO 45
<211> LENGTH: 9
<212> TYPE: PRT
<213> ORGANISM: Artificial Sequence
<220> FEATURE:
<223> OTHER INFORMATION: Lumican fragment

<400> SEQUENCE: 45

Ser Val Gly Pro Leu Pro Lys Ser Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Lumican fragment

<400> SEQUENCE: 46

Leu Ser Tyr Ser Lys Ile Lys His Leu
1               5
```

```
<210> SEQ ID NO 47
<211> LENGTH: 9
<212> TYPE: PRT
<213> ORGANISM: Artificial Sequence
<220> FEATURE:
<223> OTHER INFORMATION: Lumican fragment

<400> SEQUENCE: 47

Gly Leu Pro Val Ser Leu Leu Thr Leu
1               5

<210> SEQ ID NO 48
<211> LENGTH: 9
<212> TYPE: PRT
<213> ORGANISM: Artificial Sequence
<220> FEATURE:
<223> OTHER INFORMATION: Lumican fragment

<400> SEQUENCE: 48

Met Val Pro Pro Gly Ile Lys Tyr Leu
1               5

<210> SEQ ID NO 49
<211> LENGTH: 9
<212> TYPE: PRT
<213> ORGANISM: Artificial Sequence
<220> FEATURE:
<223> OTHER INFORMATION: Lumican fragment

<400> SEQUENCE: 49

Gly Gly Thr Ser Gly Gln Tyr Tyr Asp
1               5

<210> SEQ ID NO 50
<211> LENGTH: 9
<212> TYPE: PRT
<213> ORGANISM: Artificial Sequence
<220> FEATURE:
<223> OTHER INFORMATION: Lumican fragment

<400> SEQUENCE: 50

Tyr Leu Arg Leu Ser His Asn Glu Leu
1               5

<210> SEQ ID NO 51
<211> LENGTH: 9
<212> TYPE: PRT
<213> ORGANISM: Artificial Sequence
<220> FEATURE:
<223> OTHER INFORMATION: Lumican fragment

<400> SEQUENCE: 51

Ser Tyr Pro Ser Ala Met Tyr Cys Asp
1               5

<210> SEQ ID NO 52
<211> LENGTH: 9
<212> TYPE: PRT
<213> ORGANISM: Artificial Sequence
<220> FEATURE:
<223> OTHER INFORMATION: Lumican fragment

<400> SEQUENCE: 52

Leu Gln His Asn Arg Leu Lys Glu Asp
1               5
```

```
<210> SEQ ID NO 53
<211> LENGTH: 9
<212> TYPE: PRT
<213> ORGANISM: Artificial Sequence
<220> FEATURE:
<223> OTHER INFORMATION: Lumican fragment

<400> SEQUENCE: 53

Phe Asn Val Ser Ser Leu Val Glu Leu
1               5

<210> SEQ ID NO 54
<211> LENGTH: 9
<212> TYPE: PRT
<213> ORGANISM: Artificial Sequence
<220> FEATURE:
<223> OTHER INFORMATION: Lumican fragment

<400> SEQUENCE: 54

Ser Phe Asn Val Ser Ser Leu Val Glu
1               5

<210> SEQ ID NO 55
<211> LENGTH: 9
<212> TYPE: PRT
<213> ORGANISM: Artificial Sequence
<220> FEATURE:
<223> OTHER INFORMATION: Lumican fragment

<400> SEQUENCE: 55

Leu Arg Val Ala Asn Glu Val Thr Leu
1               5

<210> SEQ ID NO 56
<211> LENGTH: 9
<212> TYPE: PRT
<213> ORGANISM: Artificial Sequence
<220> FEATURE:
<223> OTHER INFORMATION: Lumican fragment

<400> SEQUENCE: 56

Leu Pro Pro Asp Met Tyr Glu Cys Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Cell binding peptide

<400> SEQUENCE: 57

Phe Asn Ala Leu Gln Tyr Leu Arg Leu
1               5

<210> SEQ ID NO 58
<211> LENGTH: 9
<212> TYPE: PRT
<213> ORGANISM: Artificial Sequence
<220> FEATURE:
<223> OTHER INFORMATION: Cell binding peptide

<400> SEQUENCE: 58

Arg Leu Lys Glu Asp Ala Val Ser Ala
1               5

<210> SEQ ID NO 59
```

```
<211> LENGTH: 9
<212> TYPE: PRT
<213> ORGANISM: Artificial Sequence
<220> FEATURE:
<223> OTHER INFORMATION: Cell binding peptide

<400> SEQUENCE: 59

Pro Phe Gly Ile Lys Tyr Leu Tyr Leu
1               5

<210> SEQ ID NO 60
<211> LENGTH: 9
<212> TYPE: PRT
<213> ORGANISM: Artificial Sequence
<220> FEATURE:
<223> OTHER INFORMATION: Cell binding peptide

<400> SEQUENCE: 60

Phe Lys Arg Phe Asn Ala Leu Gln Tyr
1               5

<210> SEQ ID NO 61
<211> LENGTH: 9
<212> TYPE: PRT
<213> ORGANISM: Artificial Sequence
<220> FEATURE:
<223> OTHER INFORMATION: Cell binding peptide

<400> SEQUENCE: 61

Ala Leu Gln Tyr Leu Arg Leu Ser His
1               5

<210> SEQ ID NO 62
<211> LENGTH: 9
<212> TYPE: PRT
<213> ORGANISM: Artificial Sequence
<220> FEATURE:
<223> OTHER INFORMATION: Cell binding peptide

<400> SEQUENCE: 62

Glu Tyr Phe Lys Arg Phe Asn Ala Leu
1               5

<210> SEQ ID NO 63
<211> LENGTH: 8
<212> TYPE: PRT
<213> ORGANISM: Artificial Sequence
<220> FEATURE:
<223> OTHER INFORMATION: Cell binding peptide

<400> SEQUENCE: 63

Leu Arg Leu Ser His Asn Glu Leu
1               5

<210> SEQ ID NO 64
<211> LENGTH: 9
<212> TYPE: PRT
<213> ORGANISM: Artificial Sequence
<220> FEATURE:
<223> OTHER INFORMATION: Cell binding peptide

<400> SEQUENCE: 64

Arg Arg Gln Leu Glu Asp Ile Arg Leu
1               5

<210> SEQ ID NO 65
<211> LENGTH: 9
```

```
<212> TYPE: PRT
<213> ORGANISM: Artificial Sequence
<220> FEATURE:
<223> OTHER INFORMATION: Cell binding peptide

<400> SEQUENCE: 65

Leu Arg Leu Ser His Asn Glu Leu Ala
1               5

<210> SEQ ID NO 66
<211> LENGTH: 9
<212> TYPE: PRT
<213> ORGANISM: Artificial Sequence
<220> FEATURE:
<223> OTHER INFORMATION: Cell binding peptide

<400> SEQUENCE: 66

Glu His Lys His Thr Arg Arg Gln Leu
1               5

<210> SEQ ID NO 67
<211> LENGTH: 9
<212> TYPE: PRT
<213> ORGANISM: Artificial Sequence
<220> FEATURE:
<223> OTHER INFORMATION: Cell binding peptide

<400> SEQUENCE: 67

His Lys His Thr Arg Arg Gln Leu Glu
1               5

<210> SEQ ID NO 68
<211> LENGTH: 9
<212> TYPE: PRT
<213> ORGANISM: Artificial Sequence
<220> FEATURE:
<223> OTHER INFORMATION: Cell binding peptide

<400> SEQUENCE: 68

Lys His Thr Arg Arg Gln Leu Glu Asp
1               5

<210> SEQ ID NO 69
<211> LENGTH: 9
<212> TYPE: PRT
<213> ORGANISM: Artificial Sequence
<220> FEATURE:
<223> OTHER INFORMATION: Cell binding peptide

<400> SEQUENCE: 69

His Thr Arg Arg Gln Leu Glu Asp Ile
1               5

<210> SEQ ID NO 70
<211> LENGTH: 9
<212> TYPE: PRT
<213> ORGANISM: Artificial Sequence
<220> FEATURE:
<223> OTHER INFORMATION: Cell binding peptide

<400> SEQUENCE: 70

Thr Arg Arg Gln Leu Glu Asp Ile Arg
1               5

<210> SEQ ID NO 71
<211> LENGTH: 9
<212> TYPE: PRT
```

```
<213> ORGANISM: Artificial Sequence
<220> FEATURE:
<223> OTHER INFORMATION: Cell binding peptide

<400> SEQUENCE: 71

Arg Gln Leu Glu Asp Ile Arg Leu Asp
1               5

<210> SEQ ID NO 72
<211> LENGTH: 9
<212> TYPE: PRT
<213> ORGANISM: Artificial Sequence
<220> FEATURE:
<223> OTHER INFORMATION: Cell binding peptide

<400> SEQUENCE: 72

Leu Glu Asp Ile Arg Leu Asp Gly Asn
1               5

<210> SEQ ID NO 73
<211> LENGTH: 9
<212> TYPE: PRT
<213> ORGANISM: Artificial Sequence
<220> FEATURE:
<223> OTHER INFORMATION: Cell binding peptide

<400> SEQUENCE: 73

Asp Glu Tyr Phe Lys Arg Phe Asn Ala
1               5

<210> SEQ ID NO 74
<211> LENGTH: 9
<212> TYPE: PRT
<213> ORGANISM: Artificial Sequence
<220> FEATURE:
<223> OTHER INFORMATION: Cell binding peptide

<400> SEQUENCE: 74

Tyr Phe Lys Arg Phe Asn Ala Leu Gln
1               5

<210> SEQ ID NO 75
<211> LENGTH: 9
<212> TYPE: PRT
<213> ORGANISM: Artificial Sequence
<220> FEATURE:
<223> OTHER INFORMATION: Cell binding peptide

<400> SEQUENCE: 75

Arg Phe Asn Ala Leu Gln Tyr Leu Arg
1               5

<210> SEQ ID NO 76
<211> LENGTH: 9
<212> TYPE: PRT
<213> ORGANISM: Artificial Sequence
<220> FEATURE:
<223> OTHER INFORMATION: Cell binding peptide

<400> SEQUENCE: 76

Asn Ala Leu Gln Tyr Leu Arg Leu Ser
1               5

<210> SEQ ID NO 77
<211> LENGTH: 9
<212> TYPE: PRT
<213> ORGANISM: Artificial Sequence
```

```
<220> FEATURE:
<223> OTHER INFORMATION: Cell binding peptide

<400> SEQUENCE: 77

Ala Leu Gln Tyr Leu Arg Leu Ser His
1               5

<210> SEQ ID NO 78
<211> LENGTH: 9
<212> TYPE: PRT
<213> ORGANISM: Artificial Sequence
<220> FEATURE:
<223> OTHER INFORMATION: Cell binding peptide

<400> SEQUENCE: 78

Gln Tyr Leu Arg Leu Ser His Asn Glu
1               5

<210> SEQ ID NO 79
<211> LENGTH: 6
<212> TYPE: PRT
<213> ORGANISM: Artificial Sequence
<220> FEATURE:
<223> OTHER INFORMATION: Cell binding peptide

<400> SEQUENCE: 79

Leu Ser His Asn Glu Leu
1               5

<210> SEQ ID NO 80
<211> LENGTH: 9
<212> TYPE: PRT
<213> ORGANISM: Artificial Sequence
<220> FEATURE:
<223> OTHER INFORMATION: Cell binding peptide

<400> SEQUENCE: 80

Leu Asn Leu Arg Ser Ile Asp Leu Gln
1               5

<210> SEQ ID NO 81
<211> LENGTH: 9
<212> TYPE: PRT
<213> ORGANISM: Artificial Sequence
<220> FEATURE:
<223> OTHER INFORMATION: Cell binding peptide

<400> SEQUENCE: 81

Asn Leu Arg Ser Ile Asp Leu Gln Asp
1               5

<210> SEQ ID NO 82
<211> LENGTH: 9
<212> TYPE: PRT
<213> ORGANISM: Artificial Sequence
<220> FEATURE:
<223> OTHER INFORMATION: Cell binding peptide

<400> SEQUENCE: 82

Leu Arg Ser Ile Asp Leu Gln Asp Phe
1               5

<210> SEQ ID NO 83
<211> LENGTH: 9
<212> TYPE: PRT
<213> ORGANISM: Artificial Sequence
<220> FEATURE:
```

<223> OTHER INFORMATION: Cell binding peptide

<400> SEQUENCE: 83

Arg Ser Ile Asp Leu Gln Asp Phe Phe
1               5

<210> SEQ ID NO 84
<211> LENGTH: 9
<212> TYPE: PRT
<213> ORGANISM: Artificial Sequence
<220> FEATURE:
<223> OTHER INFORMATION: Cell binding peptide

<400> SEQUENCE: 84

Ser Ile Asp Leu Gln Asp Phe Phe Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Cell binding peptide

<400> SEQUENCE: 85

Ile Asp Leu Gln Asp Phe Phe Ser Ser
1               5

<210> SEQ ID NO 86
<211> LENGTH: 9
<212> TYPE: PRT
<213> ORGANISM: Artificial Sequence
<220> FEATURE:
<223> OTHER INFORMATION: Cell binding peptide

<400> SEQUENCE: 86

Asp Leu Gln Asp Phe Phe Ser Ser Leu
1               5

<210> SEQ ID NO 87
<211> LENGTH: 9
<212> TYPE: PRT
<213> ORGANISM: Artificial Sequence
<220> FEATURE:
<223> OTHER INFORMATION: Cell binding peptide

<400> SEQUENCE: 87

Leu Gln Asp Phe Phe Ser Ser Leu Ile
1               5

<210> SEQ ID NO 88
<211> LENGTH: 9
<212> TYPE: PRT
<213> ORGANISM: Artificial Sequence
<220> FEATURE:
<223> OTHER INFORMATION: Cell binding peptide

<400> SEQUENCE: 88

Asp Pro Cys Thr Thr Trp Cys Asp Ala
1               5

<210> SEQ ID NO 89
<211> LENGTH: 9
<212> TYPE: PRT
<213> ORGANISM: Artificial Sequence
<220> FEATURE:
<223> OTHER INFORMATION: Cell binding peptide

```
<400> SEQUENCE: 89

Arg Arg Arg Trp Arg Arg Leu Thr Val
1               5

<210> SEQ ID NO 90
<211> LENGTH: 9
<212> TYPE: PRT
<213> ORGANISM: Artificial Sequence
<220> FEATURE:
<223> OTHER INFORMATION: Collagen type II alpha I fragment

<400> SEQUENCE: 90

Ala Arg Gly Gln Pro Gly Val Met Gly
1               5

<210> SEQ ID NO 91
<211> LENGTH: 9
<212> TYPE: PRT
<213> ORGANISM: Artificial Sequence
<220> FEATURE:
<223> OTHER INFORMATION: Collagen peptide fragment

<400> SEQUENCE: 91

Asp Arg Ala Ser Phe Ile Lys Asn Leu
1               5

<210> SEQ ID NO 92
<211> LENGTH: 9
<212> TYPE: PRT
<213> ORGANISM: Artificial Sequence
<220> FEATURE:
<223> OTHER INFORMATION: Aggrecan peptide fragment

<400> SEQUENCE: 92

Ser Arg His His Ala Phe Cys Phe Arg
1               5

<210> SEQ ID NO 93
<211> LENGTH: 9
<212> TYPE: PRT
<213> ORGANISM: Artificial Sequence
<220> FEATURE:
<223> OTHER INFORMATION: Chlamydia peptide fragment

<400> SEQUENCE: 93

Lys Arg Leu Ala Glu Thr Leu Ala Leu
1               5

<210> SEQ ID NO 94
<211> LENGTH: 9
<212> TYPE: PRT
<213> ORGANISM: Artificial Sequence
<220> FEATURE:
<223> OTHER INFORMATION: Chlamydia peptide fragment

<400> SEQUENCE: 94

Ile Arg Ser Ser Val Gln Asn Lys Leu
1               5
```